United States Patent
Wilson et al.

(10) Patent No.: US 9,000,009 B2
(45) Date of Patent: Apr. 7, 2015

(54) SMALL MOLECULE ACTIVATORS OF MITOCHONDRIAL FUNCTION

(75) Inventors: Robert B. Wilson, Wynnewood, PA (US); Maria Grazia Cotticelli, Philadelphia, PA (US); Phillip A. Benedetti, South San Francisco, CA (US); Amos Smith, Merion, PA (US); Jason E. Melvin, Philadelphia, PA (US); Donna M Huryn, Allentown, NJ (US)

(73) Assignee: The Trustees Of The University Of Pennsylvania, Philadelphia, PA (US)

( * ) Notice: Subject to any disclaimer, the term of this patent is extended or adjusted under 35 U.S.C. 154(b) by 0 days.

(21) Appl. No.: 13/139,162

(22) PCT Filed: Dec. 10, 2009

(86) PCT No.: PCT/US2009/067517
§ 371 (c)(1),
(2), (4) Date: Oct. 26, 2011

(87) PCT Pub. No.: WO2010/068767
PCT Pub. Date: Jun. 17, 2010

(65) Prior Publication Data
US 2012/0041023 A1    Feb. 16, 2012

Related U.S. Application Data

(60) Provisional application No. 61/121,477, filed on Dec. 10, 2008.

(51) Int. Cl.
*A61K 31/47* (2006.01)

(52) U.S. Cl.
CPC ..................................... *A61K 31/47* (2013.01)

(58) Field of Classification Search
None
See application file for complete search history.

(56) References Cited

U.S. PATENT DOCUMENTS

2006/0089380 A1    4/2006   Barnham et al.
2008/0146623 A1    6/2008   Deziel et al.

FOREIGN PATENT DOCUMENTS

WO    WO 2008/014602 A1 *   2/2008

OTHER PUBLICATIONS

Pandolfo, Massimo, Frataxin Deficiency and Mitochondrial Dysfunction, 2 Mitochondrion 87-93 (2002).*
Rai et al. HDAC Inhibitors Correct Frataxin Deficiency in Friedreich's Ataxia Mouse Model in Journal PLOS One, vol. 3, Apr. 9, 2008 pp. 1-8, p. 1, abstract; p. 2, col. 1, para 3.
Calmels et al., "The first cellular models based on frataxin missense mutations that reproduce spontaneously the defects associated with Friedreich ataxia", PLoS One. Jul. 24, 2009;4(7):e6379.
Goodson. "In Medical Applications of Controlled Release", supra, vol. 2, pp. 115-138, (1984).
Langer et al. "New methods of drug delivery" Science vol. 249 No. 4976 pp. 1527-1533 Sep. 28, 1990.
Saudek et al. "A preliminary trial of the programmable implantable medication system for insulin delivery." N. Engl. J. Med. 321:574 (1989).
Sefton, 1987, "Implantable pumps." CRC Crit. Ref. Biomed. Eng. 14:201.
Buchwald et al. "Long-term, continuous intravenous heparin administration by an implantable infusion pump in ambulatory patients with recurrent venous thrombosis." Surgery 88:507 (1980).

* cited by examiner

*Primary Examiner* — Timothy R Rozof
(74) *Attorney, Agent, or Firm* — Mark S. Cohen; Pearl Cohen Zedek Latzer Baratz LLP

(57) ABSTRACT

Methods for improving mitochondrial function, decreasing iron accumulation, and/or decreasing oxidative stress by exposing cells or treating a subject to compounds or compositions of the general formula (I) are described that are beneficial in treating, for example, diseases and conditions such as Friedreich's ataxia, normal aging, and various neurodegenerative diseases such as Alzheimer's disease and Parkinson's disease. Furthermore, such compounds are useful as probes for identifying defects in mitochondrial metabolism, mitochondrial iron accumulation, cellular stress among other mitochondrial diseases and helping to identify compounds active in overcoming such defects.

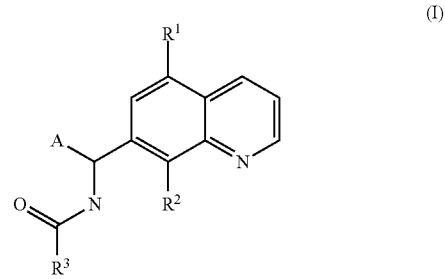

(I)

15 Claims, No Drawings

SMALL MOLECULE ACTIVATORS OF MITOCHONDRIAL FUNCTION

CROSS REFERENCE TO RELATED APPLICATIONS

This application is a National Phase Application of PCT International Application PCT/US09/67517, filed Dec. 10, 2009 that claims priority to U.S. Provisional Patent Application 61/121,477, filed Dec. 10, 2008, both of which are incorporated by reference herein in their entirety.

BACKGROUND OF THE INVENTION

Mitochondrial dysfunction has been established to contribute to the pathology of numerous diseases and is suspected in many more. A role for loss of mitochondrial function in normal aging has long been suspected. Most hypotheses focus on free radical damage to mitochondrial DNA. Mitochondrial DNA (mtDNA) lies in close proximity to the mitochondrial respiratory chain, which produces free radicals even during normal respiration. Somatic mtDNA mutations accumulate with age in post-mitotic tissues in association with a decline in mitochondrial function. MtDNA mutations are propagated during the turnover of mitochondria, which have a limited lifespan of only a few weeks, even in post-mitotic cells. Because mtDNA contributes disproportionally to respiratory complexes I, III, and IV, these complexes are disproportionally affected when mtDNA is damaged. Disproportional effects on mitochondrial respiratory complexes increase the production of free radicals by impeding the normal flux of electrons through the electron transport chain; the increase in free radicals causes further damage to mtDNA, creating a vicious cycle. That the association between the accumulation of mtDNA mutations and aging is likely not an epiphenomenon is indicated by the striking premature aging phenotype of transgenic mice with an increased mtDNA mutation rate due to expression of a proof-reading-defective mitochondrial DNA polymerase.

Loss of mitochondrial function, particularly complex I function, likely contributes to Parkinson's disease (PD) as well. Complex I (NADH-ubiquinone oxidoreductase) activity is selectively decreased 15-30% in the substantia nigra (SN) in sporadic PD. 1-Methyl-4-phenyl-1,2,3,6-tetrahydropyridine (MPTP) is a neurotoxin that causes a parkinsonian syndrome in humans and mice: MPTP is metabolized in the brain to MPP+, a complex I inhibitor that accumulates in dopaminergic neurons. Chronic inhibition of complex I with rotenone, throughout the brain, causes selective degeneration of dopaminergic neurons in the SN. Rotenone-treated rats develop all the pathological hallmarks of PD, including distribution of pathology, nigrostriatal dopaminergic neurodegeneration, formation of Lewy-Body-like cytoplasmic inclusions, and oxidative damage. The hypokinesia in rats treated with rotenone may also reflect, at least in part, a general health problem rather than loss of nigrostriatal dopaminergic neurons.

A role for mitochondrial dysfunction in Friedreich's ataxia (FRDA or FA) is also recognized. FRDA is an inherited disease that causes progressive damage to the nervous system and muscle cells resulting in symptoms ranging from uncoordination, gait disturbance, and speech problems to heart disease and muscle fatigueability. FRDA has a prevalence of approximately 1 in 40,000 in Caucasians. FRDA is characterized by progressive ataxia of all four limbs, dysarthria, areflexia, sensory loss, and exercise intolerance. Skeletal deformities and cardiomyopathy are found in most patients, impaired glucose tolerance and diabetes mellitus are found in ~30% of patients, and reduced visual acuity, including a pigmentary retinopathy, and hearing loss are occasionally seen. Symptoms usually begin between the ages of 5 and 15 but can, on rare occasions, appear as early as 18 months or as late as 50 years of age. The first symptom to appear is usually difficulty in walking, or gait ataxia. The ataxia gradually worsens and slowly spreads to the arms and then the trunk. Foot deformities such as clubfoot, flexion (involuntary bending) of the toes, hammer toes, or foot inversion (turning inward) may be early signs. Over time, muscles begin to atrophy, especially in the feet, lower legs, and hands, and deformities develop. Other symptoms include loss of deep tendon reflexes, especially in the knees and ankles. Generally, within 10 to 20 years after the appearance of the first symptoms, afflicted individuals are confined to a wheelchair, and in later stages of the disease become completely incapacitated. Life expectancy may be affected, and many people with FRDA die in adulthood from the associated heart disease: myocardial failure is the most common cause of premature death (http://www.ninds.nih.gov/disorders/friedreichs_ataxia). There are currently no approved treatments for FRDA.

Friedreich's ataxia is an autosomal recessive disease caused by a triplet repeat expansion in the frataxin gene, which leads to decreased frataxin protein levels. Frataxin is found primarily in mitochondria where it chaperones iron for the formation of iron-sulfur clusters and may also act to store and detoxify excess iron. Iron-sulfur clusters are important prosthetic groups in the mitochondrial electron transport chain and other enzymes, including aconitase in the Krebs cycle. Decreased frataxin levels contribute to mitochondrial dysfunction and mitochondrial iron accumulation, which are believed to lead to increased production of toxic oxidants, which can further impair mitochondrial and cellular function. Mitochondrial dysfunction is believed to be responsible for most, if not all, of the pathologies described above.

SUMMARY OF THE INVENTION

In one embodiment, a method is provided for increasing cellular frataxin gene expression or the phenotype thereof in a subject comprising administering to the subject an effective amount of a compound of formula (I) or a pharmaceutical composition thereof:

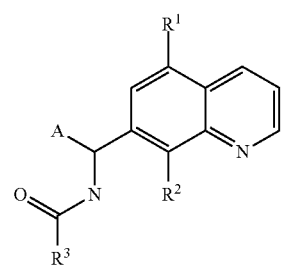

wherein A is an optionally substituted aliphatic, alicyclic, heteroaliphatic, heterocyclic, aromatic, or heteroaromatic;

$R^1$ is hydrogen, hydroxy, halogen, cyano, alkyloxy, nitro, $NH_2$, $NHCOR^4$, $NHSO_2R^4$, $CONHR^4$, $COOR^4$, or an optionally substituted aliphatic, alicyclic, heteroaliphatic, heterocyclic, aromatic, or heteroaromatic;

$R^2$ is —OR, wherein R is —$C_1$-$C_6$-alkyl, —$C_2$-$C_6$-alkenyl, —$C_2$-$C_6$-alkynyl, —$SO_2NR^4R^6$, —$SO_2R^7$, —$COR^7$, —$COOR^7$ or —$CONR^4R^6$, wherein (a) one or more of the carbon atoms in the alkyl, alkenyl or alkynyl group is each independently optionally replaced with a nitrogen, sulfur or oxygen atom, and (b) the alkyl, alkenyl or alkynyl group is optionally substituted with a —$C_1$-$C_3$-alkyl;

$R^3$ is an optionally substituted aliphatic, alicyclic, heteroaliphatic, heterocyclic, aromatic, or heteroaromatic; and $R^4$ and $R^6$ are each independently hydrogen, —$C_1$-$C_6$-alkyl, —$C_2$-$C_6$-alkenyl, —$C_2$-$C_6$-alkynyl, —$COR^7$, —$C_5$-$C_7$-aryl, or —$C_5$-$C_{10}$-arylalkyl, wherein (a) one or more of the carbon atoms in the alkyl, alkenyl, alkynyl, aryl or arylalkyl group is each independently optionally replaced with a nitrogen, sulfur or oxygen atom, and (b) the alkyl, alkenyl, alkynyl, aryl or arylalkyl is optionally substituted with an oxygen, a —$C_1$-$C_3$-alkyl, or a —$C_5$-$C_7$-aryl; and $R^7$ is hydrogen, —$C_1$-$C_6$-alkyl, —$C_2$-$C_6$-alkenyl, —$C_2$-$C_6$-alkynyl, —$C_5$-$C_7$-aryl, or —$C_5$-$C_{10}$-arylalkyl, wherein (a) one or more of the carbon atoms in the alkyl, alkenyl, alkynyl, aryl or arylalkyl group is each independently optionally replaced with a nitrogen, sulfur or oxygen atom, and (b) the alkyl, alkenyl, alkynyl, aryl or arylalkyl is optionally substituted with a halogen, a —$C_1$-$C_3$-alkyl, a —$C_5$-$C_7$-aryl, or —$NR^4R^6$ or —$OR^4$;

or an isomer, stereoisomer, racemate, prodrug, active metabolite, metal chelate, or a pharmaceutically-acceptable derivative or salt form of any of the foregoing.

In certain embodiments, $R^1$ is chloro, nitro or cyano. In other embodiments $R^2$ is hydroxy. In other embodiments, A is a substituted aryl group or an optionally substituted furyl group. In further embodiments, $R^3$ is an optionally substituted alkyl or aralkyl group.

In certain embodiments, the compound of formula (I) has the structure of formula (II):

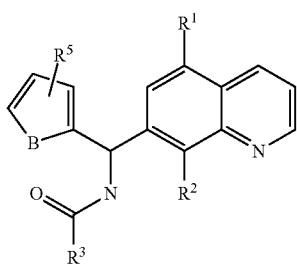

II wherein B is O, N or S;

$R^1$ is hydrogen, hydroxy, halogen, cyano, alkyloxy, nitro, $NH_2$, $NHCOR^4$, $NHSO_2R^4$, $CONHR^4$, $COOR^4$, or an optionally substituted aliphatic, alicyclic, heteroaliphatic, heterocyclic, aromatic, or heteroaromatic;

$R^2$ is —OR, wherein R is —$C_1$-$C_6$-alkyl, —$C_2$-$C_6$-alkenyl, —$C_2$-$C_6$-alkynyl, —$SO_2NR^4R^6$, —$SO_2R^7$, —$COR^7$, —$COOR^7$ or —$CONR^4R^6$, wherein (a) one or more of the carbon atoms in the alkyl, alkenyl or alkynyl group is each independently optionally replaced with a nitrogen, sulfur or oxygen atom, and (b) the alkyl, alkenyl or alkynyl group is optionally substituted with a —$C_1$-$C_3$-alkyl;

$R^3$ is an optionally substituted aliphatic, alicyclic, heteroaliphatic, heterocyclic, aromatic, or hetero aromatic;

$R^4$ and $R^6$ are each independently hydrogen, —$C_1$-$C_6$-alkyl, —$C_2$-$C_6$-alkenyl, —$C_2$-$C_6$-alkynyl, —$COR^7$, —$C_5$-$C_7$-aryl, or —$C_5$-$C_{10}$-arylalkyl, wherein (a) one or more of the carbon atoms in the alkyl, alkenyl, alkynyl, aryl or arylalkyl group is each independently optionally replaced with a nitrogen, sulfur or oxygen atom, and (b) the alkyl, alkenyl, alkynyl, aryl or arylalkyl is optionally substituted with an oxygen, a —$C_1$-$C_3$-alkyl, or a —$C_5$-$C_7$-aryl;

$R^5$ is one or more hydrogen, hydroxy, halogen, cyano, alkyloxy, nitro, $NH_2$, $NHCOR^4$, $NHSO_2R^4$, $CONHR^4$, $COOR^4$, optionally substituted aliphatic, alicyclic, heteroaliphatic, heterocyclic, aromatic, or heteroaromatic; and $R^7$ is hydrogen, —$C_1$-$C_6$-alkyl, —$C_2$-$C_6$-alkenyl, —$C_2$-$C_6$-alkynyl, —$C_5$-$C_7$-aryl, or —$C_5$-$C_{10}$-arylalkyl, wherein (a) one or more of the carbon atoms in the alkyl, alkenyl, alkynyl, aryl or arylalkyl group is each independently optionally replaced with a nitrogen, sulfur or oxygen atom, and (b) the alkyl, alkenyl, alkynyl, aryl or arylalkyl is optionally substituted with a halogen, a —$C_1$-$C_3$-alkyl, a —$C_5$-$C_7$-aryl, or —$NR^4R^6$ or —$OR^4$;

or an isomer, enantiomer, racemate, prodrug, active metabolite, metal chelate, or a pharmaceutically-acceptable derivative or salt form of any of the foregoing.

In certain embodiments, $R^1$ is chloro, nitro or cyano. In other embodiments $R^2$ is hydroxy. In other embodiments, $R^3$ can be alkyl or aralkyl.

In certain embodiments, $R^1$ is chloro and $R^2$ is hydroxy. In other embodiments, B is O. In further embodiments, $R^3$ is an optionally substituted alkyl or aralkyl group.

Non-limiting examples of such compounds include N-[(5-chloro-8-hydroxyquinolin-7-yl)-thiophen-2-ylmethyl]-3-phenylpropanamide, N-[(5-chloro-8-hydroxyquinolin-7-yl)-thiophen-2-ylmethyl]pentanamide, N-[(5-chloro-8-hydroxyquinolin-7-yl)-thiophen-2-ylmethyl]propanamide, N-[(5-chloro-8-hydroxyquinolin-7-yl)-thiophen-2-ylmethyl]-2-methylpropanamide, N-[(5-chloro-8-hydroxyquinolin-7-yl)-thiophen-2-ylmethyl]butanamide, N-[(5-chloro-8-hydroxyquinolin-7-yl)-thiophen-2-ylmethyl]acetamide, N-[(8-hydroxy-5-nitroquinolin-7-yl)-thiophen-2-ylmethyl]butanamide, N-[(8-hydroxy-5-nitro-quinolin-7-yl)-thiophen-2-yl-methyl]-acetamide, N-[(8-hydroxy-5-nitro-quinolin-7-yl)-thiophen-2-yl-methyl]-propionamide, N-[2-furyl(8-hydroxy-5-nitro-7-quinolinyl)methyl]butanamide, N-[(8-hydroxyquinolin-7-yl)-thiophen-2-ylmethyl]-3-phenylpropanamide, N-[(5-chloro-8-hydroxyquinolin-7-yl)-furan-2-ylmethyl]-3-phenylpropanamide, N-[(5-chloro-8-hydroxyquinolin-7-yl)-furan-2-ylmethyl]propanamide, and N-[(5-chloro-8-hydroxyquinolin-7-yl)-furan-2-ylmethyl]pentanamide.

In certain other embodiments, compound (I) has the structure of formula (III)

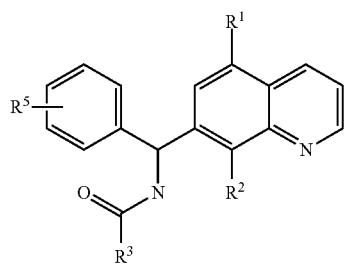

III wherein $R^1$ is hydrogen, hydroxy, halogen, cyano, alkyloxy, nitro, $NH_2$, $NHCOR^4$, $NHSO_2R^4$, $CONHR^4$, COOR⁴, or an optionally substituted aliphatic, alicyclic, heteroaliphatic, heterocyclic, aromatic, or heteroaromatic;

$R^2$ is —OR, wherein R is —$C_1$-$C_6$-alkyl, —$C_2$-$C_6$-alkenyl, —$C_2$-$C_6$-alkynyl, —$SO_2NR^4R^6$, —$SO_2R^7$, —$COR^7$, —$COOR^7$ or —$CONR^4R^6$, wherein (a) one or more of the carbon atoms in the alkyl, alkenyl or alkynyl group is each independently optionally replaced with a nitrogen, sulfur or oxygen atom, and (b) the alkyl, alkenyl or alkynyl group is optionally substituted with a —$C_1$-$C_3$-alkyl;

$R^3$ is an optionally substituted aliphatic, alicyclic, heteroaliphatic, heterocyclic, aromatic, or hetero aromatic;

$R^4$ and $R^6$ are each independently hydrogen, —$C_1$-$C_6$-alkyl, —$C_2$-$C_6$-alkenyl, —$C_2$-$C_6$-alkynyl, —$COR^7$, —$C_5$-$C_7$-aryl, or —$C_5$-$C_{10}$-arylalkyl, wherein (a) one or more of the carbon atoms in the alkyl, alkenyl, alkynyl, aryl or arylalkyl group is each independently optionally replaced with a nitrogen, sulfur or oxygen atom, and (b) the alkyl, alkenyl, alkynyl, aryl or arylalkyl is optionally substituted with an oxygen, a —$C_1$-$C_3$-alkyl, or a —$C_5$-$C_7$-aryl;

$R^5$ is one or more hydrogen, hydroxy, halogen, cyano, alkyloxy, nitro, $NH_2$, $NHCOR^4$, $NHSO_2R^4$, $CONHR^4$, $COOR^4$, optionally substituted aliphatic, alicyclic, heteroaliphatic, heterocyclic, aromatic, or heteroaromatic; and $R^7$ is hydrogen, —$C_1$-$C_6$-alkyl, —$C_2$-$C_6$-alkenyl, —$C_2$-$C_6$-alkynyl, —$C_5$-$C_7$-aryl, or —$C_5$-$C_{10}$-arylalkyl, wherein (a) one or more of the carbon atoms in the alkyl, alkenyl, alkynyl, aryl or arylalkyl group is each independently optionally replaced with a nitrogen, sulfur or oxygen atom, and (b) the alkyl, alkenyl, alkynyl, aryl or arylalkyl is optionally substituted with a halogen, a —$C_1$-$C_3$-alkyl, a —$C_5$-$C_7$-aryl, or —$NR^4R^6$ or —$OR^4$;

or an isomer, enantiomer, racemate, prodrug, active metabolite, metal chelate, or a pharmaceutically-acceptable derivative or salt form of any of the foregoing.

In certain embodiments, $R^1$ is chloro, nitro or cyano. In other embodiments $R^2$ is hydroxy. In other embodiments, $R^3$ can be alkyl or aralkyl.

In certain embodiments, $R^1$ is chloro and $R^2$ is hydroxy. In other embodiments, $R^5$ is one or more methoxy, hydroxy, halo, or dimethylamino groups. In further embodiments, $R^3$ is an optionally substituted alkyl or aralkyl group.

Non-limiting examples of such compounds include N-[(5-chloro-8-hydroxyquinolin-7-yl)-(3,4-dimethoxyphenyl)methyl]propanamide, N-[(5-chloro-8-hydroxyquinolin-7-yl)-(4-methoxyphenyl)methyl]propanamide, N-[(5-chloro-8-hydroxyquinolin-7-yl)-tolyl]-3-phenylpropanamide, N-[(5-chloro-8-hydroxyquinolin-7-yl)-(3-methoxyphenyl)methyl]-3-phenylpropanamide, N-[(5-chloro-8-hydroxyquinolin-7-yl)-(4-dimethylaminophenyl)methyl]-3-phenylpropanamide, N-[(5-chloro-8-hydroxyquinolin-7-yl)-(4-chlorophenyl)methyl]-3-phenylpropanamide, N-[(5-chloro-8-hydroxyquinolin-7-yl)-(3-chlorophenyl)methyl]-3-phenylpropanamide, N-[(5-chloro-8-hydroxyquinolin-7-yl)-(2-chlorophenyl)methyl]-3-phenylpropanamide, N-[(5-chloro-8-hydroxyquinolin-7-yl)-(3,4-dimethoxyphenyl)methyl]-3-phenylpropanamide, N-[(5-chloro-8-hydroxyquinolin-7-yl)-(2,4-dimethoxyphenyl)methyl]-3-phenylpropanamide, N-[(5-chloro-8-hydroxyquinolin-7-yl)-(3,4,5-trimethoxyphenyl)methyl]-3-phenylpropanamide, N-[(5-chloro-8-hydroxyquinolin-7-yl)-(2-bromophenyl)methyl]-3-phenylpropanamide, N-[(5-chloro-8-hydroxyquinolin-7-yl)-p-tolyl-methyl]-3-phenylpropanamide, N-[(5-chloro-8-hydroxyquinolin-7-yl)-(2-hydroxyphenyl)methyl]-3-phenylpropanamide, N-[(5-chloro-8-hydroxyquinolin-7-yl)-(4-methoxyphenyl)methyl]-3-phenylpropanamide, N-[(8-Hydroxy-5-nitro-quinolin-7-yl)-p-tolyl-methyl]-propionamide, N-[{8-hydroxy-5-nitro-7-quinolinyl}(4-methylphenyl)methyl]acetamide, and N-[(8-hydroxyquinolin-7-yl)-(2-methoxyphenyl)methyl]pentanamide.

In a further embodiment, the subject is a Friedreich's ataxia patient or is at risk for developing Friedreich's ataxia.

In another embodiment, a method is provided for increasing cellular frataxin activity or level, or the phenotype thereof, in a subject comprising administering to the subject an effective amount of a compound of formula (I), formula (II) or formula (III) as mentioned above, and such compounds noted above by way of non-limiting example. In certain embodiments, the subject is a Friedreich's ataxia patient or is at risk for developing Friedreich's ataxia.

In yet another embodiment, a method is provided for decreasing mitochondrial iron accumulation or level in a subject or altering iron metabolism or homeostasis therein comprising administering to the subject an effective amount of a compound of formula (I), formula (II), or formula (III) mentioned above, and such compounds noted above by way of non-limiting example. In certain embodiments, the subject is a Friedreich's ataxia patient or is at risk for developing Friedreich's ataxia. In other embodiments, the subject is a patient or individual with or at risk of developing a neurodegenerative disease, neurodegeneration with brain iron accumulation (NBIA), Parkinson's disease, Alzheimer's disease, a mitochondrial encephalopathy, normal aging, hemochromatosis, aceruloplasminemia, thalassemia, attention deficit hyperactivity disorder (ADHD), Tourette's syndrome, diabetes, or age-related macular degeneration. In another embodiment the subject has an iron overload disease or a predisposition or risk of developing an iron overload disease.

In yet another embodiment, a method is provided for decreasing cellular iron import in a subject comprising administering to a subject in need thereof an effective amount of a compound of formula (I), formula (II) or formula (III) mentioned above, and such compounds noted above by way of non-limiting example. In certain embodiments, the subject is a Friedreich's ataxia patient or is at risk for developing Friedreich's ataxia. In other embodiments, the subject is a patient or individual with or at risk of developing a neurodegenerative disease, neurodegeneration with brain iron accumulation (NBIA), Friedreich's ataxia, Parkinson's disease, Alzheimer's disease, a mitochondrial encephalopathy, normal aging, hemochromatosis, aceruloplasminemia, thalassemia, attention deficit hyperactivity disorder (ADHD), Tourette's syndrome, diabetes, or age-related macular degeneration.

In another embodiment, a method is provided for improving mitochondrial or cellular respiratory activity or function in a subject comprising administering to the subject an effective amount of a compound of formula (I), formula (II) or formula (III) mentioned above, and such compounds noted above by way of non-limiting example. In certain embodiments, the subject is a Friedreich's ataxia patient or is at risk for developing Friedreich's ataxia. In other embodiments, the subject is a patient or individual with or at risk of developing a neurodegenerative disease, neurodegeneration with brain iron accumulation (NBIA), Friedreich's ataxia, Parkinson's disease, Alzheimer's disease, a mitochondrial encephalopathy, normal aging, hemochromatosis, aceruloplasminemia, thalassemia, attention deficit hyperactivity disorder (ADHD), Tourette's syndrome, diabetes, or age-related macular degeneration.

In another embodiment, a method is provided for compensating for frataxin deficiency or mutation in a cell, tissue or subject comprising exposing to the cell or tissue or administering to the subject an effective amount of a compound of formula (I), formula (II) or formula (III) mentioned above, and such compounds noted above by way of non-limiting example. In certain embodiments, the subject is a Friedreich's ataxia patient or is at risk for developing Friedreich's ataxia. In other embodiments, the subject is a patient or individual with or at risk of developing a neurodegenerative disease, neurodegeneration with brain iron accumulation (NBIA), Friedreich's ataxia, Parkinson's disease, Alzheimer's disease, a mitochondrial encephalopathy, normal aging, hemochromatosis, aceruloplasminemia, thalassemia, attention deficit hyperactivity disorder (ADHD), Tourette's syndrome, diabetes, or age-related macular degeneration.

In another embodiment, a method is provided for decreasing or reducing oxidative stress in the mitochondria, cells, tissues, or any combination thereof in a subject comprising administering to the subject an effective amount of a compound of formula (I), formula (II) or formula (III) mentioned above, and such compounds noted above by way of non-limiting example. In certain embodiments, the subject is a Friedreich's ataxia patient or is at risk for developing Friedreich's ataxia. In other embodiments, the subject is a patient or individual with or at risk of developing a neurodegenerative disease, neurodegeneration with brain iron accumulation (NBIA), Friedreich's ataxia, Parkinson's disease, Alzheimer's disease, a mitochondrial encephalopathy, normal aging, hemochromatosis, aceruloplasminemia, thalassemia, attention deficit hyperactivity disorder (ADHD), Tourette's syndrome, diabetes, or age-related macular degeneration.

In another embodiment, a method is provided for treating a subject suffering from Friedreich's ataxia or reducing the symptoms thereof comprising administering to the subject an effective amount of a compound of formula (I) or a pharmaceutical composition thereof:

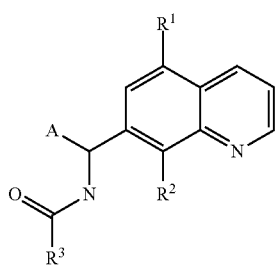

I wherein A is an optionally substituted aliphatic, alicyclic, heteroaliphatic, heterocyclic, aromatic, or heteroaromatic;

$R^1$ is hydrogen, hydroxy, halogen, cyano, alkyloxy, nitro, $NH_2$, $NHCOR^4$, $NHSO_2R^4$, $CONHR^4$, $COOR^4$, or an optionally substituted aliphatic, alicyclic, heteroaliphatic, heterocyclic, aromatic, or heteroaromatic;

$R^2$ is —OR, wherein R is —$C_1$-$C_6$-alkyl, —$C_2$-$C_6$-alkenyl, —$C_2$-$C_6$-alkynyl, —$SO_2NR^4R^6$, —$SO_2R^7$, —$COR^7$, —$COOR^7$ or —$CONR^4R^6$, wherein (a) one or more of the carbon atoms in the alkyl, alkenyl or alkynyl group is each independently optionally replaced with a nitrogen, sulfur or oxygen atom, and (b) the alkyl, alkenyl or alkynyl group is optionally substituted with a —$C_1$-$C_3$-alkyl;

$R^3$ is an optionally substituted aliphatic, alicyclic, heteroaliphatic, heterocyclic, aromatic, or heteroaromatic; and $R^4$ and $R^6$ are each independently hydrogen, —$C_1$-$C_6$-alkyl, —$C_2$-$C_6$-alkenyl, —$C_2$-$C_6$-alkynyl, —$COR^7$, —$C_5$-$C_7$-aryl, or —$C_5$-$C_{10}$-arylalkyl, wherein (a) one or more of the carbon atoms in the alkyl, alkenyl, alkynyl, aryl or arylalkyl group is each independently optionally replaced with a nitrogen, sulfur or oxygen atom, and (b) the alkyl, alkenyl, alkynyl, aryl or arylalkyl is optionally substituted with an oxygen, a —$C_1$-$C_3$-alkyl, or a —$C_5$-$C_7$-aryl; and $R^7$ is hydrogen, —$C_1$-$C_6$-alkyl, —$C_2$-$C_6$-alkenyl, —$C_2$-$C_6$-alkynyl, —$C_5$-$C_7$-aryl, or —$C_5$-$C_{10}$-arylalkyl, wherein (a) one or more of the carbon atoms in the alkyl, alkenyl, alkynyl, aryl or arylalkyl group is each independently optionally replaced with a nitrogen, sulfur or oxygen atom, and (b) the alkyl, alkenyl, alkynyl, aryl or arylalkyl is optionally substituted with a halogen, a —$C_1$-$C_3$-alkyl, a —$C_5$-$C_7$-aryl, or —$NR^4R^6$ or —$OR^4$;

or an isomer, stereoisomer, racemate, prodrug, active metabolite, metal chelate, or a pharmaceutically-acceptable derivative or salt form of any of the foregoing.

In certain embodiments, $R^1$ is chloro, nitro or cyano. In other embodiments $R^2$ is hydroxy. In other embodiments, A is a substituted aryl group or an optionally substituted fury group. In further embodiments, $R^3$ is an optionally substituted alkyl or aralkyl group.

In certain embodiments, the compound of formula (I) has the structure of formula (II):

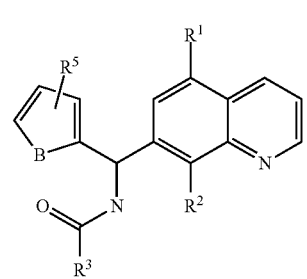

II wherein B is O, N or S;

$R^1$ is hydrogen, hydroxy, halogen, cyano, alkyloxy, nitro, $NH_2$, $NHCOR^4$, $NHSO_2R^4$, $CONHR^4$, $COOR^4$, or an optionally substituted aliphatic, alicyclic, heteroaliphatic, heterocyclic, aromatic, or heteroaromatic;

$R^2$ is —OR, wherein R is —$C_1$-$C_6$-alkyl, —$C_2$-$C_6$-alkenyl, —$C_2$-$C_6$-alkynyl, —$SO_2NR^4R^6$, —$SO_2R^7$, —$COR^7$, —$COOR^7$ or —$CONR^4R^6$, wherein (a) one or more of the carbon atoms in the alkyl, alkenyl or alkynyl group is each independently optionally replaced with a nitrogen, sulfur or oxygen atom, and (b) the alkyl, alkenyl or alkynyl group is optionally substituted with a —$C_1$-$C_3$-alkyl;

$R^3$ is an optionally substituted aliphatic, alicyclic, heteroaliphatic, heterocyclic, aromatic, or hetero aromatic;

$R^4$ and $R^6$ are each independently hydrogen, —$C_1$-$C_6$-alkyl, —$C_2$-$C_6$-alkenyl, —$C_2$-$C_6$-alkynyl, —$COR^7$, —$C_5$-$C_7$-aryl, or —$C_5$-$C_{10}$-arylalkyl, wherein (a) one or more of the carbon atoms in the alkyl, alkenyl, alkynyl, aryl or arylalkyl group is each independently optionally replaced with a nitrogen, sulfur or oxygen atom, and (b)

the alkyl, alkenyl, alkynyl, aryl or arylalkyl is optionally substituted with an oxygen, a —$C_1$-$C_3$-alkyl, or a —$C_5$-$C_7$-aryl;

$R^5$ is one or more hydrogen, hydroxy, halogen, cyano, alkyloxy, nitro, $NH_2$, $NHCOR^4$, $NHSO_2R^4$, $CONHR^4$, $COOR^4$, optionally substituted aliphatic, alicyclic, heteroaliphatic, heterocyclic, aromatic, or heteroaromatic; and $R^7$ is hydrogen, —$C_1$-$C_6$-alkyl, —$C_2$-$C_6$-alkenyl, —$C_2$-$C_6$-alkynyl, —$C_5$-$C_7$-aryl, or —$C_5$-$C_{10}$-arylalkyl, wherein (a) one or more of the carbon atoms in the alkyl, alkenyl, alkynyl, aryl or arylalkyl group is each independently optionally replaced with a nitrogen, sulfur or oxygen atom, and (b) the alkyl, alkenyl, alkynyl, aryl or arylalkyl is optionally substituted with a halogen, a —$C_1$-$C_3$-alkyl, a —$C_5$-$C_7$-aryl, or —$NR^4R^6$ or —$OR^4$;

or an isomer, enantiomer, racemate, prodrug, active metabolite, metal chelate, or a pharmaceutically-acceptable derivative or salt form of any of the foregoing.

In certain embodiments, $R^1$ is chloro, nitro or cyano. In other embodiments $R^2$ is hydroxy. In other embodiments, $R^3$ can be alkyl or aralkyl.

In certain embodiments, $R^1$ is chloro and $R^2$ is hydroxy. In other embodiments, B is O. In further embodiments, $R^3$ is an optionally substituted alkyl or aralkyl group.

Non-limiting examples of such compounds include N-[(5-chloro-8-hydroxyquinolin-7-yl)-thiophen-2-ylmethyl]-3-phenylpropanamide, N-[(5-chloro-8-hydroxyquinolin-7-yl)-thiophen-2-ylmethyl]pentanamide, N-[(5-chloro-8-hydroxyquinolin-7-yl)-thiophen-2-ylmethyl]propanamide, N-[(5-chloro-8-hydroxyquinolin-7-yl)-thiophen-2-ylmethyl]-2-methylpropanamide, N-[(5-chloro-8-hydroxyquinolin-7-yl)-thiophen-2-ylmethyl]butanamide, N-[(5-chloro-8-hydroxyquinolin-7-yl)-thiophen-2-ylmethyl]acetamide, N-[(8-hydroxy-5-nitroquinolin-7-yl)-thiophen-2-ylmethyl]butanamide, N-[(8-hydroxy-5-nitro-quinolin-7-yl)-thiophen-2-yl-methyl]-acetamide, N-[(8-hydroxy-5-nitro-quinolin-7-yl)-thiophen-2-yl-methyl]-propionamide, N-[2-furyl(8-hydroxy-5-nitro-7-quinolinyl)methyl]butanamide, N-[(8-hydroxyquinolin-7-yl)-thiophen-2-ylmethyl]-3-phenylpropanamide, N-[(5-chloro-8-hydroxyquinolin-7-yl)-furan-2-ylmethyl]-3-phenylpropanamide, N-[(5-chloro-8-hydroxyquinolin-7-yl)-furan-2-ylmethyl]propanamide, and N-[(5-chloro-8-hydroxyquinolin-7-yl)-furan-2-ylmethyl]pentanamide.

In certain other embodiments, compound (I) has the structure of formula (III)

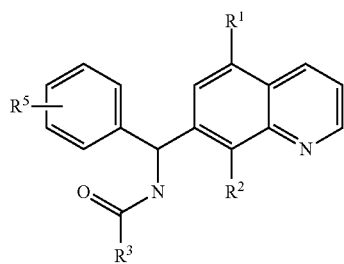

III wherein $R^1$ is hydrogen, hydroxy, halogen, cyano, alkyloxy, nitro, $NH_2$, $NHCOR^4$, $NHSO_2R^4$, $CONHR^4$, $COOR^4$, or an optionally substituted aliphatic, alicyclic, heteroaliphatic, heterocyclic, aromatic, or heteroaromatic;

$R^2$ is —OR, wherein R is —$C_1$-$C_6$-alkyl, —$C_2$-$C_6$-alkenyl, —$C_2$-$C_6$-alkynyl, —$SO_2NR^4R^6$, —$SO_2R^7$, —$COR^7$, —$COOR^7$ or —$CONR^4R^6$, wherein (a) one or more of the carbon atoms in the alkyl, alkenyl or alkynyl group is each independently optionally replaced with a nitrogen, sulfur or oxygen atom, and (b) the alkyl, alkenyl or alkynyl group is optionally substituted with a —$C_1$-$C_3$-alkyl;

$R^3$ is an optionally substituted aliphatic, alicyclic, heteroaliphatic, heterocyclic, aromatic, or hetero aromatic;

$R^4$ and $R^6$ are each independently hydrogen, —$C_1$-$C_6$-alkyl, —$C_2$-$C_6$-alkenyl, —$C_2$-$C_6$-alkynyl, —$COR^7$, —$C_5$-$C_7$-aryl, or —$C_5$-$C_{10}$-arylalkyl, wherein (a) one or more of the carbon atoms in the alkyl, alkenyl, alkynyl, aryl or arylalkyl group is each independently optionally replaced with a nitrogen, sulfur or oxygen atom, and (b) the alkyl, alkenyl, alkynyl, aryl or arylalkyl is optionally substituted with an oxygen, a —$C_1$-$C_3$-alkyl, or a —$C_5$-$C_7$-aryl;

$R^5$ is one or more hydrogen, hydroxy, halogen, cyano, alkyloxy, nitro, $NH_2$, $NHCOR^4$, $NHSO_2R^4$, $CONHR^4$, $COOR^4$, optionally substituted aliphatic, alicyclic, heteroaliphatic, heterocyclic, aromatic, or heteroaromatic; and $R^7$ is hydrogen, —$C_1$-$C_6$-alkyl, —$C_2$-$C_6$-alkenyl, —$C_2$-$C_6$-alkynyl, —$C_5$-$C_7$-aryl, or —$C_5$-$C_{10}$-arylalkyl, wherein (a) one or more of the carbon atoms in the alkyl, alkenyl, alkynyl, aryl or arylalkyl group is each independently optionally replaced with a nitrogen, sulfur or oxygen atom, and (b) the alkyl, alkenyl, alkynyl, aryl or arylalkyl is optionally substituted with a halogen, a —$C_1$-$C_3$-alkyl, a —$C_5$-$C_7$-aryl, or —$NR^4R^6$ or —$OR^4$;

or an isomer, enantiomer, racemate, prodrug, active metabolite, metal chelate, or a pharmaceutically-acceptable derivative or salt form of any of the foregoing.

In certain embodiments, $R^1$ is chloro, nitro or cyano. In other embodiments $R^2$ is hydroxy. In other embodiments, $R^3$ can be alkyl or aralkyl.

In certain embodiments, $R^1$ is chloro and $R^2$ is hydroxy. In other embodiments, $R^5$ is one or more methoxy, hydroxy, halo, or dimethylamino groups. In further embodiments, $R^3$ is an optionally substituted alkyl or aralkyl group.

Non-limiting examples of such compounds include N-[(5-chloro-8-hydroxyquinolin-7-yl)-(3,4-dimethoxyphenyl)methyl]propanamide, N-[(5-chloro-8-hydroxyquinolin-7-yl)-(4-methoxyphenyl)methyl]propanamide, N-[(5-chloro-8-hydroxyquinolin-7-yl)-tolyl]-3-phenylpropanamide, N-[(5-chloro-8-hydroxyquinolin-7-yl)-(3-methoxyphenyl)methyl]-3-phenylpropanamide, N-[(5-chloro-8-hydroxyquinolin-7-yl)-(4-dimethylaminophenyl)methyl]-3-phenylpropanamide, N-[(5-chloro-8-hydroxyquinolin-7-yl)-(4-chlorophenyl)methyl]-3-phenylpropanamide, N-[(5-chloro-8-hydroxyquinolin-7-yl)-(3-chlorophenyl)methyl]-3-phenylpropanamide, N-[(5-chloro-8-hydroxyquinolin-7-yl)-(2-chlorophenyl)methyl]-3-phenylpropanamide, N-[(5-chloro-8-hydroxyquinolin-7-yl)-(3,4-dimethoxyphenyl)methyl]-3-phenylpropanamide, N-[(5-chloro-8-hydroxyquinolin-7-yl)-(2,4-dimethoxyphenyl)methyl]-3-phenylpropanamide, N-[(5-chloro-8-hydroxyquinolin-7-yl)-(3,4,5-trimethoxyphenyl)methyl]-3-phenylpropanamide, N-[(5-chloro-8-hydroxyquinolin-7-yl)-(2-bromophenyl)methyl]-3-phenylpropanamide, N-[(5-chloro-8-hydroxyquinolin-7-yl)-p-tolyl-methyl]-3-phenylpropanamide, N-[(5-chloro-8-hydroxyquinolin-7-yl)-(2-hydroxyphenyl)methyl]-3-phenylpropanamide, N-[(5-chloro-8-hydroxyquinolin-7-yl)-(4-methoxyphenyl)methyl]-3-phenylpropanamide, N-[(8-Hydroxy-5-nitro-quinolin-7-yl)-p-tolyl-methyl]-propionamide, N-[{8-hydroxy-5-nitro-7-quinolinyl}(4-methylphenyl)methyl]acetamide, and N-[(8-hydroxyquinolin-7-yl)-(2-methoxyphenyl)methyl]pentanamide.

In a further embodiment, the foregoing subject can be at risk for developing Friedreich's ataxia.

In another embodiment, a method is provided for treating a subject having a disease or condition or at risk for developing a disease or dysfunction characterized by mitochondrial dysfunction, iron accumulation or increased cellular oxidative stress, comprising administering to the subject an effective amount of a compound of formula (I) or a pharmaceutical composition thereof:

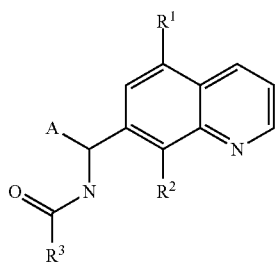

I wherein A is an optionally substituted aliphatic, alicyclic, heteroaliphatic, heterocyclic, aromatic, or heteroaromatic;
$R^1$ is hydrogen, hydroxy, halogen, cyano, alkyloxy, nitro, $NH_2$, $NHCOR^4$, $NHSO_2R^4$, $CONHR^4$, $COOR^4$, or an optionally substituted aliphatic, alicyclic, heteroaliphatic, heterocyclic, aromatic, or heteroaromatic;
$R^2$ is —OR, wherein R is —$C_1$-$C_6$-alkyl, —$C_2$-$C_6$-alkenyl, —$C_2$-$C_6$-alkynyl, —$SO_2NR^4R^6$, —$SO_2R^7$, —$COR^7$, —$COOR^7$ or —$CONR^4R^6$, wherein (a) one or more of the carbon atoms in the alkyl, alkenyl or alkynyl group is each independently optionally replaced with a nitrogen, sulfur or oxygen atom, and (b) the alkyl, alkenyl or alkynyl group is optionally substituted with a —$C_1$-$C_3$-alkyl;
$R^3$ is an optionally substituted aliphatic, alicyclic, heteroaliphatic, heterocyclic, aromatic, or heteroaromatic; and
$R^4$ and $R^6$ are each independently hydrogen, —$C_1$-$C_6$-alkyl, —$C_2$-$C_6$-alkenyl, —$C_2$-$C_6$-alkynyl, —$COR^7$, —$C_5$-$C_7$-aryl, or —$C_5$-$C_{10}$-arylalkyl, wherein (a) one or more of the carbon atoms in the alkyl, alkenyl, alkynyl, aryl or arylalkyl group is each independently optionally replaced with a nitrogen, sulfur or oxygen atom, and (b) the alkyl, alkenyl, alkynyl, aryl or arylalkyl is optionally substituted with an oxygen, a —$C_1$-$C_3$-alkyl, or a —$C_5$-$C_7$-aryl; and
$R^7$ is hydrogen, —$C_1$-$C_6$-alkyl, —$C_2$-$C_6$-alkenyl, —$C_2$-$C_6$-alkynyl, —$C_5$-$C_7$-aryl, or —$C_5$-$C_{10}$-arylalkyl, wherein (a) one or more of the carbon atoms in the alkyl, alkenyl, alkynyl, aryl or arylalkyl group is each independently optionally replaced with a nitrogen, sulfur or oxygen atom, and (b) the alkyl, alkenyl, alkynyl, aryl or arylalkyl is optionally substituted with a halogen, a —$C_1$-$C_3$-alkyl, a —$C_5$-$C_7$-aryl, or —$NR^4R^6$ or —$OR^4$;
or an isomer, stereoisomer, racemate, prodrug, active metabolite, metal chelate, or a pharmaceutically-acceptable derivative or salt form of any of the foregoing.

In certain embodiments, $R^1$ is chloro, nitro or cyano. In other embodiments $R^2$ is hydroxy. In other embodiments, A is a substituted aryl group or an optionally substituted furyl group. In further embodiments, $R^3$ is an optionally substituted alkyl or aralkyl group.

In certain embodiments, the compound of formula (I) has the structure of formula (II):

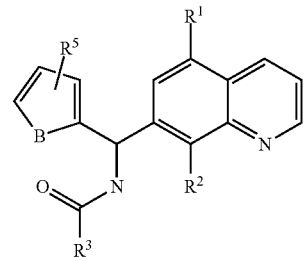

II wherein B is O, N or S;
$R^1$ is hydrogen, hydroxy, halogen, cyano, alkyloxy, nitro, $NH_2$, $NHCOR^4$, $NHSO_2R^4$, $CONHR^4$, $COOR^4$, or an optionally substituted aliphatic, alicyclic, heteroaliphatic, heterocyclic, aromatic, or heteroaromatic;
$R^2$ is —OR, wherein R is —$C_1$-$C_6$-alkyl, —$C_2$-$C_6$-alkenyl, —$C_2$-$C_6$-alkynyl, —$SO_2NR^4R^6$, —$SO_2R^7$, —$COR^7$, —$COOR^7$ or —$CONR^4R^6$, wherein (a) one or more of the carbon atoms in the alkyl, alkenyl or alkynyl group is each independently optionally replaced with a nitrogen, sulfur or oxygen atom, and (b) the alkyl, alkenyl or alkynyl group is optionally substituted with a —$C_1$-$C_3$-alkyl;
$R^3$ is an optionally substituted aliphatic, alicyclic, heteroaliphatic, heterocyclic, aromatic, or hetero aromatic;
$R^4$ and $R^6$ are each independently hydrogen, —$C_1$-$C_6$-alkyl, —$C_2$-$C_6$-alkenyl, —$C_2$-$C_6$-alkynyl, —$COR^7$, —$C_5$-$C_7$-aryl, or —$C_5$-$C_{10}$-arylalkyl, wherein (a) one or more of the carbon atoms in the alkyl, alkenyl, alkynyl, aryl or arylalkyl group is each independently optionally replaced with a nitrogen, sulfur or oxygen atom, and (b) the alkyl, alkenyl, alkynyl, aryl or arylalkyl is optionally substituted with an oxygen, a —$C_1$-$C_3$-alkyl, or a —$C_5$-$C_7$-aryl;
$R^5$ is one or more hydrogen, hydroxy, halogen, cyano, alkyloxy, nitro, $NH_2$, $NHCOR^4$, $NHSO_2R^4$, $CONHR^4$, $COOR^4$, optionally substituted aliphatic, alicyclic, heteroaliphatic, heterocyclic, aromatic, or heteroaromatic; and
$R^7$ is hydrogen, —$C_1$-$C_6$-alkyl, —$C_2$-$C_6$-alkenyl, —$C_2$-$C_6$-alkynyl, —$C_5$-$C_7$-aryl, or —$C_5$-$C_{10}$-arylalkyl, wherein (a) one or more of the carbon atoms in the alkyl, alkenyl, alkynyl, aryl or arylalkyl group is each independently optionally replaced with a nitrogen, sulfur or oxygen atom, and (b) the alkyl, alkenyl, alkynyl, aryl or arylalkyl is optionally substituted with a halogen, a —$C_1$-$C_3$-alkyl, a —$C_5$-$C_7$-aryl, or —$NR^4R^6$ or —$OR^4$;
or an isomer, enantiomer, racemate, prodrug, active metabolite, metal chelate, or a pharmaceutically-acceptable derivative or salt form of any of the foregoing.

In certain embodiments, $R^1$ is chloro, nitro or cyano. In other embodiments $R^2$ is hydroxy. In other embodiments, $R^3$ can be alkyl or aralkyl.

In certain embodiments, $R^1$ is chloro and $R^2$ is hydroxy. In other embodiments, B is O. In further embodiments, $R^3$ is an optionally substituted alkyl or aralkyl group.

Non-limiting examples of such compounds include N-[(5-chloro-8-hydroxyquinolin-7-yl)-thiophen-2-ylmethyl]-3- phenylpropanamide, N-[(5-chloro-8-hydroxyquinolin-7-yl)-thiophen-2-ylmethyl]pentanamide, N-[(5-chloro-8-hydroxyquinolin-7-yl)-thiophen-2-ylmethyl]propanamide, N-[(5-chloro-8-hydroxyquinolin-7-yl)-thiophen-2-ylmethyl]-2-methylpropanamide, N-[(5-chloro-8-hydroxyquinolin-7-yl)-thiophen-2-ylmethyl]butanamide, N-[(5-chloro-8-hydroxyquinolin-7-yl)-thiophen-2-ylmethyl]acetamide, N-[(8-hydroxy-5-nitroquinolin-7-yl)-thiophen-2-ylmethyl]butanamide, N-[(8-hydroxy-5-nitro-quinolin-7-yl)-thiophen-2-yl-methyl]-acetamide, N-[(8-hydroxy-5-nitro-quinolin-7-yl)-thiophen-2-yl-methyl]-propionamide, N-[2-furyl(8-hydroxy-5-nitro-7-quinolinyl)methyl]butanamide, N-[(8-hydroxyquinolin-7-yl)-thiophen-2-ylmethyl]-3-phenylpropanamide, N-[(5-chloro-8-hydroxyquinolin-7-yl)-furan-2-ylmethyl]-3-phenylpropanamide, N-[(5-chloro-8-hydroxyquinolin-7-yl)-furan-2-ylmethyl]propanamide, and N-[(5-chloro-8-hydroxyquinolin-7-yl)-furan-2-ylmethyl]pentanamide.

In certain other embodiments, compound (I) has the structure of formula (III)

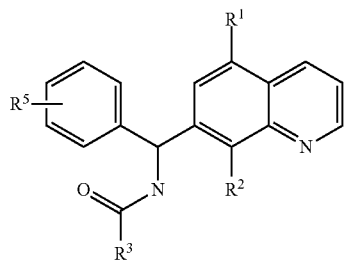

III wherein $R^1$ is hydrogen, hydroxy, halogen, cyano, alkyloxy, nitro, $NH_2$, $NHCOR^4$, $NHSO_2R^4$, $CONHR^4$, $COOR^4$, or an optionally substituted aliphatic, alicyclic, heteroaliphatic, heterocyclic, aromatic, or heteroaromatic;

$R^2$ is —OR, wherein R is —$C_1$-$C_6$-alkyl, —$C_2$-$C_6$-alkenyl, —$C_2$-$C_6$-alkynyl, —$SO_2NR^4R^6$, —$SO_2R^7$, —$COR^7$, —$COOR^7$ or —$CONR^4R^6$, wherein (a) one or more of the carbon atoms in the alkyl, alkenyl or alkynyl group is each independently optionally replaced with a nitrogen, sulfur or oxygen atom, and (b) the alkyl, alkenyl or alkynyl group is optionally substituted with a —$C_1$-$C_3$-alkyl;

$R^3$ is an optionally substituted aliphatic, alicyclic, heteroaliphatic, heterocyclic, aromatic, or hetero aromatic;

$R^4$ and $R^6$ are each independently hydrogen, —$C_1$-$C_6$-alkyl, —$C_2$-$C_6$-alkenyl, —$C_2$-$C_6$-alkynyl, —$COR^7$, —$C_5$-$C_7$-aryl, or —$C_5$-$C_{10}$-arylalkyl, wherein (a) one or more of the carbon atoms in the alkyl, alkenyl, alkynyl, aryl or arylalkyl group is each independently optionally replaced with a nitrogen, sulfur or oxygen atom, and (b) the alkyl, alkenyl, alkynyl, aryl or arylalkyl is optionally substituted with an oxygen, a —$C_1$-$C_3$-alkyl, or a —$C_5$-$C_7$-aryl;

$R^5$ is one or more hydrogen, hydroxy, halogen, cyano, alkyloxy, nitro, $NH_2$, $NHCOR^4$, $NHSO_2R^4$, $CONHR^4$, $COOR^4$, optionally substituted aliphatic, alicyclic, heteroaliphatic, heterocyclic, aromatic, or heteroaromatic; and $R^7$ is hydrogen, —$C_1$-$C_6$-alkyl, —$C_2$-$C_6$-alkenyl, —$C_2$-$C_6$-alkynyl, —$C_5$-$C_7$-aryl, or —$C_5$-$C_{10}$-arylalkyl, wherein (a) one or more of the carbon atoms in the alkyl, alkenyl, alkynyl, aryl or arylalkyl group is each independently optionally replaced with a nitrogen, sulfur or oxygen atom, and (b) the alkyl, alkenyl, alkynyl, aryl or arylalkyl is optionally substituted with a halogen, a —$C_1$-$C_3$-alkyl, a —$C_5$-$C_7$-aryl, or —$NR^4R^6$ or —$OR^4$;

or an isomer, enantiomer, racemate, prodrug, active metabolite, metal chelate, or a pharmaceutically-acceptable derivative or salt form of any of the foregoing.

In certain embodiments, $R^1$ is chloro, nitro or cyano. In other embodiments $R^2$ is hydroxy. In other embodiments, $R^3$ can be alkyl or aralkyl.

In certain embodiments, $R^1$ is chloro and $R^2$ is hydroxy. In other embodiments, $R^5$ is one or more methoxy, hydroxy, halo, or dimethylamino groups. In further embodiments, $R^3$ is an optionally substituted alkyl or aralkyl group.

Non-limiting examples of such compounds include N-[(5-chloro-8-hydroxyquinolin-7-yl)-(3,4-dimethoxyphenyl)methyl]propanamide, N-[(5-chloro-8-hydroxyquinolin-7-yl)-(4-methoxyphenyl)methyl]propanamide, N-[(5-chloro-8-hydroxyquinolin-7-yl)-tolyl]-3-phenylpropanamide, N-[(5-chloro-8-hydroxyquinolin-7-yl)-(3-methoxyphenyl)methyl]-3-phenylpropanamide, N-[(5-chloro-8-hydroxyquinolin-7-yl)-(4-dimethylaminophenyl)methyl]-3-phenylpropanamide, N-[(5-chloro-8-hydroxyquinolin-7-yl)-(4-chlorophenyl)methyl]-3-phenylpropanamide, N-[(5-chloro-8-hydroxyquinolin-7-yl)-(3-chlorophenyl)methyl]-3-phenylpropanamide, N-[(5-chloro-8-hydroxyquinolin-7-yl)-(2-chlorophenyl)methyl]-3-phenylpropanamide, N-[(5-chloro-8-hydroxyquinolin-7-yl)-(3,4-dimethoxyphenyl)methyl]-3-phenylpropanamide, N-[(5-chloro-8-hydroxyquinolin-7-yl)-(2,4-dimethoxyphenyl)methyl]-3-phenylpropanamide, N-[(5-chloro-8-hydroxyquinolin-7-yl)-(3,4,5-trimethoxyphenyl)methyl]-3-phenylpropanamide, N-[(5-chloro-8-hydroxyquinolin-7-yl)-(2-bromophenyl)methyl]-3-phenylpropanamide, N-[(5-chloro-8-hydroxyquinolin-7-yl)-p-tolyl-methyl]-3-phenylpropanamide, N-[(5-chloro-8-hydroxyquinolin-7-yl)-(2-hydroxyphenyl)methyl]-3-phenylpropanamide, N-[(5-chloro-8-hydroxyquinolin-7-yl)-(4-methoxyphenyl)methyl]-3-phenylpropanamide, N-[(8-Hydroxy-5-nitro-quinolin-7-yl)-p-tolyl-methyl]-propionamide, N-[{8-hydroxy-5-nitro-7-quinolinyl}(4-methylphenyl)methyl]acetamide, and N-[(8-hydroxyquinolin-7-yl)-(2-methoxyphenyl)methyl]pentanamide.

In other embodiments, methods are provided for treating a subject having or at risk for developing a neurodegenerative disease, neurodegeneration with brain iron accumulation (NBIA), Friedreich's ataxia, Parkinson's disease, Alzheimer's disease, a mitochondrial encephalopathy, normal aging, hemochromatosis, aceruloplasminemia, thalassemia, attention deficit hyperactivity disorder (ADHD), Tourette's syndrome, diabetes, or age-related macular degeneration, comprising administering to the subject an effective amount of a compound of formula (I) or a pharmaceutical composition thereof:

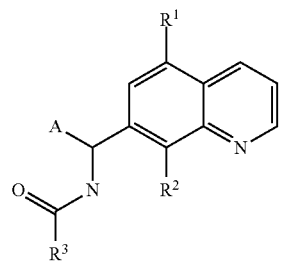

I wherein A is an optionally substituted aliphatic, alicyclic, heteroaliphatic, heterocyclic, aromatic, or heteroaromatic;

$R^1$ is hydrogen, hydroxy, halogen, cyano, alkyloxy, nitro, $NH_2$, $NHCOR^4$, $NHSO_2R^4$, $CONHR^4$, $COOR^4$, or an optionally substituted aliphatic, alicyclic, heteroaliphatic, heterocyclic, aromatic, or heteroaromatic;

R² is —OR, wherein R is —$C_1$-$C_6$-alkyl, —$C_2$-$C_6$-alkenyl, —$C_2$-$C_6$-alkynyl, —$SO_2NR^4R^6$, —$SO_2R^7$, —$COR^7$, —$COOR^7$ or —$CONR^4R^6$, wherein (a) one or more of the carbon atoms in the alkyl, alkenyl or alkynyl group is each independently optionally replaced with a nitrogen, sulfur or oxygen atom, and (b) the alkyl, alkenyl or alkynyl group is optionally substituted with a —$C_1$-$C_3$-alkyl;

R³ is an optionally substituted aliphatic, alicyclic, heteroaliphatic, heterocyclic, aromatic, or heteroaromatic; and R⁴ and R⁶ are each independently hydrogen, —$C_1$-$C_6$-alkyl, —$C_2$-$C_6$-alkenyl, —$C_2$-$C_6$-alkynyl, —$COR^7$, —$C_5$-$C_7$-aryl, or —$C_5$-$C_{10}$-arylalkyl, wherein (a) one or more of the carbon atoms in the alkyl, alkenyl, alkynyl, aryl or arylalkyl group is each independently optionally replaced with a nitrogen, sulfur or oxygen atom, and (b) the alkyl, alkenyl, alkynyl, aryl or arylalkyl is optionally substituted with an oxygen, a —$C_1$-$C_3$-alkyl, or a —$C_5$-$C_7$-aryl; and R⁷ is hydrogen, —$C_1$-$C_6$-alkyl, —$C_2$-$C_6$-alkenyl, —$C_2$-$C_6$-alkynyl, —$C_5$-$C_7$-aryl, or —$C_5$-$C_{10}$-arylalkyl, wherein (a) one or more of the carbon atoms in the alkyl, alkenyl, alkynyl, aryl or arylalkyl group is each independently optionally replaced with a nitrogen, sulfur or oxygen atom, and (b) the alkyl, alkenyl, alkynyl, aryl or arylalkyl is optionally substituted with a halogen, a —$C_1$-$C_3$-alkyl, a —$C_5$-$C_7$-aryl, or —$NR^4R^6$ or —$OR^4$;

or an isomer, stereoisomer, racemate, prodrug, active metabolite, metal chelate, or a pharmaceutically-acceptable derivative or salt form of any of the foregoing.

In certain embodiments, R¹ is chloro, nitro or cyano. In other embodiments R² is hydroxy. In other embodiments, A is a substituted aryl group or an optionally substituted furyl group. In further embodiments, R³ is an optionally substituted alkyl or aralkyl group.

In certain embodiments, the compound of formula (I) has the structure of formula (II):

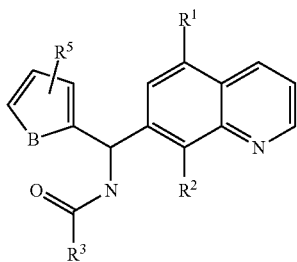

II wherein B is O, N or S;

R¹ is hydrogen, hydroxy, halogen, cyano, alkyloxy, nitro, $NH_2$, $NHCOR^4$, $NHSO_2R^4$, $CONHR^4$, $COOR^4$, or an optionally substituted aliphatic, alicyclic, heteroaliphatic, heterocyclic, aromatic, or heteroaromatic;

R² is —OR, wherein R is —$C_1$-$C_6$-alkyl, —$C_2$-$C_6$-alkenyl, —$C_2$-$C_6$-alkynyl, —$SO_2NR^4R^6$, —$SO_2R^7$, —$COR^7$, —$COOR^7$ or —$CONR^4R^6$, wherein (a) one or more of the carbon atoms in the alkyl, alkenyl or alkynyl group is each independently optionally replaced with a nitrogen, sulfur or oxygen atom, and (b) the alkyl, alkenyl or alkynyl group is optionally substituted with a —$C_1$-$C_3$-alkyl;

R³ is an optionally substituted aliphatic, alicyclic, heteroaliphatic, heterocyclic, aromatic, or hetero aromatic;

R⁴ and R⁶ are each independently hydrogen, —$C_1$-$C_6$-alkyl, —$C_2$-$C_6$-alkenyl, —$C_2$-$C_6$-alkynyl, —$COR^7$, —$C_5$-$C_7$-aryl, or —$C_5$-$C_{10}$-arylalkyl, wherein (a) one or more of the carbon atoms in the alkyl, alkenyl, alkynyl, aryl or arylalkyl group is each independently optionally replaced with a nitrogen, sulfur or oxygen atom, and (b) the alkyl, alkenyl, alkynyl, aryl or arylalkyl is optionally substituted with an oxygen, a —$C_1$-$C_3$-alkyl, or a —$C_5$-$C_7$-aryl;

R⁵ is one or more hydrogen, hydroxy, halogen, cyano, alkyloxy, nitro, $NH_2$, $NHCOR^4$, $NHSO_2R^4$, $CONHR^4$, $COOR^4$, optionally substituted aliphatic, alicyclic, heteroaliphatic, heterocyclic, aromatic, or heteroaromatic; and R⁷ is hydrogen, —$C_1$-$C_6$-alkyl, —$C_2$-$C_6$-alkenyl, —$C_2$-$C_6$-alkynyl, —$C_5$-$C_7$-aryl, or —$C_5$-$C_{10}$-arylalkyl, wherein (a) one or more of the carbon atoms in the alkyl, alkenyl, alkynyl, aryl or arylalkyl group is each independently optionally replaced with a nitrogen, sulfur or oxygen atom, and (b) the alkyl, alkenyl, alkynyl, aryl or arylalkyl is optionally substituted with a halogen, a —$C_1$-$C_3$-alkyl, a —$C_5$-$C_7$-aryl, or —$NR^4R^6$ or —$OR^4$;

or an isomer, enantiomer, racemate, prodrug, active metabolite, metal chelate, or a pharmaceutically-acceptable derivative or salt form of any of the foregoing.

In certain embodiments, R¹ is chloro, nitro or cyano. In other embodiments R² is hydroxy. In other embodiments, R³ can be alkyl or aralkyl.

In certain embodiments, R¹ is chloro and R² is hydroxy. In other embodiments, B is O. In further embodiments, R³ is an optionally substituted alkyl or aralkyl group.

Non-limiting examples of such compounds include N-[(5-chloro-8-hydroxyquinolin-7-yl)-thiophen-2-ylmethyl]-3-phenylpropanamide, N-[(5-chloro-8-hydroxyquinolin-7-yl)-thiophen-2-ylmethyl]pentanamide, N-[(5-chloro-8-hydroxyquinolin-7-yl)-thiophen-2-ylmethyl]propanamide, N-[(5-chloro-8-hydroxyquinolin-7-yl)-thiophen-2-ylmethyl]-2-methylpropanamide, N-[(5-chloro-8-hydroxyquinolin-7-yl)-thiophen-2-ylmethyl]butanamide, N-[(5-chloro-8-hydroxyquinolin-7-yl)-thiophen-2-ylmethyl] acetamide, N-[(8-hydroxy-5-nitroquinolin-7-yl)-thiophen-2-ylmethyl]butanamide, N-[(8-hydroxy-5-nitro-quinolin-7-yl)-thiophen-2-yl-methyl]-acetamide, N-[(8-hydroxy-5-nitro-quinolin-7-yl)-thiophen-2-yl-methyl]-propionamide, N-[2-furyl(8-hydroxy-5-nitro-7-quinolinyl)methyl]butanamide, N-[(8-hydroxyquinolin-7-yl)-thiophen-2-ylmethyl]-3-phenylpropanamide, N-[(5-chloro-8-hydroxyquinolin-7-yl)-furan-2-ylmethyl]-3-phenylpropanamide, N-[(5-chloro-8-hydroxyquinolin-7-yl)-furan-2-ylmethyl]propanamide, and N-[(5-chloro-8-hydroxyquinolin-7-yl)-furan-2-ylmethyl]pentanamide.

In certain other embodiments, compound (I) has the structure of formula (III)

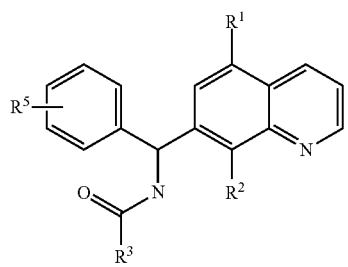

III wherein R¹ is hydrogen, hydroxy, halogen, cyano, alkyloxy, nitro, $NH_2$, $NHCOR^4$, $NHSO_2R^4$, $CONHR^4$, COOR⁴, or an optionally substituted aliphatic, alicyclic, heteroaliphatic, heterocyclic, aromatic, or heteroaromatic;

R² is —OR, wherein R is —$C_1$-$C_6$-alkyl, —$C_2$-$C_6$-alkenyl, —$C_2$-$C_6$-alkynyl, —SO₂NR⁴R⁶, —SO₂R⁷, —COR⁷, —COOR⁷ or —CONR⁴R⁶, wherein (a) one or more of the carbon atoms in the alkyl, alkenyl or alkynyl group is each independently optionally replaced with a nitrogen, sulfur or oxygen atom, and (b) the alkyl, alkenyl or alkynyl group is optionally substituted with a —$C_1$-$C_3$-alkyl;

R³ is an optionally substituted aliphatic, alicyclic, heteroaliphatic, heterocyclic, aromatic, or hetero aromatic;

R⁴ and R⁶ are each independently hydrogen, —$C_1$-$C_6$-alkyl, —$C_2$-$C_6$-alkenyl, —$C_2$-$C_6$-alkynyl, —COR⁷, —$C_5$-$C_7$-aryl, or —$C_5$-$C_{10}$-arylalkyl, wherein (a) one or more of the carbon atoms in the alkyl, alkenyl, alkynyl, aryl or arylalkyl group is each independently optionally replaced with a nitrogen, sulfur or oxygen atom, and (b) the alkyl, alkenyl, alkynyl, aryl or arylalkyl is optionally substituted with an oxygen, a —$C_1$-$C_3$-alkyl, or a —$C_5$-$C_7$-aryl;

R⁵ is one or more hydrogen, hydroxy, halogen, cyano, alkyloxy, nitro, NH₂, NHCOR⁴, NHSO₂R⁴, CONHR⁴, COOR⁴, optionally substituted aliphatic, alicyclic, heteroaliphatic, heterocyclic, aromatic, or heteroaromatic; and R⁷ is hydrogen, —$C_1$-$C_6$-alkyl, —$C_2$-$C_6$-alkenyl, —$C_2$-$C_6$-alkynyl, —$C_5$-$C_7$-aryl, or —$C_5$-$C_{10}$-arylalkyl, wherein (a) one or more of the carbon atoms in the alkyl, alkenyl, alkynyl, aryl or arylalkyl group is each independently optionally replaced with a nitrogen, sulfur or oxygen atom, and (b) the alkyl, alkenyl, alkynyl, aryl or arylalkyl is optionally substituted with a halogen, a —$C_1$-$C_3$-alkyl, a —$C_5$-$C_7$-aryl, or —NR⁴R⁶ or —OR⁴;

or an isomer, enantiomer, racemate, prodrug, active metabolite, metal chelate, or a pharmaceutically-acceptable derivative or salt form of any of the foregoing.

In certain embodiments, R¹ is chloro, nitro or cyano. In other embodiments R² is hydroxy. In other embodiments, R³ can be alkyl or aralkyl.

In certain embodiments, R¹ is chloro and R² is hydroxy. In other embodiments, R⁵ is one or more methoxy, hydroxy, halo, or dimethylamino groups. In further embodiments, R³ is an optionally substituted alkyl or aralkyl group.

Non-limiting examples of such compounds include N-[(5-chloro-8-hydroxyquinolin-7-yl)-(3,4-dimethoxyphenyl)methyl]propanamide, N-[(5-chloro-8-hydroxyquinolin-7-yl)-(4-methoxyphenyl)methyl]propanamide, N-[(5-chloro-8-hydroxyquinolin-7-yl)-tolyl]-3-phenylpropanamide, N-[(5-chloro-8-hydroxyquinolin-7-yl)-(3-methoxyphenyl)methyl]-3-phenylpropanamide, N-[(5-chloro-8-hydroxyquinolin-7-yl)-(4-dimethylaminophenyl)methyl]-3-phenylpropanamide, N-[(5-chloro-8-hydroxyquinolin-7-yl)-(4-chlorophenyl)methyl]-3-phenylpropanamide, N-[(5-chloro-8-hydroxyquinolin-7-yl)-(3-chlorophenyl)methyl]-3-phenylpropanamide, N-[(5-chloro-8-hydroxyquinolin-7-yl)-(2-chlorophenyl)methyl]-3-phenylpropanamide, N-[(5-chloro-8-hydroxyquinolin-7-yl)-(3,4-dimethoxyphenyl)methyl]-3-phenylpropanamide, N-[(5-chloro-8-hydroxyquinolin-7-yl)-(2,4-dimethoxyphenyl)methyl]-3-phenylpropanamide, N-[(5-chloro-8-hydroxyquinolin-7-yl)-(3,4,5-trimethoxyphenyl)methyl]-3-phenylpropanamide, N-[(5-chloro-8-hydroxyquinolin-7-yl)-(2-bromophenyl)methyl]-3-phenylpropanamide, N-[(5-chloro-8-hydroxyquinolin-7-yl)-p-tolyl-methyl]-3-phenylpropanamide, N-[(5-chloro-8-hydroxyquinolin-7-yl)-(2-hydroxyphenyl)methyl]-3-phenylpropanamide, N-[(5-chloro-8-hydroxyquinolin-7-yl)-(4-methoxyphenyl)methyl]-3-phenylpropanamide, N-[(8-Hydroxy-5-nitro-quinolin-7-yl)-p-tolyl-methyl]-propionamide, N-[{8-hydroxy-5-nitro-7-quinolinyl}(4-methylphenyl)methyl]acetamide, and N-[(8-hydroxyquinolin-7-yl)-(2-methoxyphenyl)methyl]pentanamide.

In another embodiment, a method is provided for identifying a step in mitochondrial function or cellular respiration upstream from or regulated by frataxin activity or the phenotype thereof, and for identifying candidate activity modulators of such step. In one embodiment, the method comprises determining the effect on mitochondrial function or cellular respiration of at least one candidate modulator in cells that are frataxin deficient, frataxin-mutated, or in frataxin knockout cells, in the presence and absence of a compound of formula (I), (II) or (III) described herein above.

In a further embodiment, the effect of the at least one candidate modulator on mitochondrial function, iron homeostasis, resistance to oxidants and/or added iron, or cellular respiration in the presence and absence of the compound of formula (I), (II) or (III) is correlated with the relationship of the step to that of frataxin activity, its role in regulation thereof, and identification of a modulator thereof. In a further embodiment, the at least one candidate modulator of the step is a compound that modulates activity of the step, or a mutation that modulates the step, or the combination thereof. In another embodiment, the mutation inhibits the step and the compound is a candidate activator of or phenotypic substitute for the step. In another embodiment, the frataxin deficient, frataxin-mutated, or frataxin knockout cells are yeast cells or mammalian cells, and in further embodiments, the yeast cells have at least one gene encoding a protein catalyzing or regulating the step knocked out or regulated by an inducible promoter; or the yeast cells also have the frataxin gene knocked out or regulated by an inducible promoter. In another embodiment, the compound has formula (II) or formula (III) as described hereinabove, or any embodiment thereof.

In another embodiment, a method is provided for identifying cells, tissues, or cells or tissues from a subject that may have a defect in mitochondrial function, cellular respiration upstream from or regulated by frataxin activity or the phenotype thereof, comprising determining the effect on mitochondrial function or cellular respiration in said cells or tissues by a compound of formula (I), (II) or (III) as described hereinabove.

In another embodiment, compounds and pharmaceutical compositions of such compounds useful for the purposes herein are provided having the structure of formula (I):

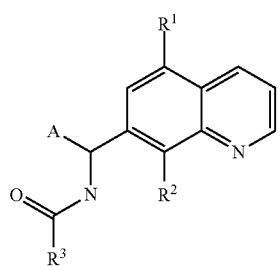

I wherein A is an optionally substituted aliphatic, alicyclic, heteroaliphatic, heterocyclic, aromatic, or heteroaromatic;

R¹ is hydrogen, hydroxy, halogen, cyano, alkyloxy, nitro, NH₂, NHCOR⁴, NHSO₂R⁴, CONHR⁴, COOR⁴, or an optionally substituted aliphatic, alicyclic, heteroaliphatic, heterocyclic, aromatic, or heteroaromatic;

$R^2$ is —OR, wherein R is —$C_1$-$C_6$-alkyl, —$C_2$-$C_6$-alkenyl, —$C_2$-$C_6$-alkynyl, —$SO_2NR^4R^6$, —$SO_2R^7$, —$COR^7$, —$COOR^7$ or —$CONR^4R^6$, wherein (a) one or more of the carbon atoms in the alkyl, alkenyl or alkynyl group is each independently optionally replaced with a nitrogen, sulfur or oxygen atom, and (b) the alkyl, alkenyl or alkynyl group is optionally substituted with a —$C_1$-$C_3$-alkyl;

$R^3$ is an optionally substituted aliphatic, alicyclic, heteroaliphatic, heterocyclic, aromatic, or heteroaromatic; and $R^4$ and $R^6$ are each independently hydrogen, —$C_1$-$C_6$-alkyl, —$C_2$-$C_6$-alkenyl, —$C_2$-$C_6$-alkynyl, —$COR^7$, —$C_5$-$C_7$-aryl, or —$C_5$-$C_{10}$-arylalkyl, wherein (a) one or more of the carbon atoms in the alkyl, alkenyl, alkynyl, aryl or arylalkyl group is each independently optionally replaced with a nitrogen, sulfur or oxygen atom, and (b) the alkyl, alkenyl, alkynyl, aryl or arylalkyl is optionally substituted with an oxygen, a —$C_1$-$C_3$-alkyl, or a —$C_5$-$C_7$-aryl; and $R^7$ is hydrogen, —$C_1$-$C_6$-alkyl, —$C_2$-$C_6$-alkenyl, —$C_2$-$C_6$-alkynyl, —$C_5$-$C_7$-aryl, or —$C_5$-$C_{10}$-arylalkyl, wherein (a) one or more of the carbon atoms in the alkyl, alkenyl, alkynyl, aryl or arylalkyl group is each independently optionally replaced with a nitrogen, sulfur or oxygen atom, and (b) the alkyl, alkenyl, alkynyl, aryl or arylalkyl is optionally substituted with a halogen, a —$C_1$-$C_3$-alkyl, a —$C_5$-$C_7$-aryl, or —$NR^4R^6$ or —$OR^4$;

or an isomer, stereoisomer, racemate, prodrug, active metabolite, metal chelate, or a pharmaceutically-acceptable derivative or salt form of any of the foregoing.

In certain embodiments, $R^1$ is chloro, nitro or cyano. In other embodiments $R^2$ is hydroxy. In other embodiments, A is a substituted aryl group or an optionally substituted furyl group. In further embodiments, $R^3$ is an optionally substituted alkyl or aralkyl group.

In certain embodiments, the compound of formula (I) has the structure of formula (II):

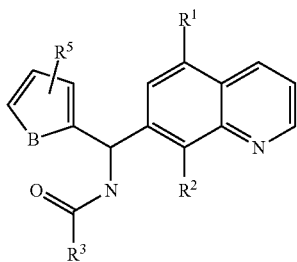

II wherein B is O, N or S;

$R^1$ is hydrogen, hydroxy, halogen, cyano, alkyloxy, nitro, $NH_2$, $NHCOR^4$, $NHSO_2R^4$, $CONHR^4$, $COOR^4$, or an optionally substituted aliphatic, alicyclic, heteroaliphatic, heterocyclic, aromatic, or heteroaromatic;

$R^2$ is —OR, wherein R is —$C_1$-$C_6$-alkyl, —$C_2$-$C_6$-alkenyl, —$C_2$-$C_6$-alkynyl, —$SO_2NR^4R^6$, —$SO_2R^7$, —$COR^7$, —$COOR^7$ or —$CONR^4R^6$, wherein (a) one or more of the carbon atoms in the alkyl, alkenyl or alkynyl group is each independently optionally replaced with a nitrogen, sulfur or oxygen atom, and (b) the alkyl, alkenyl or alkynyl group is optionally substituted with a —$C_1$-$C_3$-alkyl;

$R^3$ is an optionally substituted aliphatic, alicyclic, heteroaliphatic, heterocyclic, aromatic, or hetero aromatic;

$R^4$ and $R^6$ are each independently hydrogen, —$C_1$-$C_6$-alkyl, —$C_2$-$C_6$-alkenyl, —$C_2$-$C_6$-alkynyl, —$COR^7$, —$C_5$-$C_7$-aryl, or —$C_5$-$C_{10}$-arylalkyl, wherein (a) one or more of the carbon atoms in the alkyl, alkenyl, alkynyl, aryl or arylalkyl group is each independently optionally replaced with a nitrogen, sulfur or oxygen atom, and (b) the alkyl, alkenyl, alkynyl, aryl or arylalkyl is optionally substituted with an oxygen, a —$C_1$-$C_3$-alkyl, or a —$C_5$-$C_7$-aryl;

$R^5$ is one or more hydrogen, hydroxy, halogen, cyano, alkyloxy, nitro, $NH_2$, $NHCOR^4$, $NHSO_2R^4$, $CONHR^4$, $COOR^4$, optionally substituted aliphatic, alicyclic, heteroaliphatic, heterocyclic, aromatic, or heteroaromatic; and $R^7$ is hydrogen, —$C_1$-$C_6$-alkyl, —$C_2$-$C_6$-alkenyl, —$C_2$-$C_6$-alkynyl, —$C_5$-$C_7$-aryl, or —$C_5$-$C_{10}$-arylalkyl, wherein (a) one or more of the carbon atoms in the alkyl, alkenyl, alkynyl, aryl or arylalkyl group is each independently optionally replaced with a nitrogen, sulfur or oxygen atom, and (b) the alkyl, alkenyl, alkynyl, aryl or arylalkyl is optionally substituted with a halogen, a —$C_1$-$C_3$-alkyl, a —$C_5$-$C_7$-aryl, or —$NR^4R^6$ or —$OR^4$;

or an isomer, enantiomer, racemate, prodrug, active metabolite, metal chelate, or a pharmaceutically-acceptable derivative or salt form of any of the foregoing.

In certain embodiments, $R^1$ is chloro, nitro or cyano. In other embodiments $R^2$ is hydroxy. In other embodiments, B is O. In further embodiments, $R^3$ is an optionally substituted alkyl or aralkyl group.

Non-limiting examples of such compounds include N-[(5-chloro-8-hydroxyquinolin-7-yl)-thiophen-2-ylmethyl]-3-phenylpropanamide, N-[(5-chloro-8-hydroxyquinolin-7-yl)-thiophen-2-ylmethyl]pentanamide, N-[(5-chloro-8-hydroxyquinolin-7-yl)-thiophen-2-ylmethyl]propanamide, N-[(5-chloro-8-hydroxyquinolin-7-yl)-thiophen-2-ylmethyl]-2-methylpropanamide, N-[(5-chloro-8-hydroxyquinolin-7-yl)-thiophen-2-ylmethyl]butanamide, N-[(5-chloro-8-hydroxyquinolin-7-yl)-thiophen-2-ylmethyl] acetamide, N-[(8-hydroxy-5-nitroquinolin-7-yl)-thiophen-2-ylmethyl]butanamide, N-[(8-hydroxy-5-nitro-quinolin-7-yl)-thiophen-2-yl-methyl]-acetamide, N-[(8-hydroxy-5-nitro-quinolin-7-yl)-thiophen-2-yl-methyl]-propionamide, N-[2-furyl(8-hydroxy-5-nitro-7-quinolinyl)methyl]butanamide, N-[(8-hydroxyquinolin-7-yl)-thiophen-2-ylmethyl]-3-phenylpropanamide, N-[(5-chloro-8-hydroxyquinolin-7-yl)-furan-2-ylmethyl]-3-phenylpropanamide, N-[(5-chloro-8-hydroxyquinolin-7-yl)-furan-2-ylmethyl]propanamide, and N-[(5-chloro-8-hydroxyquinolin-7-yl)-furan-2-ylmethyl]pentanamide.

In certain other embodiments, compound (I) has the structure of formula (III)

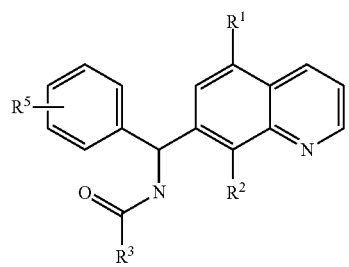

III wherein $R^1$ is hydrogen, hydroxy, halogen, cyano, alkyloxy, nitro, $NH_2$, $NHCOR^4$, $NHSO_2R^4$, $CONHR^4$, COOR$^4$, or an optionally substituted aliphatic, alicyclic, heteroaliphatic, heterocyclic, aromatic, or heteroaromatic;

R$^2$ is —OR, wherein R is —C$_1$-C$_6$-alkyl, —C$_2$-C$_6$-alkenyl, —C$_2$-C$_6$-alkynyl, —SO$_2$NR$^4$R$^6$, —SO$_2$R$^7$, —COR$^7$, —COOR$^7$ or —CONR$^4$R$^6$, wherein (a) one or more of the carbon atoms in the alkyl, alkenyl or alkynyl group is each independently optionally replaced with a nitrogen, sulfur or oxygen atom, and (b) the alkyl, alkenyl or alkynyl group is optionally substituted with a —C$_1$-C$_3$-alkyl;

R$^3$ is an optionally substituted aliphatic, alicyclic, heteroaliphatic, heterocyclic, aromatic, or hetero aromatic;

R$^4$ and R$^6$ are each independently hydrogen, —C$_1$-C$_6$-alkyl, —C$_2$-C$_6$-alkenyl, —C$_2$-C$_6$-alkynyl, —COR$^7$, —C$_5$-C$_7$-aryl, or —C$_5$-C$_{10}$-arylalkyl, wherein (a) one or more of the carbon atoms in the alkyl, alkenyl, alkynyl, aryl or arylalkyl group is each independently optionally replaced with a nitrogen, sulfur or oxygen atom, and (b) the alkyl, alkenyl, alkynyl, aryl or arylalkyl is optionally substituted with an oxygen, a —C$_1$-C$_3$-alkyl, or a —C$_5$-C$_7$-aryl;

R$^5$ is one or more hydrogen, hydroxy, halogen, cyano, alkyloxy, nitro, NH$_2$, NHCOR$^4$, NHSO$_2$R$^4$, CONHR$^4$, COOR$^4$, optionally substituted aliphatic, alicyclic, heteroaliphatic, heterocyclic, aromatic, or heteroaromatic; and R$^7$ is hydrogen, —C$_1$-C$_6$-alkyl, —C$_2$-C$_6$-alkenyl, —C$_2$-C$_6$-alkynyl, —C$_5$-C$_7$-aryl, or —C$_5$-C$_{10}$-arylalkyl, wherein (a) one or more of the carbon atoms in the alkyl, alkenyl, alkynyl, aryl or arylalkyl group is each independently optionally replaced with a nitrogen, sulfur or oxygen atom, and (b) the alkyl, alkenyl, alkynyl, aryl or arylalkyl is optionally substituted with a halogen, a —C$_1$-C$_3$-alkyl, a —C$_5$-C$_7$-aryl, or —NR$^4$R$^6$ or —OR$^4$;

or an isomer, enantiomer, racemate, prodrug, active metabolite, metal chelate, or a pharmaceutically-acceptable derivative or salt form of any of the foregoing.

In certain embodiments, R$^1$ is chloro, nitro or cyano. In other embodiments R$^2$ is hydroxy. In other embodiments, R$^3$ can be alkyl or aralkyl.

In certain embodiments, R$^1$ is chloro and R$^2$ is hydroxy. In other embodiments, R$^5$ is one or more methoxy, hydroxy, halo, or dimethylamino groups. In further embodiments, R$^3$ is an optionally substituted alkyl or aralkyl group.

Non-limiting examples of such compounds include N-[(5-chloro-8-hydroxyquinolin-7-yl)-(3,4-dimethoxyphenyl)methyl]propanamide, N-[(5-chloro-8-hydroxyquinolin-7-yl)-(4-methoxyphenyl)methyl]propanamide, N-[(5-chloro-8-hydroxyquinolin-7-yl)-tolyl]-3-phenylpropanamide, N-[(5-chloro-8-hydroxyquinolin-7-yl)-(3-methoxyphenyl)methyl]-3-phenylpropanamide, N-[(5-chloro-8-hydroxyquinolin-7-yl)-(4-dimethylaminophenyl)methyl]-3-phenylpropanamide, N-[(5-chloro-8-hydroxyquinolin-7-yl)-(4-chlorophenyl)methyl]-3-phenylpropanamide, N-[(5-chloro-8-hydroxyquinolin-7-yl)-(3-chlorophenyl)methyl]-3-phenylpropanamide, N-[(5-chloro-8-hydroxyquinolin-7-yl)-(2-chlorophenyl)methyl]-3-phenylpropanamide, N-[(5-chloro-8-hydroxyquinolin-7-yl)-(3,4-dimethoxyphenyl)methyl]-3-phenylpropanamide, N-[(5-chloro-8-hydroxyquinolin-7-yl)-(2,4-dimethoxyphenyl)methyl]-3-phenylpropanamide, N-[(5-chloro-8-hydroxyquinolin-7-yl)-(3,4,5-trimethoxyphenyl)methyl]-3-phenylpropanamide, N-[(5-chloro-8-hydroxyquinolin-7-yl)-(2-bromophenyl)methyl]-3-phenylpropanamide, N-[(5-chloro-8-hydroxyquinolin-7-yl)-p-tolyl-methyl]-3-phenylpropanamide, N-[(5-chloro-8-hydroxyquinolin-7-yl)-(2-hydroxyphenyl)methyl]-3-phenylpropanamide, N-[(5-chloro-8-hydroxyquinolin-7-yl)-(4-methoxyphenyl)methyl]-3-phenylpropanamide, N-[(8-Hydroxy-5-nitro-quinolin-7-yl)-p-tolyl-methyl]-propionamide, N-[{8-hydroxy-5-nitro-7-quinolinyl}(4-methylphenyl)methyl]acetamide, and N-[(8-hydroxyquinolin-7-yl)-(2-methoxyphenyl)methyl]pentanamide.

DEFINITIONS

It is understood that the compounds, as described herein, may be substituted with any number of substituents or functional moieties. In general, the term "substituted" whether preceded by the term "optionally" or not, and substituents contained in formulas of this invention, refer to the replacement of hydrogen radicals in a given structure with the radical of a specified substituent. When more than one position in any given structure may be substituted with more than one substituent selected from a specified group, the substituent may be either the same or different at every position. As used herein, the term "substituted" is contemplated to include all permissible substituents of organic compounds. In a broad aspect, the permissible substituents include acyclic and cyclic, branched and unbanked, carbocyclic and heterocyclic, aromatic and non-aromatic, carbon and heteroatom substituents of organic compounds. For purposes of this invention, heteroatoms such as nitrogen may have hydrogen substituents and/or any permissible substituents of organic compounds described herein which satisfy the valencies of the heteroatoms. Furthermore, this invention is not intended to be limited in any manner by the permissible substituents of organic compounds. Combinations of substituents and variables envisioned by this invention are preferably those that result in the formation of stable compounds useful in the treatment and prevention, for example of disorders, as described generally above. Examples of substituents include, but are not limited to aliphatic; heteroaliphatic; alicyclic; heterocyclic; aromatic, heteroaromatic; aryl; heteroaryl; alkylaryl; aralkyl; alkylheteroaryl; alkoxy; aryloxy; heteroalkoxy; heteroaryloxy; alkylthio; arylthio; heteroalkylthio; heteroarylthio; F; Cl; Br; I; —NO$_2$; —CN; —CF$_3$; —CH$_2$CF$_3$; —CHCl$_2$; —CH$_2$OH; —CH$_2$CH$_2$OH; —CH$_2$NH$_2$; —CH$_2$SO$_2$CH$_3$; or -GR$^{G1}$ wherein G is —O—, —S—, —NR$^{G2}$—, —C(=O)—, —S(=O)—, —SO$_2$—, —C(=O)O—, —C(=O)NR$^{G2}$—, —OC(=O)—, —NR$^{G2}$C(=O)—, —OC(=O)O—, —OC(=O)NR$^{G2}$—, —NR$^{G2}$C(=O)O—, —NR$^{G2}$C(=O)NR$^{G2}$—, —C(=S)—, —C(=S)S—, —SC(=S)—, —SC(=S)S—, —C(=NR$^{G2}$)—, —C(=NR$^{G2}$)O—, —C(=NR$^{G2}$)NR$^{G3}$—, —OC(=NR$^{G2}$)—, —NR$^{G2}$C(=NR$^{G3}$)—, —NR$^{G2}$SO$_2$—, —NR$^{G2}$SO$_2$NR$^{G3}$—, or —SO$_2$NR$^{G2}$—, wherein each occurrence of R$^{G1}$, R$^{G2}$ and R$^{G3}$ independently includes, but is not limited to, hydrogen, halogen, or an optionally substituted aliphatic, heteroaliphatic, alicyclic, heterocyclic, aromatic, heteroaromatic, aryl, heteroaryl, alkylaryl, or alkylheteroaryl moiety.

The term "stable", as used herein, preferably refers to compounds which possess stability sufficient to allow manufacture and which maintain the integrity of the compound for a sufficient period of time to be detected and preferably for a sufficient period of time to be useful for the purposes detailed herein.

The term "aliphatic", as used herein, includes both saturated and unsaturated, straight chain (i.e., unbranched) or branched aliphatic hydrocarbons as defined by IUPAC, which are optionally substituted with one or more functional groups. As defined herein, "aliphatic" is intended to include optionally substituted alkyl, alkenyl and alkynyl moieties. Thus, as used herein, the term "alkyl" includes straight and branched alkyl groups. An analogous convention applies to other generic terms such as "alkenyl", "alkynyl" and the like. Furthermore, as used herein, the terms "alkyl", "alkenyl", "alkynyl" and the like encompass both substituted and unsubstituted groups. In certain embodiments, as used herein, "lower alkyl" is used to indicate those alkyl groups (substituted, unsubstituted, branched or unbranched) having about 1-6 carbon atoms. In some instances aliphatic can include alicyclic or cycloalkyl, including unsaturations therein.

In certain embodiments, the alkyl, alkenyl and alkynyl groups employed in the invention contain 1-20; 2-20; 3-20; 4-20; 5-20; 6-20; 7-20 or 8-20 aliphatic carbon atoms. In certain other embodiments, the alkyl, alkenyl, and alkynyl groups employed in the invention contain 1-10; 2-10; 3-10; 4-10; 5-10; 6-10; 7-10 or 8-10 aliphatic carbon atoms. In yet other embodiments, the alkyl, alkenyl, and alkynyl groups employed in the invention contain 1-8; 2-8; 3-8; 4-8; 5-8; 6-20 or 7-8 aliphatic carbon atoms. In still other embodiments, the alkyl, alkenyl, and alkynyl groups employed in the invention contain 1-6; 2-6; 3-6; 4-6 or 5-6 aliphatic carbon atoms. In yet other embodiments, the alkyl, alkenyl, and alkynyl groups employed in the invention contain 1-4; 2-4 or 3-4 carbon atoms. Illustrative aliphatic groups thus include, but are not limited to, for example, methyl, ethyl, n-propyl, isopropyl, allyl, n-butyl, sec-butyl, isobutyl, tert-butyl, n-pentyl, sec-pentyl, isopentyl, tert-pentyl, n-hexyl, sec-hexyl, moieties and the like, which again, may bear one or more substituents. Alkenyl groups include, but are not limited to, for example, ethenyl, propenyl, butenyl, 1-methyl-2-buten-1-yl, and the like. Representative alkynyl groups include, but are not limited to, ethynyl, 2-propynyl(propargyl), 1-propynyl and the like.

The term "alicyclic", as used herein, refers to compounds that combine the properties of aliphatic and cyclic compounds and include but are not limited to cyclic, or polycyclic aliphatic hydrocarbons and bridged cycloalkyl compounds, which are optionally substituted with one or more functional groups. As will be appreciated by one of ordinary skill in the art, "alicyclic" is intended herein to include, but is not limited to, cycloalkyl, cycloalkenyl, and cycloalkynyl moieties, which are optionally substituted with one or more functional groups. Illustrative alicyclic groups thus include, but are not limited to, for example, cyclopropyl, —CH$_2$-cyclopropyl, cyclobutyl, —CH$_2$-cyclobutyl, cyclopentyl, —CH$_2$-cyclopentyl-n, cyclohexyl, —CH$_2$-cyclohexyl, cyclohexenylethyl, cyclohexanylethyl, norborbyl moieties and the like, which again, may bear one or more substituents.

The term "cycloalkyl", as used herein, refers to cyclic alkyl groups, specifically to groups having three to seven, preferably three to ten carbon atoms. Suitable cycloalkyls include, but are not limited to cyclopropyl, cyclobutyl, cyclopentyl, cyclohexyl, cycloheptyl and the like, which, as in the case of aliphatic, heteroaliphatic or heterocyclic moieties, may optionally be substituted. An analogous convention applies to other generic terms such as "cycloalkenyl", "cycloalkynyl" and the like.

The term "heteroaliphatic", as used herein, refers to aliphatic moieties in which one or more carbon atoms in the main chain have been replaced with a heteroatom. Thus, a heteroaliphatic group refers to an aliphatic chain which contains one or more oxygen, sulfur, nitrogen, phosphorus or silicon atoms in place of carbon atoms in the aliphatic main chain. Heteroaliphatic moieties may be branched or linear unbranched. In certain embodiments, heteroaliphatic moieties are substituted by independent replacement of one or more of the hydrogen atoms thereon with one or more moieties including, but not limited to aliphatic; heteroaliphatic; alicyclic; heterocyclic; aromatic, heteroaromatic; aryl; heteroaryl; alkylaryl; alkylheteroaryl; alkoxy; aryloxy; heteroalkoxy; heteroaryloxy; alkylthio; arylthio; heteroalkylthio; heteroarylthio; F; Cl; Br; I; —NO$_2$; —CN; —CF$_3$; —CH$_2$CF$_3$; —CHCl$_2$; —CH$_2$OH; —CH$_2$CH$_2$OH; —CH$_2$NH$_2$; —CH$_2$SO$_2$CH$_3$; or -GR$^{G1}$ wherein G is —O—, —S—, —NR$^{G2}$—, —C(=O)—, —S(=O)—, —SO$_2$—, —C(=O)O—, —C(=O)NR$^{G2}$—, —OC(=O)—, —NR$^{G2}$C(=O)—, —OC(=O)O—, —OC(=O)NR$^{G2}$—, —NR$^{G2}$C(=O)O—, —NR$^{G2}$C(=O)NR$^{G2}$—, —C(=S)—, —C(=S)S—, —SC(=S)—, —SC(=S)S—, —C(=NR$^{G2}$)—, —C(=NR$^{G2}$)O—, —C(=NR$^{G2}$)NR$^{G3}$—, —OC(=NR$^{G2}$)—, —NR$^{G2}$C(=NR$^{G3}$)—, —NR$^{G2}$SO$_2$—, —NR$^{G2}$SO$_2$NR$^{G3}$—, or —SO$_2$NR$^{G2}$—, wherein each occurrence of R$^{G1}$, R$^{G2}$ and R$^{G3}$ independently includes, but is not limited to, hydrogen, halogen, or an optionally substituted aliphatic, heteroaliphatic, alicyclic, heterocyclic, aromatic, heteroaromatic, aryl, heteroaryl, alkylaryl, or alkylheteroaryl moiety.

The term "heteroalicyclic", "heterocycloalkyl" or "heterocyclic", as used herein, refers to compounds which combine the properties of heteroaliphatic and cyclic compounds and include but are not limited to saturated and unsaturated mono- or polycyclic ring systems having 5-16 atoms wherein at least one ring atom is a heteroatom selected from O, S and N (wherein the nitrogen and sulfur heteroatoms may be optionally be oxidized), wherein the ring systems are optionally substituted with one or more functional groups, as defined herein. In certain embodiments, the term "heterocyclic" refers to a non-aromatic 5-, 6- or 7-membered ring or a polycyclic group, including, but not limited to a bi- or tricyclic group comprising fused six-membered rings having between one and three heteroatoms independently selected from oxygen, sulfur and nitrogen, wherein (i) each 5-membered ring has 0 to 2 double bonds and each 6-membered ring has 0 to 2 double bonds, (ii) the nitrogen and sulfur heteroatoms may optionally be oxidized, (iii) the nitrogen heteroatom may optionally be quaternized, and (iv) any of the above heterocyclic rings may be fused to an aryl or heteroaryl ring. Representative heterocycles include, but are not limited to, pyrrolidinyl, pyrazolinyl, pyrazolidinyl imidazolinyl, imidazolidinyl, piperidinyl, piperazinyl, oxazolidinyl, isoxazolidinyl, morpholinyl, thiazolidinyl, isothiazolidinyl, and tetrahydrofuryl. In certain embodiments, a "substituted heterocycloalkyl or heterocycle" group is utilized and as used herein, refers to a heterocycloalkyl or heterocycle group, as defined above, substituted by the independent replacement of one or more hydrogen atoms thereon with aliphatic; heteroaliphatic; alicyclic; heterocyclic; aromatic, heteroaromatic; aryl; heteroaryl; alkylaryl; alkylheteroaryl; alkoxy; aryloxy; heteroalkoxy; heteroaryloxy; alkylthio; arylthio; heteroalkylthio; heteroarylthio; F; Cl; Br; I; —NO$_2$; —CN; —CF$_3$; —CH$_2$CF$_3$; —CHCl$_2$; —CH$_2$OH; —CH$_2$CH$_2$OH; —CH$_2$NH$_2$; —CH$_2$SO$_2$CH$_3$; or -GR$^{G1}$ wherein G is —O—, —S—, —NR$^{G2}$—, —C(=O)—, —S(=O)—, —SO$_2$—, —C(=O)O—, —C(=O)NR$^{G2}$—, —OC(=O)—, —NR$^{G2}$C(=O)—, —OC(=O)O—, —OC(=O)NR$^{G2}$—, —NR$^{G2}$C(=O)O—, —NR$^{G2}$C(=O)NR$^{G2}$—, —C(=S)—, —C(=S)S—, —SC(=S)—, —SC(=S)S—, —C(=NR$^{G2}$)—, —C(=NR$^{G2}$)O—, —C(=NR$^{G2}$)NR$^{G3}$—, —OC(=NR$^{G2}$)—, —NR$^{G2}$C(=NR$^{G3}$)—, —NR$^{G2}$SO$_2$—, —NR$^{G2}$SO$_2$NR$^{G3}$—, or —SO$_2$NR$^{G2}$—, wherein each occurrence of R$^{G1}$, R$^{G2}$ and R$^{G3}$ independently includes, but is not limited to, hydrogen, halogen, or an optionally substituted aliphatic, heteroaliphatic, alicyclic, heterocyclic, aromatic, heteroaromatic, aryl, heteroaryl, alkylaryl, or alkylheteroaryl moiety.

Additionally, it will be appreciated that any of the alicyclic or heterocyclic moieties described above and herein may comprise an aryl or heteroaryl moiety fused thereto.

In general, the term "aromatic moiety", as used herein, refers to a stable mono- or polycyclic, unsaturated moiety having preferably 3-14 carbon atoms, each of which may be substituted or unsubstituted. In certain embodiments, the term "aromatic moiety" refers to a planar ring having p-orbitals perpendicular to the plane of the ring at each ring atom and satisfying the Huckel rule where the number of pi electrons in the ring is (4n+2) wherein n is an integer. A mono- or polycyclic, unsaturated moiety that does not satisfy one or all of these criteria for aromaticity is defined herein as "non-aromatic", and is encompassed by the term "alicyclic". Examples of aromatic moieties include, but are not limited to, phenyl, indanyl, indenyl, naphthyl, phenanthryl and anthracyl.

In general, the term "heteroaromatic moiety", as used herein, refers to stable substituted or unsubstituted unsaturated mono-heterocyclic or polyheterocyclic moieties having preferably 3-14 carbon atoms, comprising at least one ring having p-orbitals perpendicular to the plane of the ring at each ring atom, and satisfying the Huckel rule where the number of pi electrons in the ring is (4n+2) wherein n is an integer. Examples of heteroaromatic moieties include, but are not limited to, pyridyl, quinolinyl, dihydroquinolinyl, isoquinolinyl, quinazolinyl, dihydroquinazolyl, and tetrahydroquinazolyl.

It will also be appreciated that aromatic and heteroaromatic moieties, as defined herein, may be attached via an aliphatic (e.g., alkyl) or heteroaliphatic (e.g., heteroalkyl) moiety and thus also include moieties such as -(aliphatic)aromatic, -(heteroaliphatic)aromatic, -(aliphatic)heteroaromatic, -(heteroaliphatic)heteroaromatic, -(alkyl)aromatic, -(heteroalkyl)aromatic, -(alkyl)heteroaromatic, and -(heteroalkyl)heteroaromatic moieties. Thus, as used herein, the phrases "aromatic or heteroaromatic moieties" and "aromatic, heteroaromatic, -(alkyl) aromatic, -(heteroalkyl)aromatic, -(heteroalkyl)heteroaromatic, and -(heteroalkyl)heteroaromatic" are interchangeable. In some instances corresponding moieties may be referred to synonymously as aralkyl, heteroaralkyl and the like. Substituents include, but are not limited to, any of the previously mentioned substituents, i.e., the substituents recited for aliphatic moieties, or for other moieties as disclosed herein, resulting in the formation of a stable compound.

"Aralkyl," also called "arylalkyl," refers to an aryl group terminating with an aliphatic group, such as a benzyl, phenylethyl, phenylpropyl, or phenylbutyl group, etc. The aryl moiety may be substituted as generally described herein, as may be the aliphatic moiety. The aliphatic moiety may be as defined above, such as an alkyl, alkenyl or alkynyl group.

In general, the term "aryl" refers to aromatic moieties, as described above, excluding those attached via an aliphatic (e.g., alkyl) or heteroaliphatic (e.g., heteroalkyl) moiety. In certain embodiments of the present invention, "aryl" refers to a mono- or bicyclic carbocyclic ring system having one or two rings satisfying the Huckel rule for aromaticity, including, but not limited to, phenyl, naphthyl, tetrahydronaphthyl, indanyl, indenyl and the like.

Similarly, the term "heteroaryl" refers to heteroaromatic moieties, as described above, excluding those attached via an aliphatic (e.g., alkyl) or heteroaliphatic (e.g., heteroalkyl) moiety. In certain embodiments of the present invention, the term "heteroaryl", as used herein, refers to a cyclic unsaturated radical having from about five to about ten ring atoms of which one ring atom is selected from S, O and N; zero, one or two ring atoms are additional heteroatoms independently selected from S, O and N; and the remaining ring atoms are carbon, the radical being joined to the rest of the molecule via any of the ring atoms, such as, for example, pyridyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, and the like.

As defined herein, "aryl" and "heteroaryl" groups (including bicyclic aryl groups) can be unsubstituted or substituted, wherein substitution includes replacement of one or more of the hydrogen atoms thereon independently with any of the previously mentioned substituents, i.e., the substituents recited for aliphatic moieties, or for other moieties as disclosed herein, resulting in the formation of a stable compound. For example, aryl and heteroaryl groups (including bicyclic aryl groups) can be unsubstituted or substituted, wherein substitution includes replacement of one or more of the hydrogen atoms thereon independently with any one or more of the following moieties including, but not limited to: aliphatic; heteroaliphatic; alicyclic; heterocyclic; aromatic; heteroaromatic; aryl; heteroaryl; alkylaryl; alkylheteroaryl; alkoxy; aryloxy; heteroalkoxy; heteroaryloxy; alkylthio; arylthio; heteroalkylthio; heteroarylthio; F; Cl; Br; I; —NO$_2$; —CN; —CF$_3$; —CH$_2$CF$_3$; —CHCl$_2$; —CH$_2$OH; —CH$_2$CH$_2$OH; —CH$_2$NH$_2$; —CH$_2$SO$_2$CH$_3$; or -GR$^{G1}$ wherein G is —O—, —S—, —NR$^{G2}$—, —C(=O)—, —S(=O)—, —SO$_2$—, —C(=O)O—, —C(=O)NR$^{G2}$—, —OC(=O)—, —NR$^{G2}$C(=O)—, —OC(=O)O—, —OC(=O)NR$^{G2}$—, —NR$^{G2}$C(=O)O—, —NR$^{G2}$C(=O)NR$^{G2}$—, —C(=S)—, —C(=S)S—, —SC(=S)—, —SC(=S)S—, —C(=NR$^{G2}$)—, —C(=NR$^{G2}$)O—, —C(=NR$^{G2}$)NR$^{G3}$—, —OC(=NR$^{G2}$)—, —NR$^{G2}$C(=NR$^{G3}$)—, —NR$^{G2}$SO$_2$—, —NR$^{G2}$SO$_2$NR$^{G3}$—, or —SO$_2$NR$^{G2}$—, wherein each occurrence of R$^{G1}$, R$^{G2}$ and R$^{G3}$ independently includes, but is not limited to, hydrogen, halogen, or an optionally substituted aliphatic, heteroaliphatic, alicyclic, heterocyclic, aromatic, heteroaromatic, aryl, heteroaryl, alkylaryl, or alkylheteroaryl moiety. Additionally, it will be appreciated, that any two adjacent groups taken together may represent a 4, 5, 6, or 7-membered substituted or unsubstituted alicyclic or heterocyclic moiety.

The term "alkoxy" or "alkyloxy", as used herein refers to a saturated (i.e., O-alkyl) or unsaturated (i.e., O-alkenyl and O-alkynyl) group attached to the parent molecular moiety through an oxygen atom. In certain embodiments, the alkyl group contains 1-20; 2-20; 3-20; 4-20; 5-20; 6-20; 7-20 or 8-20 aliphatic carbon atoms. In certain other embodiments, the alkyl group contains 1-10; 2-10; 3-10; 4-10; 5-10; 6-10; 7-10 or 8-10 aliphatic carbon atoms. In yet other embodiments, the alkyl, alkenyl, and alkynyl groups employed in the invention contain 1-8; 2-8; 3-8; 4-8; 5-8; 6-20 or 7-8 aliphatic carbon atoms. In still other embodiments, the alkyl group contains 1-6; 2-6; 3-6; 4-6 or 5-6 aliphatic carbon atoms. In yet other embodiments, the alkyl group contains 1-4; 2-4 or 3-4 aliphatic carbon atoms. Examples of alkoxy, include but are not limited to, methoxy, ethoxy, propoxy, isopropoxy, n-butoxy, i-butoxy, sec-butoxy, tert-butoxy, neopentoxy, n-hexoxy and the like.

The term "thioalkyl" as used herein refers to a saturated (i.e., S-alkyl) or unsaturated (i.e., S-alkenyl and S-alkynyl) group attached to the parent molecular moiety through a sulfur atom. In certain embodiments, the alkyl group contains 1-20 aliphatic carbon atoms. In certain other embodiments, the alkyl group contains 1-10 aliphatic carbon atoms. In yet other embodiments, the alkyl, alkenyl, and alkynyl groups employed in the invention contain 1-8 aliphatic carbon atoms. In still other embodiments, the alkyl group contains 1-6 aliphatic carbon atoms. In yet other embodiments, the alkyl group contains 1-4 aliphatic carbon atoms. Examples of thioalkyl include, but are not limited to, methylthio, ethylthio, propylthio, isopropylthio, n-butylthio, and the like.

The term "alkylamino" refers to a group having the structure —NHR' wherein R' is aliphatic or alicyclic, as defined herein. The term "aminoalkyl" refers to a group having the structure $NH_2R'$—, wherein R' is aliphatic or alicyclic, as defined herein. In certain embodiments, the aliphatic or alicyclic group contains 1-20 aliphatic carbon atoms. In certain other embodiments, the aliphatic or alicyclic group contains 1-10 aliphatic carbon atoms. In still other embodiments, the aliphatic or alicyclic group contains 1-6 aliphatic carbon atoms. In yet other embodiments, the aliphatic or alicyclic group contains 1-4 aliphatic carbon atoms. In yet other embodiments, R' is an alkyl, alkenyl, or alkynyl group containing 1-8 aliphatic carbon atoms. Examples of alkylamino include, but are not limited to, methylamino, ethylamino, iso-propylamino and the like.

Some examples of substituents of the above-described aliphatic (and other) moieties of compounds of the invention include, but are not limited to aliphatic; alicyclic; heteroaliphatic; heterocyclic; aromatic; heteroaromatic; aryl; heteroaryl; alkylaryl; heteroalkylaryl; alkylheteroaryl; heteroalkylheteroaryl; alkoxy; aryloxy; heteroalkoxy; heteroaryloxy; alkylthio; arylthio; heteroalkylthio; heteroarylthio; F; Cl; Br; I; —OH; —$NO_2$; —CN; —$CF_3$; —$CH_2CF_3$; —$CHCl_2$; —$CH_2OH$; —$CH_2CH_2OH$; —$CH_2NH_2$; —$CH_2SO_2CH_3$; —C(=O)$R_x$; —$CO_2(R_x)$; —C(=O)N($R_x$)$_2$; —OC(=O)$R_x$; —$OCO_2R_x$; —OC(=O)N($R_x$)$_2$; —N($R_x$)$_2$; —$OR_x$; —$SR_x$; —S(O)$R_x$; —S(O)$_2R_x$; —$NR_x$(CO)$R_x$; —N($R_x$)$CO_2R_x$; —N($R_x$)S(O)$_2R_x$; —N($R_x$)C(=O)N($R_x$)$_2$; —S(O)$_2$N($R_x$)$_2$; wherein each occurrence of $R_x$ independently includes, but is not limited to, aliphatic, alicyclic, heteroaliphatic, heterocyclic, aryl, heteroaryl, alkylaryl, alkylheteroaryl, heteroalkylaryl or heteroalkylheteroaryl, wherein any of the aliphatic, alicyclic, heteroaliphatic, heterocyclic, alkylaryl, or alkylheteroaryl substituents described above and herein may be substituted or unsubstituted, branched or unbranched, saturated or unsaturated, and wherein any of the aryl or heteroaryl substituents described above and herein may be substituted or unsubstituted.

The terms "halo" and "halogen" as used herein refer to an atom selected from fluorine, chlorine, bromine and iodine.

The term "haloalkyl" denotes an alkyl group, as defined above, having one, two, or three halogen atoms attached thereto and is exemplified by such groups as chloromethyl, bromoethyl, trifluoromethyl, and the like.

The term "amino", as used herein, refers to a primary (—$NH_2$), secondary (—$NHR_x$), tertiary (—$NR_xR_y$) or quaternary (—$N^+R_xR_yR_z$) amine, where $R_x$, $R_y$ and $R_z$ are independently an aliphatic, alicyclic, heteroaliphatic, heterocyclic, aromatic or heteroaromatic moiety, as defined herein. Examples of amino groups include, but are not limited to, methylamino, dimethylamino, ethylamino, diethylamino, diethylaminocarbonyl, methylethylamino, iso-propylamino, piperidino, trimethylamino, and propylamino.

The term "acyl", as used herein, refers to a group having the general formula —C(=O)R, where R is an aliphatic, alicyclic, heteroaliphatic, heterocyclic, aromatic or heteroaromatic moiety, as defined herein.

The term "$C_{2-6}$alkenylene", as used herein, refers to a substituted or unsubstituted, linear or branched unsaturated divalent radical consisting solely of carbon and hydrogen atoms, having from two to six carbon atoms, having a free valence "–" at both ends of the radical, and wherein the unsaturation is present only as double bonds and wherein a double bond can exist between the first carbon of the chain and the rest of the molecule.

As used herein, the terms "aliphatic", "heteroaliphatic", "alkyl", "alkenyl", "alkynyl", "heteroalkyl", "heteroalkenyl", "heteroalkynyl", and the like encompass substituted and unsubstituted, saturated and unsaturated, and linear and branched groups. Similarly, the terms "alicyclic", "heterocyclic", "heterocycloalkyl", "heterocycle" and the like encompass substituted and unsubstituted, and saturated and unsaturated groups. Additionally, the terms "cycloalkyl", "cycloalkenyl", "cycloalkynyl", "heterocycloalkyl", "heterocycloalkenyl", "heterocycloalkynyl", "aromatic", "heteroaromatic", "aryl", "heteroaryl" and the like encompass both substituted and unsubstituted groups.

The phrase "the phenotype thereof" refers to an effect that is a partial, an equivalent, or in excess of the extent of the effect of the preceding term or terms. For example, frataxin depletion increases iron accumulation, increases oxidative stress and causes mitochondrial dysfunction. Increasing cellular frataxin gene expression results in the decrease in iron accumulation, decrease in oxidative stress, or improving mitochondrial dysfunction. In one embodiment, the phenotype of increasing frataxin gene expression can produce a partial decrease in iron accumulation, partial decrease in oxidative stress or partial reduction of mitochondrial dysfunction. In another embodiment, the phenotype of increasing frataxin gene expression can produce an extent of decrease in iron accumulation, decrease in oxidative stress or reduction of mitochondrial dysfunction equivalent to that extent achieved by increasing frataxin gene expression. In another embodiment, the phenotype of increasing frataxin gene expression can produce an extent of decrease in iron accumulation, decrease in oxidative stress or reduction of mitochondrial dysfunction that exceeds that extent achieved by increasing frataxin gene expression.

The term "compensating" or "compensate" in reference to frataxin deficiency or mutation refers to the property of increasing, improving, or restoring cellular biochemistry or metabolism that is impaired by a frataxin deficiency or mutation, or the phenotype thereof, wherein the compensating does not necessarily involve, or altogether does not involve, a direct effect on frataxin levels, expression or activity. In referring to a compound embodied herein as compensating for frataxin deficiency or mutation, the compound has the property in cells, tissues, or in subjects, of increasing, improving, or restoring cellular biochemistry or metabolism that is impaired by a frataxin deficiency or mutation, wherein the compound does not necessarily involve, or altogether dose not involve, a direct effect on frataxin levels, expression or activity.

The phrase, "pharmaceutically acceptable derivative", as used herein, denotes any pharmaceutically acceptable salt, ester, or salt of such ester, of such compound, or any other adduct or derivative which, upon administration to a patient, is capable of providing (directly or indirectly) a compound as otherwise described herein, or a metabolite or residue thereof. Pharmaceutically acceptable derivatives thus include among others prodrugs. A prodrug is a derivative of a compound, usually with significantly reduced pharmacological activity, which contains an additional moiety, which is susceptible to removal in vivo yielding the parent molecule as the pharmacologically active species. An example of a prodrug is an ester, which is cleaved in vivo to yield a compound of interest. Another example is an N-methyl derivative of a compound, which is susceptible to oxidative metabolism resulting in N-demethylation. Prodrugs of a variety of compounds, and materials and methods for derivatizing the parent compounds to create the prodrugs, are known and may be adapted to the present invention.

The phrase, "active metabolite", refers to a biologically active derivative of a compound that is formed when the compound is metabolized. The term "metabolized," as used herein, refers to the sum of the processes (including, but not limited to, hydrolysis reactions and reactions catalyzed by enzymes, such as, oxidation reactions) by which a particular substance is changed by an organism. Thus, enzymes may produce specific structural alterations to a compound. For example, cytochrome P450 catalyzes a variety of oxidative and reductive reactions while uridine diphosphate glucuronyl transferases catalyze the transfer of an activated glucuronic-acid molecule to aromatic alcohols, aliphatic alcohols, carboxylic acids, amines and free sulfhydryl groups. Further information on metabolism may be obtained from The Pharmacological Basis of Therapeutics, 9th Edition, McGraw-Hill (1996). Metabolites of the compounds disclosed herein can be identified either by administration of compounds to a host and analysis of tissue samples from the host, or by incubation of compounds with hepatic cells in vitro and analysis of the resulting compounds. Both methods are well known in the art. In some embodiments, a compound is metabolized to pharmacologically active metabolites.

The term "isomers" refers to stereoisomers and/or diastereomers of the compounds, as some of the foregoing compounds can comprise one or more asymmetric centers, and thus can exist in various such isomeric forms. Thus, inventive compounds and pharmaceutical compositions thereof may be in the form of an individual enantiomer, diastereomer or geometric isomer, or may be in the form of a mixture of stereoisomers. In certain embodiments, the compounds of the invention are enantiopure compounds. In certain other embodiments, mixtures of stereoisomers or diastereomers are provided. In other embodiments a compound is racemic.

The term "geometrical isomers" refers to cis-trans isomerism, syn-anti or E/Z isomerism based on the Cahn-Ingold-Prelog system. See March's Advanced Organic Chemistry: Reactions, Mechanisms and Structures, Sixth Edition, Wiley-Interscience, pages 182-195 (2007). The term "geometrical isomers" as used herein, refers to compounds having double bond with an E or Z configuration or cis-trans isomers of monocyclic or fused ring systems.

Furthermore, certain compounds, as described herein may have one or more double bonds that can exist as either the Z or E isomer, unless otherwise indicated. The invention additionally encompasses the compounds as individual isomers substantially free of other isomers and alternatively, as mixtures of various isomers, e.g., racemic mixtures of stereoisomers. In addition to the above-mentioned compounds per se, this invention also encompasses pharmaceutically acceptable derivatives of these compounds and compositions comprising one or more compounds of the invention and one or more pharmaceutically acceptable excipients or additives.

The term "metal chelate" refers to a compound of the invention that has bound one or more metal ions, such as but not limited to iron or manganese, in any one or more of their ionic forms.

DETAILED DESCRIPTION OF THE INVENTION

Friedreich's ataxia (FRDA) is an autosomal recessive neurodegenerative disorder caused by mutations in the FXN gene, which encodes the protein frataxin, and for which there are no currently accepted treatments. It is the most common hereditary ataxia and causes progressive damage to the nervous system, particularly sensory neurons, resulting in symptoms ranging from ataxia, muscle fatigability, and speech problems to hypertrophic cardiomyopathy. Frataxin localizes to the mitochondrial matrix, where it chaperones iron for the assembly of iron-sulfur clusters that are then employed by a variety of respiratory and other enzymes. Mitochondrial dysfunction is therefore the primary underlying cause of the signs and symptoms of FRDA.

Beyond FRDA, mitochondrial dysfunction is a key contributor to a number of other diseases and conditions for which effect treatments remain elusive. Mitochondrial dysfunction elevates levels of toxic, reactive oxygen species that damage DNA and other cellular components. Abnormal iron homeostasis and mitochondrial iron accumulation contributes to mitochondrial dysfunction. Conditions and diseases including various neurodegenerative diseases, as well as normal aging, complications of diabetes, and age-related macular degeneration are but a few examples of such diseases related to mitochondrial dysfunction or mitochondrial iron accumulation. Others include neurodegeneration with brain iron accumulation (NBIA), Parkinson's disease, Alzheimer's disease, a mitochondrial encephalopathy, hemochromatosis, aceruloplasminemia, thalassemia, attention deficit hyperactivity disorder (ADHD), and Tourette's syndrome. Within neurodegenerative diseases, Parkinson's disease, Alzheimer's disease, and mitochondrial encephalopathies are believed to have a pathophysiological cause or at least a component due to mitochondrial dysfunction. Compounds that improve or restore defects in mitochondrial metabolism, whether or not in the mitochondrial electron transport chain, are highly sought for potential therapeutic applications or as means to help identify targets in mitochondrial biochemistry to facilitate identifying other therapeutic interventions. Thus, in one embodiment, compounds described herein have been identified that improve mitochondrial function. In another embodiment the compounds described herein decrease iron accumulation, or improve or restore iron homeostasis. In another embodiment the compounds described herein decrease oxidative stress.

As will be seen in the examples below, a facile means for screening and identifying compounds that restore the defect in mitochondrial metabolism present in, for example, FRDA or other defects, employs a yeast model system that recognizes that the yeast protein Yfh1p is a close structural and functional homolog of frataxin. This facilitates use of this yeast model system as a screening tool for compounds that substitute or circumvent this defect. Virtually every finding regarding the role of Yfh1p in yeast has been confirmed for frataxin in human cells. In yeast, mitochondrial function can be assayed by quantifying growth in media containing a non-fermentable carbon source, such as glycerol. A colorimetric assay using a tetrazolium dye such as WST-1, which is reduced by cellular dehydrogenases, can then be used to quantitatively monitor the metabolic activity of cells.

Frataxin can substitute for the yeast frataxin homologue, Yfh1p, indicating that the two proteins are orthologues, and virtually every finding regarding the role of Yfh1p in yeast has been confirmed for frataxin in human cells. Yfh1p and frataxin localize to the mitochondrial matrix. Yeast lacking Yfh1p exhibit decreased activities of mitochondrial iron-sulfur-cluster enzymes, impaired mitochondrial respiration, mitochondrial iron accumulation, and sensitivity to oxidative stress. The myocardium of patients with FRDA exhibits decreased activities of mitochondrial iron-sulfur-cluster enzymes—including respiratory complexes I, II, and III—as well as impaired mitochondrial bioenergetics. Cultured fibroblasts from patients with FRDA accumulate mitochondrial iron and are sensitive to oxidative stress.

The best-characterized function of Yfh1p and frataxin is in iron-sulfur-cluster assembly. Iron-sulfur clusters are prosthetic groups important for the function of many mitochondrial proteins—including aconitase and mitochondrial respiratory complexes I, II, and III—as well as for the function of a number of cytosolic proteins. Studies in yeast demonstrate that Yfh1p is important for the initial assembly of iron-sulfur clusters on the scaffold protein Isu1p. Regulated Yfh1p depletion decreases iron-sulfur-cluster assembly for mitochondrial and cytosolic iron-sulfur-cluster proteins in vivo, as well as in vitro using mitochondrial extracts. Using RNA electrophoretic mobility shift assays (REMSAs), it was found that in primary FRDA fibroblasts, the iron-sulfur-cluster form of the cytosolic protein IRP1 is decreased and the mRNA-binding form is increased relative to normal control fibroblasts. Hence, Yfh1p and frataxin likely play a central role in iron-sulfur-cluster assembly for both mitochondrial and cytosolic proteins.

The yeast model system used to identify compounds capable of improving mitochondrial function is described in detail in the examples below. As will be seen, active compounds produced statistically significant improvements in growth (>2-fold in shaking flasks by absorbance at 630 nm) and in ATP production (>3-fold by the CellTiter-Glo assay), demonstrating that the positive effects were not specific to tetrazolium dye reduction per se.

A further screen can be carried out to test the effects of overloading the murine myoblast cell line C2C12 with iron, using ferric ammonium citrate (FAC); of inhibiting the rate-limiting step of glutathione synthesis, using L-buthionine (S,R)-sulfoximine (BSO); and of combining the two at sublethal concentrations for each. Approximately 4000 cells per well are plated in standard medium in 96-well plates and FAC is added 4 hours later. The cells are incubated overnight (20 h) in standard tissue-culture incubators, after which BSO is added. After another overnight incubation (24 h) ATP content is determined using the CellTiter-Glo assay.

Thus, through the aforementioned screening, compounds with the following structural formula (I) are found to be active:

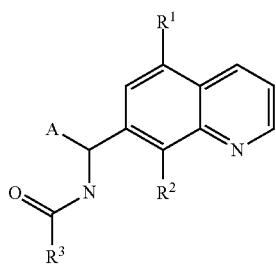

I wherein A is an optionally substituted aliphatic, alicyclic, heteroaliphatic, heterocyclic, aromatic, or heteroaromatic;

$R^1$ is hydrogen, hydroxy, halogen, cyano, alkyloxy, nitro, $NH_2$, $NHCOR^4$, $NHSO_2R^4$, $CONHR^4$, $COOR^4$, or an optionally substituted aliphatic, alicyclic, heteroaliphatic, heterocyclic, aromatic, or heteroaromatic;

$R^2$ is —OR, wherein R is —$C_1$-$C_6$-alkyl, —$C_2$-$C_6$-alkenyl, —$C_2$-$C_6$-alkynyl, —$SO_2NR^4R^6$, —$SO_2R^7$, —$COR^7$, —$COOR^7$ or —$CONR^4R^6$, wherein (a) one or more of the carbon atoms in the alkyl, alkenyl or alkynyl group is each independently optionally replaced with a nitrogen, sulfur or oxygen atom, and (b) the alkyl, alkenyl or alkynyl group is optionally substituted with a —$C_1$-$C_3$-alkyl;

$R^3$ is an optionally substituted aliphatic, alicyclic, heteroaliphatic, heterocyclic, aromatic, or heteroaromatic; and $R^4$ and $R^6$ are each independently hydrogen, —$C_1$-$C_6$-alkyl, —$C_2$-$C_6$-alkenyl, —$C_2$-$C_6$-alkynyl, —$COR^7$, —$C_5$-$C_7$-aryl, or —$C_5$-$C_{10}$-arylalkyl, wherein (a) one or more of the carbon atoms in the alkyl, alkenyl, alkynyl, aryl or arylalkyl group is each independently optionally replaced with a nitrogen, sulfur or oxygen atom, and (b) the alkyl, alkenyl, alkynyl, aryl or arylalkyl is optionally substituted with an oxygen, a —$C_1$-$C_3$-alkyl, or a —$C_5$-$C_7$-aryl; and $R^7$ is hydrogen, —$C_1$-$C_6$-alkyl, —$C_2$-$C_6$-alkenyl, —$C_2$-$C_6$-alkynyl, —$C_5$-$C_7$-aryl, or —$C_5$-$C_{10}$-arylalkyl, wherein (a) one or more of the carbon atoms in the alkyl, alkenyl, alkynyl, aryl or arylalkyl group is each independently optionally replaced with a nitrogen, sulfur or oxygen atom, and (b) the alkyl, alkenyl, alkynyl, aryl or arylalkyl is optionally substituted with a halogen, a —$C_1$-$C_3$-alkyl, a —$C_5$-$C_7$-aryl, or —$NR^4R^6$ or —$OR^4$;

or an isomer, stereoisomer, racemate, prodrug, active metabolite, metal chelate, or a pharmaceutically-acceptable derivative or salt form of any of the foregoing.

By way of non-limiting example, moiety A can be a substituted or unsubstituted heteroaryl group such as a thienyl, pyrrolyl or furyl group. In certain embodiments A is 2-thienyl. In other embodiments, A is a substituted or unsubstituted aryl group. In other embodiments A is phenyl. In other embodiments A is a heterocyclic group. In other embodiments A is substituted with one or more alkyl, alkoxy or halo groups, such as but not limited to methyl, methoxy or chloro. In certain embodiments A is 4-methylphenyl, 2-methoxyphenyl, or 3,4-dimethoxyphenyl.

In other embodiments, $R^3$ is aralkyl or alkyl. Non-limiting examples of aralkyl include phenyl, benzyl, phenylethyl, phenylpropyl, phenylbutyl and phenylpentyl. The foregoing aralkyl groups may be substituted on the aryl moiety, or on the alkyl moiety, or both. Non-limiting examples of alkyl include methyl, ethyl, n-propyl, 2-propyl, n-butyl, t-butyl, n-pentyl and n-hexyl.

Among the aforementioned compounds of formula (I), two groups of compounds of special interest are identified: formula (II) and formula (III).

In another embodiment, compounds useful for the purposes described herein throughout have the structure of formula (II) below:

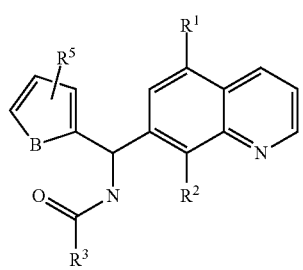

II wherein B is O, N or S;

$R^1$ is hydrogen, hydroxy, halogen, cyano, alkyloxy, nitro, $NH_2$, $NHCOR^4$, $NHSO_2R^4$, $CONHR^4$, $COOR^4$, or an optionally substituted aliphatic, alicyclic, heteroaliphatic, heterocyclic, aromatic, or heteroaromatic;

$R^2$ is —OR, wherein R is —$C_1$-$C_6$-alkyl, —$C_2$-$C_6$-alkenyl, —$C_2$-$C_6$-alkynyl, —$SO_2NR^4R^6$, —$SO_2R^7$, —$COR^7$, —$COOR^7$ or —$CONR^4R^6$, wherein (a) one or more of the carbon atoms in the alkyl, alkenyl or alkynyl group is each independently optionally replaced with a nitrogen, sulfur or oxygen atom, and (b) the alkyl, alkenyl or alkynyl group is optionally substituted with a —$C_1$-$C_3$-alkyl;

$R^3$ is an optionally substituted aliphatic, alicyclic, heteroaliphatic, heterocyclic, aromatic, or hetero aromatic;

$R^4$ and $R^6$ are each independently hydrogen, —$C_1$-$C_6$-alkyl, —$C_2$-$C_6$-alkenyl, —$C_2$-$C_6$-alkynyl, —$COR^7$, —$C_5$-$C_7$-aryl, or —$C_5$-$C_{10}$-arylalkyl, wherein (a) one or more of the carbon atoms in the alkyl, alkenyl, alkynyl, aryl or arylalkyl group is each independently optionally replaced with a nitrogen, sulfur or oxygen atom, and (b) the alkyl, alkenyl, alkynyl, aryl or arylalkyl is optionally substituted with an oxygen, a —$C_1$-$C_3$-alkyl, or a —$C_5$-$C_7$-aryl;

$R^5$ is one or more hydrogen, hydroxy, halogen, cyano, alkyloxy, nitro, $NH_2$, $NHCOR^4$, $NHSO_2R^4$, $CONHR^4$, $COOR^4$, optionally substituted aliphatic, alicyclic, heteroaliphatic, heterocyclic, aromatic, or heteroaromatic; and $R^7$ is hydrogen, —$C_1$-$C_6$-alkyl, —$C_2$-$C_6$-alkenyl, —$C_2$-$C_6$-alkynyl, —$C_5$-$C_7$-aryl, or —$C_5$-$C_{10}$-arylalkyl, wherein (a) one or more of the carbon atoms in the alkyl, alkenyl, alkynyl, aryl or arylalkyl group is each independently optionally replaced with a nitrogen, sulfur or oxygen atom, and (b) the alkyl, alkenyl, alkynyl, aryl or arylalkyl is optionally substituted with a halogen, a —$C_1$-$C_3$-alkyl, a —$C_5$-$C_7$-aryl, or —$NR^4R^6$ or —$OR^4$;

or an isomer, enantiomer, racemate, prodrug, active metabolite, metal chelate, or a pharmaceutically-acceptable derivative or salt form of any of the foregoing.

In certain embodiments, B is O. In other embodiments B is S. In further embodiments, $R^1$ can be hydroxy, nitro or halogen. In other embodiments $R^2$ can be hydroxy, nitro or cyano. In other embodiments, $R^3$ can be alkyl or aralkyl. In other embodiments $R^5$ is one or more alkyl, alkoxy or halo groups, such as but not limited to methyl, methoxy or chloro. Non-limiting examples of aralkyl include phenyl, benzyl and phenylethyl. The foregoing aralkyl groups may be substituted on the aryl moiety, or on the alkyl moiety, or both. Non-limiting examples of alkyl include methyl, ethyl, n-propyl, 2-propyl, n-butyl, t-butyl, n-pentyl and n-hexyl.

Non-limiting examples of such compounds include N-[(5-chloro-8-hydroxyquinolin-7-yl)-thiophen-2-ylmethyl]-3-phenylpropanamide, N-[(5-chloro-8-hydroxyquinolin-7-yl)-thiophen-2-ylmethyl]pentanamide, N-[(5-chloro-8-hydroxyquinolin-7-yl)-thiophen-2-ylmethyl]propanamide, N-[(5-chloro-8-hydroxyquinolin-7-yl)-thiophen-2-ylmethyl]-2-methylpropanamide, N-[(5-chloro-8-hydroxyquinolin-7-yl)-thiophen-2-ylmethyl]butanamide, N-[(5-chloro-8-hydroxyquinolin-7-yl)-thiophen-2-ylmethyl]acetamide, N-[(8-hydroxy-5-nitroquinolin-7-yl)-thiophen-2-ylmethyl]butanamide, N-[(8-hydroxy-5-nitro-quinolin-7-yl)-thiophen-2-yl-methyl]-acetamide, N-[(8-hydroxy-5-nitro-quinolin-7-yl)-thiophen-2-yl-methyl]-propionamide, N-[2-furyl(8-hydroxy-5-nitro-7-quinolinyl)methyl]butanamide, N-[(8-hydroxyquinolin-7-yl)-thiophen-2-ylmethyl]-3-phenylpropanamide, N-[(5-chloro-8-hydroxyquinolin-7-yl)-furan-2-ylmethyl]-3-phenylpropanamide, N-[(5-chloro-8-hydroxyquinolin-7-yl)-furan-2-ylmethyl]propanamide, and N-[(5-chloro-8-hydroxyquinolin-7-yl)-furan-2-ylmethyl]pentanamide.

In certain other embodiments, compound (I) has the structure of formula (III) below:

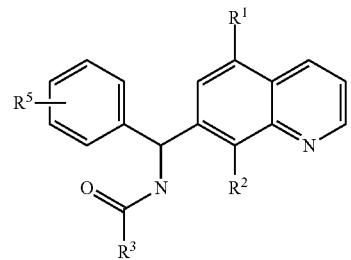

III wherein $R^1$ is hydrogen, hydroxy, halogen, cyano, alkyloxy, nitro, $NH_2$, $NHCOR^4$, $NHSO_2R^4$, $CONHR^4$, $COOR^4$, or an optionally substituted aliphatic, alicyclic, heteroaliphatic, heterocyclic, aromatic, or heteroaromatic;

$R^2$ is —OR, wherein R is —$C_1$-$C_6$-alkyl, —$C_2$-$C_6$-alkenyl, —$C_2$-$C_6$-alkynyl, —$SO_2NR^4R^6$, —$SO_2R^7$, —$COR^7$, —$COOR^7$ or —$CONR^4R^6$, wherein (a) one or more of the carbon atoms in the alkyl, alkenyl or alkynyl group is each independently optionally replaced with a nitrogen, sulfur or oxygen atom, and (b) the alkyl, alkenyl or alkynyl group is optionally substituted with a —$C_1$-$C_3$-alkyl;

$R^3$ is an optionally substituted aliphatic, alicyclic, heteroaliphatic, heterocyclic, aromatic, or hetero aromatic;

$R^4$ and $R^6$ are each independently hydrogen, —$C_1$-$C_6$-alkyl, —$C_2$-$C_6$-alkenyl, —$C_2$-$C_6$-alkynyl, —$COR^7$, —$C_5$-$C_7$-aryl, or —$C_5$-$C_{10}$-arylalkyl, wherein (a) one or more of the carbon atoms in the alkyl, alkenyl, alkynyl, aryl or arylalkyl group is each independently optionally replaced with a nitrogen, sulfur or oxygen atom, and (b) the alkyl, alkenyl, alkynyl, aryl or arylalkyl is optionally substituted with an oxygen, a —$C_1$-$C_3$-alkyl, or a —$C_5$-$C_7$-aryl;

$R^5$ is one or more hydrogen, hydroxy, halogen, cyano, alkyloxy, nitro, $NH_2$, $NHCOR^4$, $NHSO_2R^4$, $CONHR^4$, $COOR^4$, optionally substituted aliphatic, alicyclic, heteroaliphatic, heterocyclic, aromatic, or heteroaromatic; and $R^7$ is hydrogen, —$C_1$-$C_6$-alkyl, —$C_2$-$C_6$-alkenyl, —$C_2$-$C_6$-alkynyl, —$C_5$-$C_7$-aryl, or —$C_5$-$C_{10}$-arylalkyl, wherein (a) one or more of the carbon atoms in the alkyl, alkenyl, alkynyl, aryl or arylalkyl group is each independently optionally replaced with a nitrogen, sulfur or oxygen atom, and (b) the alkyl, alkenyl, alkynyl, aryl or arylalkyl is optionally substituted with a halogen, a —$C_1$-$C_3$-alkyl, a —$C_5$-$C_7$-aryl, or —$NR^4R^6$ or —$OR^4$;

or an isomer, enantiomer, racemate, prodrug, active metabolite, metal chelate, or a pharmaceutically-acceptable derivative or salt form of any of the foregoing.

In certain embodiments, $R^1$ can be hydroxy, nitro or halogen. In certain embodiments $R^2$ can be hydroxy, nitro or cyano. In other embodiments, $R^5$ can be one or more alkyl, alkoxy, halo or dimethylamino groups. In other embodiments $R^3$ is alkyl or aralkyl. Non-limiting examples of aralkyl include phenyl, benzyl and phenylethyl. The foregoing aralkyl groups may be substituted on the aryl moiety, or on the alkyl moiety, or both. Non-limiting examples of alkyl include methyl, ethyl, n-propyl, 2-propyl, n-butyl, t-butyl, n-pentyl and n-hexyl.

Non-limiting examples of such compounds include N-[(5-chloro-8-hydroxyquinolin-7-yl)-(3,4-dimethoxyphenyl)methyl]propanamide, N-[(5-chloro-8-hydroxyquinolin-7-yl)-(4-methoxyphenyl)methyl]propanamide, N-[(5-chloro-8-hydroxyquinolin-7-yl)-tolyl]-3-phenylpropanamide, N-[(5-chloro-8-hydroxyquinolin-7-yl)-(3-methoxyphenyl)methyl]-3-phenylpropanamide, N-[(5-chloro-8-hydroxyquinolin-7-yl)-(4-dimethylaminophenyl)methyl]-3-phenylpropanamide, N-[(5-chloro-8-hydroxyquinolin-7-yl)-(4-chlorophenyl)methyl]-3-phenylpropanamide, N-[(5-chloro-8-hydroxyquinolin-7-yl)-(3-chlorophenyl)methyl]-3-phenylpropanamide, N-[(5-chloro-8-hydroxyquinolin-7-yl)-(2-chlorophenyl)methyl]-3-phenylpropanamide, N-[(5-chloro-8-hydroxyquinolin-7-yl)-(3,4-dimethoxyphenyl)methyl]-3-phenylpropanamide, N-[(5-chloro-8-hydroxyquinolin-7-yl)-(2,4-dimethoxyphenyl)methyl]-3-phenylpropanamide, N-[(5-chloro-8-hydroxyquinolin-7-yl)-(3,4,5-trimethoxyphenyl)methyl]-3-phenylpropanamide, N-[(5-chloro-8-hydroxyquinolin-7-yl)-(2-bromophenyl)methyl]-3-phenylpropanamide, N-[(5-chloro-8-hydroxyquinolin-7-yl)-p-tolyl-methyl]-3-phenylpropanamide, N-[(5-chloro-8-hydroxyquinolin-7-yl)-(2-hydroxyphenyl)methyl]-3-phenylpropanamide, N-[(5-chloro-8-hydroxyquinolin-7-yl)-(4-methoxyphenyl)methyl]-3-phenylpropanamide, N-[(8-Hydroxy-5-nitro-quinolin-7-yl)-p-tolyl-methyl]-propionamide, N-[{8-hydroxy-5-nitro-7-quinolinyl}(4-methylphenyl)methyl]acetamide, and N-[(8-hydroxyquinolin-7-yl)-(2-methoxyphenyl)methyl]pentanamide.

In still yet a further embodiment, a method is provided for identifying a step in mitochondrial function or cellular respiration upstream from or regulated by frataxin activity or its phenotypic equivalent, and for identifying candidate activity modulators of such step. In this embodiment, compounds embodied herein may be described or referred to as probes. In one embodiment, the method comprises determining the effect on mitochondrial function or cellular respiration of at least one candidate modulator in cells that are frataxin deficient, frataxin-mutated, or in frataxin knockout cells, in the presence and absence of a compound of formula (I):

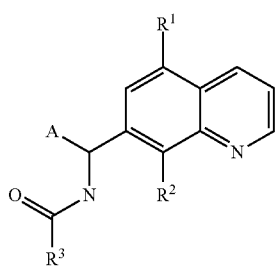

I wherein A is an optionally substituted aliphatic, alicyclic, heteroaliphatic, heterocyclic, aromatic, or heteroaromatic;

$R^1$ is hydrogen, hydroxy, halogen, cyano, alkyloxy, nitro, $NH_2$, $NHCOR^4$, $NHSO_2R^4$, $CONHR^4$, $COOR^4$, or an optionally substituted aliphatic, alicyclic, heteroaliphatic, heterocyclic, aromatic, or heteroaromatic;

$R^2$ is —OR, wherein R is —$C_1$-$C_6$-alkyl, —$C_2$-$C_6$-alkenyl, —$C_2$-$C_6$-alkynyl, —$SO_2NR^4R^6$, —$SO_2R^7$, —$COR^7$, —$COOR^7$ or —$CONR^4R^6$, wherein (a) one or more of the carbon atoms in the alkyl, alkenyl or alkynyl group is each independently optionally replaced with a nitrogen, sulfur or oxygen atom, and (b) the alkyl, alkenyl or alkynyl group is optionally substituted with a —$C_1$-$C_3$-alkyl;

$R^3$ is an optionally substituted aliphatic, alicyclic, heteroaliphatic, heterocyclic, aromatic, or heteroaromatic; and $R^4$ and $R^6$ are each independently hydrogen, —$C_1$-$C_6$-alkyl, —$C_2$-$C_6$-alkenyl, —$C_2$-$C_6$-alkynyl, —$COR^7$, —$C_5$-$C_7$-aryl, or —$C_5$-$C_{10}$-arylalkyl, wherein (a) one or more of the carbon atoms in the alkyl, alkenyl, alkynyl, aryl or arylalkyl group is each independently optionally replaced with a nitrogen, sulfur or oxygen atom, and (b) the alkyl, alkenyl, alkynyl, aryl or arylalkyl is optionally substituted with an oxygen, a —$C_1$-$C_3$-alkyl, or a —$C_5$-$C_7$-aryl; and $R^7$ is hydrogen, —$C_1$-$C_6$-alkyl, —$C_2$-$C_6$-alkenyl, —$C_2$-$C_6$-alkynyl, —$C_5$-$C_7$-aryl, or —$C_5$-$C_{10}$-arylalkyl, wherein (a) one or more of the carbon atoms in the alkyl, alkenyl, alkynyl, aryl or arylalkyl group is each independently optionally replaced with a nitrogen, sulfur or oxygen atom, and (b) the alkyl, alkenyl, alkynyl, aryl or arylalkyl is optionally substituted with a halogen, a —$C_1$-$C_3$-alkyl, a —$C_5$-$C_7$-aryl, or —$NR^4R^6$ or —$OR^4$;

or an isomer, stereoisomer, racemate, prodrug, active metabolite, metal chelate, or a pharmaceutically-acceptable derivative or salt form of any of the foregoing.

Non-limiting examples of various embodiments and compounds in formulas (I), (II) and (III) are mentioned hereinabove.

In a further embodiment, the effect of the at least one candidate modulator on mitochondrial function, iron homeostasis or cellular respiration in the presence and absence of the compound of formula (I) is correlated with the relationship of the step to that of frataxin activity, its role in regulation thereof, and identification of a modulator thereof. In a further embodiment, the at least one candidate modulator of the step is a compound that modulates activity of the step, or a mutation that modulates the step, or the combination thereof. In another embodiment, the mutation inhibits the step and the compound is a candidate activator of or phenotypic substitute for the step. In another embodiment, the frataxin deficient, frataxin-mutated, or frataxin knockout cells are yeast cells or mammalian cells, and in further embodiments, the yeast cells have at least one gene encoding a protein catalyzing or regulating the step knocked out or regulated by an inducible promoter; or the yeast cells also have the frataxin gene knocked out or regulated by an inducible promoter. In another embodiment, the compound has formula (II) or formula (III) as described hereinabove, or any embodiment thereof.

In the foregoing method, at least one candidate modulator of said step can a compound that modulates activity of said step, or a mutation that modulates said step, or the combination thereof. In another embodiment, the mutation inhibits said step and the compound is a candidate activator of or phenotypic substitute for said step. By way of non-limiting examples, the frataxin deficient, frataxin-mutated, or frataxin knockout cells are yeast cells or mammalian cells. In one embodiment, the yeast cells have at least one gene encoding a protein catalyzing or regulating a step knocked out or regulated by an inducible promoter. In another embodiment the yeast cells also have the frataxin gene knocked out or regulated by an inducible promoter. In another embodiment, the cells are mammalian cells, and in a further embodiment have a mutation in the frataxin gene or another defect in frataxin expression. In another embodiment, the mammalian cells are from a patient having FRDA.

The foregoing method is best illustrated by a non-limiting example. As mentioned above, a screening assay using a yeast model system allows for the rapid and facile identification of compounds capable of restoring mitochondrial dysfunction in cells deficient in frataxin, as well as identify compounds capable of improving mitochondrial function in general. Such methods are amenable for the identification and use of probes having the structure of formula (I) that give insight into specific steps within mitochondrial metabolism, such as but not limited to the mitochondrial electron transport chain (ETC). With the demonstration of an important role for mitochondrial dysfunction in normal aging, and in the pathophysiology of Alzheimer's Disease, Parkinson's Disease, age-related macular degeneration, and type II diabetes, as well as of rare diseases such as FRDA and the mitochondrial encephalomyopathies, the embodiment herein of probe development facilitates identifying pathways and then compounds that can address such important diseases and be useful therapeutically or prophylactically.

In one embodiment, a probe identified as described herein takes advantage of the fact that the yeast protein Yfh1p is a functional homologue of the FRDA disease protein, and that compounds of formula (I) herein overcomes the defect in Yfh1p conditional knock-out cells or cells lacking Yfh1p. In another embodiment, the functional homology of the two proteins allows drug screening initially using a yeast model system for FRDA, and, of particular relevance, libraries of yeast strains in which another gene in the yeast genome has been independently knocked out. This permits, in another embodiment, to determine target pathways and proteins affected by compounds in the yeast screen that are also active in human cells.

In the practice of this embodiment, the following steps are carried out:

1. Conduct the primary screen in the yeast model of FRDA, as described above and in the Examples, using WST reduction, to identify compounds that improve mitochondrial function.
2. Carry out a secondary screen in mammalian cells treated with ferric ammonium citrate (FAC) and L-buthionine (S,R)-sulfoximine (BSO), using ATP measurements, to identify those compounds identified in step (1) above that are active in human or other mammalian cells.
3. Evaluate active compounds from step (2) above in yeast lacking functional mitochondrial complex V, using ATP measurements, to identify compounds that act in the ETC. Compounds that depend on complex V for at least 50% of their activity will be carried through to step 4.
4. Evaluate active compounds from step (3) above in yeast lacking functional mitochondrial complexes I, II, III, and IV to identify specific sites of action within the ETC. Determine that activity is dependent on a specific ETC respiratory complex.
5. Evaluate compounds from step (4) above in mammalian cells treated with inhibitors of specific complexes of the ETC to confirm sites of action of compounds studied in steps 3 and 4. Confirm activity is dependent on a specific respiratory complex.

Moreover, additional screens can be performed on the compounds:

1. Evaluate compounds in HepG2 cells to determine if they can be rescued from lethal or sublethal concentrations of ferric ammonium citrate (FAC) and/or L-buthionine (S,R)-sulfoximine (BSO).
2. Evaluate compounds in the I154F frataxin point-mutation model, to determine if cells can be rescued from a lethal or sublethal concentration of FAC and/or BSO.
3. Evaluate compounds in the I154F frataxin point-mutation model, to determine if mitochondrial function can be improved, or if mitochondrial iron or oxidative stress can be decreased, or if any other phenotype associated with decreased or impaired frataxin function can be partially or fully reversed.
4. Evaluate the catalytic activity of the compound by preloading with manganese or iron or other metal and assaying superoxide dismutase or catalase activity in vitro.

As a result, a probe or therapeutic compound is identified that acts upon a specific ETC complex. Each of the foregoing steps is described in more detail below. While the screening in the order mentioned below and including all of the steps is typically performed, it is not necessary to do so and active compounds can be identified using a subset of the assays mentioned, from one assay to any combination of any number of assays, in any order.

Step 1. Primary Screening. The primary yeast screen is described above and in Examples 1 and 2 below.

Step 2. Secondary Screening. The secondary screen employs mammalian (C2C12) cells treated with ferric ammonium citrate (FAC) and/or L-buthionine (S,R)-sulfoximine (BSO), using ATP measurements. Approximately 4000 cells per well were plated in standard medium in 96-well plates and FAC was added 4 hours later. The cells were incubated overnight (20 h) in standard tissue-culture incubators, after which BSO was added. After another overnight incubation (24 h) ATP content was determined using the CellTiter-Glo assay. The synergistic effects of FAC and BSO presumably derived from the combination of increased oxidative stress (secondary to the FAC) with decreased cellular antioxidant capacity (secondary to the BSO).

Step 3. Screening in yeast lacking functional complex V. The effects of several compounds on ATP content in yeast (using the CellTiter-Glo assay) with and without ATP15p, which is required for the function of complex V. Active compounds generally increase ATP dramatically within minutes; the differences from carrier controls diminish with time and equalize over the course of days. These results suggest a pent-up demand for ATP, a burst of new synthesis, and a gradual return to equilibrium levels, which are normally maintained within a fairly narrow range by feedback mechanisms. Compounds that depend on complex V for at least 50% of their activity are carried through to step 4.

Step 4. Screening in yeast lacking functional mitochondrial complexes I, II, III, and IV. Relative to carrier controls, treatment of cells completely lacking Ndi1 (which encodes the yeast equivalent of complex I) with active compounds can induce an increase of ATP of up to 25-fold or more within minutes. The differences from carrier controls diminish with time and equalize over the course of days, suggesting a pent-up demand for ATP, a burst of new synthesis, and a gradual return to equilibrium levels.

Step 5. Screening in mammalian cells treated with inhibitors of specific complexes of the ETC. Rotenone, antimycin A, and oligomycin have been used in experiments with primary FRDA fibroblasts to show that rotenone inhibits complex I in SH-SY5Y cells in the nM range, and kills SH-SY5Y cells in the $\mu$M range (with 90% death, as assessed by trypan blue exclusion, after 7 days at 60 $\mu$M). Antimycin A and oligomycin kill SH-SY5Y cells in the high nM range, as assessed by LDH leakage and DNA fragmentation.

The additional screens are described in more detail below.

1. This assay is employed to determine whether test compound can rescue HepG2 cells from lethal concentrations of FAC+BSO. In addition to the C2C12 assay described herein, the human hepatocellular carcinoma line HepG2, is treated with ferric ammonium citrate (FAC) and/or L-buthionine (S,R)-sulfoximine (BSO), which inhibits the rate-limiting step of glutathione synthesis. A finding of a low effective concentration can support a mechanism other than iron chelation, such as a catalytic mechanism, such as mimicking SOD and/or catalase.

2. Preliminary testing in the I154F frataxin point-mutation model determines whether test compounds can rescue I154F FA cells from lethal concentrations of FAC and/or BSO. Among the mammalian-cell models that have, or recapitulate, the genetic defects underlying FA, by far the most robust (and best validated) is the I154F murine frataxin point-mutation model developed by Puccio and colleagues (Calmels, N. et al.), the first cellular model based on frataxin missense mutations that reproduces spontaneously the defects associated with Friedreich ataxia (PLoS One 4, e6379 (2009)). This model exhibits all the hallmarks of FA, including mitochondrial iron accumulation, loss of iron-sulfur-cluster-enzyme activities, and sensitivity to iron and oxidative stress. This model is also extremely stable, with phenotypes unchanged after months of continuous culture. In contrast, the mutations in available primary human FA fibroblasts are GAA repeat expansions in the first intron of the FXN gene; occasional cells in which these expansions contract have a growth advantage and take over the culture, diluting the phenotype and increasing variance in various measures of compound efficacy. Also in contrast, the RNAi models tend to have weak phenotypes and, like the human FA fibroblasts, to exhibit a high variability in culture.

3. Evaluate the catalytic activity of the compound by preloading with manganese, iron, or other metal and assaying superoxide dismutase and/or catalase activity in vitro. This assay helps identify a possible mechanism of action that would help explain the unusual combination of high potency, and high specificity, of the compounds embodied herein. A picomolar potency in cell-based assays can suggest that compounds are acting catalytically. Yet compounds that act catalytically are usually relatively non-specific, whereas the compounds embodied herein were confirmed active in only one assay (the FA yeast assay mentioned above) of 168 high-throughput screening assays in which they have been tested to date. With no duty to disclose the mechanism of action of the compounds embodied here and without being bound based thereon, it is hypothesized that the compounds embodied herein are chelating iron within cells and acting as superoxide dismutase (SOD) and/or catalase mimetics.

As will be seen in the examples below, compounds embodied herein display a high level of potency, with significant activity in the picomolar range in mammalian cells, and high specificity. Based on the results of the screening, and preliminary testing, compounds embodied herein are hypothesized to become activated to mimic superoxidase and/or catalase activity only in cells containing excess levels of labile iron. Because diseases described herein such as Friedreich's ataxia have pathophysiological mechanisms arising from increased intracellular iron, such compounds are particularly suitable for their prophylaxis or treatment, and also such a mechanism can offer benefit in other diseases in which iron accumulation and attendant oxidative stress contribute to the pathophysiology. Thus, in another embodiment, a compounds and methods are provided for decreasing intracellular iron by exposing the cells to a compound described herein. In another embodiment, a compounds and methods are provided for decreasing intramitochondrial iron by exposing the cells to a compound described herein. In another embodiment, compounds and methods are provided for decreasing intracellular and/or intramitochondrial oxidative stress by exposing the cells to a compound described herein. In another embodiment, compounds and methods are provided for decreasing mitochondrial dysfunction by exposing the cells to a compound described herein.

In another embodiment, a method is provided for identifying cells, tissues, or cells or tissues from a subject that may have a defect in mitochondrial function, cellular respiration upstream from or regulated by frataxin activity or the phenotype thereof. Such cells might be from a patient or subject with a predisposition to a disease such as any of those mentioned herein. In the practice of the method, the effect on mitochondrial function or cellular respiration in the cells or tissues by a compound of formula (I) or a pharmaceutical composition thereof is performed, following the teachings herein. If a compounds of the invention is found to improve mitochondrial function or cellular respiration, this result provides evidence that the cells or tissues as have a defect in mitochondrial function or cellular respiration. The patient or subject may be started on therapy to treat or prophylaxe the disease, such as by treatment with a compound described herein.

In another embodiment, the compound of formula (I) for the aforementioned method can have a structure of formula (II) or (III) or any of the compounds described hereinabove.

In another embodiment, the compounds described herein are activated by binding to a metal ion such as iron (II) or iron (III), or in other embodiments, manganese ion, such as Mn (II), (III), (IV), (VI) or (VII). Other metal cations are encompassed herein. Studies described herein suggest that the compounds embodied here are precursors of the active form of the molecule that reduces oxidative stress, decreases mitochondrial iron accumulation, and improves the cellular metabolism of cells with iron accumulation. In another embodiment, the compounds embodied herein become activated to catalyze the degradation of superoxide or hydrogen peroxide. As such, compounds described herein may be considered active form precursors of superoxide dismutase or catalase. While Applicants have no duty to disclose the mechanism by which the compounds operate and are not restricted thereto, the mechanism for the biological activity of the compounds provide a rationale for their high specificity and potency.

Compounds, Pharmaceutical Compositions and Methods of Administration

Another embodiment herein comprises compounds and pharmaceutical compositions of such compounds useful for the purposes described herein, but not limited thereto, that have the structure of formula (I):

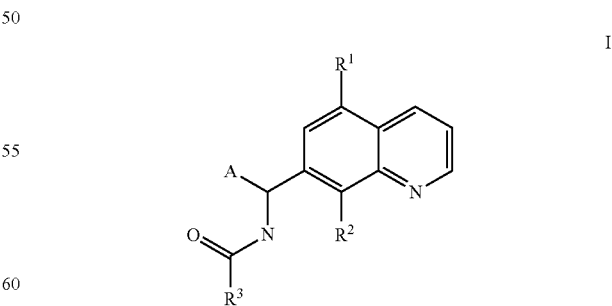

wherein A is an optionally substituted aliphatic, alicyclic, heteroaliphatic, heterocyclic, aromatic, or heteroaromatic;

$R^1$ is hydrogen, hydroxy, halogen, cyano, alkyloxy, nitro, $NH_2$, $NHCOR^4$, $NHSO_2R^4$, $CONHR^4$, $COOR^4$, or an optionally substituted aliphatic, alicyclic, heteroaliphatic, heterocyclic, aromatic, or heteroaromatic;

$R^2$ is —OR, wherein R is —$C_1$-$C_6$-alkyl, —$C_2$-$C_6$-alkenyl, —$C_2$-$C_6$-alkynyl, —$SO_2NR^4R^6$, —$SO_2R^7$, —$COR^7$, —$COOR^7$ or —$CONR^4R^6$, wherein (a) one or more of the carbon atoms in the alkyl, alkenyl or alkynyl group is each independently optionally replaced with a nitrogen, sulfur or oxygen atom, and (b) the alkyl, alkenyl or alkynyl group is optionally substituted with a —$C_1$-$C_3$-alkyl;

$R^3$ is an optionally substituted aliphatic, alicyclic, heteroaliphatic, heterocyclic, aromatic, or heteroaromatic; and $R^4$ and $R^6$ are each independently hydrogen, —$C_1$-$C_6$-alkyl, —$C_2$-$C_6$-alkenyl, —$C_2$-$C_6$-alkynyl, —$COR^7$, —$C_5$-$C_7$-aryl, or —$C_5$-$C_{10}$-arylalkyl, wherein (a) one or more of the carbon atoms in the alkyl, alkenyl, alkynyl, aryl or arylalkyl group is each independently optionally replaced with a nitrogen, sulfur or oxygen atom, and (b) the alkyl, alkenyl, alkynyl, aryl or arylalkyl is optionally substituted with an oxygen, a —$C_1$-$C_3$-alkyl, or a —$C_5$-$C_7$-aryl; and $R^7$ is hydrogen, —$C_1$-$C_6$-alkyl, —$C_2$-$C_6$-alkenyl, —$C_2$-$C_6$-alkynyl, —$C_5$-$C_7$-aryl, or —$C_5$-$C_{10}$-arylalkyl, wherein (a) one or more of the carbon atoms in the alkyl, alkenyl, alkynyl, aryl or arylalkyl group is each independently optionally replaced with a nitrogen, sulfur or oxygen atom, and (b) the alkyl, alkenyl, alkynyl, aryl or arylalkyl is optionally substituted with a halogen, a —$C_1$-$C_3$-alkyl, a —$C_5$-$C_7$-aryl, or —$NR^4R^6$ or —$OR^4$;

or an isomer, stereoisomer, racemate, prodrug, active metabolite, metal chelate, or a pharmaceutically-acceptable derivative or salt form of any of the foregoing.

In certain embodiments, $R^1$ is chloro, nitro or cyano. In other embodiments $R^2$ is hydroxy. In other embodiments, A is a substituted aryl group or an optionally substituted furyl group. In further embodiments, $R^3$ is an optionally substituted alkyl or aralkyl group. Non-limiting examples of aralkyl include phenyl, benzyl, phenylethyl, phenylpropyl, phenylbutyl and phenylpentyl. The foregoing aralkyl groups may be substituted on the aryl moiety, or on the alkyl moiety, or both. Non-limiting examples of alkyl include methyl, ethyl, n-propyl, 2-propyl, n-butyl, t-butyl, n-pentyl and n-hexyl. By way of non-limiting example, moiety A can be a substituted or unsubstituted heteroaryl group such as a thienyl, pyrrolyl or furyl group. In certain embodiments A is 2-thienyl. In other embodiments, A is a substituted or unsubstituted aryl group. In other embodiments A is phenyl. In other embodiments A is a heterocyclic group. In other embodiments A is substituted with one or more alkyl, alkoxy or halo groups, such as but not limited to methyl, methoxy or chloro. In certain embodiments A is 4-methylphenyl, 2-methoxyphenyl, or 3,4-dimethoxyphenyl.

In certain embodiments, the compound of formula (I) has the structure of formula (II):

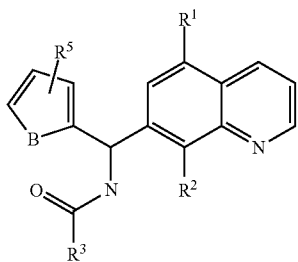

II wherein B is O, N or S;

$R^1$ is hydrogen, hydroxy, halogen, cyano, alkyloxy, nitro, $NH_2$, $NHCOR^4$, $NHSO_2R^4$, $CONHR^4$, $COOR^4$, or an optionally substituted aliphatic, alicyclic, heteroaliphatic, heterocyclic, aromatic, or heteroaromatic;

$R^2$ is —OR, wherein R is —$C_1$-$C_6$-alkyl, —$C_2$-$C_6$-alkenyl, —$C_2$-$C_6$-alkynyl, —$SO_2NR^4R^6$, —$SO_2R^7$, —$COR^7$, —$COOR^7$ or —$CONR^4R^6$, wherein (a) one or more of the carbon atoms in the alkyl, alkenyl or alkynyl group is each independently optionally replaced with a nitrogen, sulfur or oxygen atom, and (b) the alkyl, alkenyl or alkynyl group is optionally substituted with a —$C_1$-$C_3$-alkyl;

$R^3$ is an optionally substituted aliphatic, alicyclic, heteroaliphatic, heterocyclic, aromatic, or hetero aromatic;

$R^4$ and $R^6$ are each independently hydrogen, —$C_1$-$C_6$-alkyl, —$C_2$-$C_6$-alkenyl, —$C_2$-$C_6$-alkynyl, —$COR^7$, —$C_5$-$C_7$-aryl, or —$C_5$-$C_{10}$-arylalkyl, wherein (a) one or more of the carbon atoms in the alkyl, alkenyl, alkynyl, aryl or arylalkyl group is each independently optionally replaced with a nitrogen, sulfur or oxygen atom, and (b) the alkyl, alkenyl, alkynyl, aryl or arylalkyl is optionally substituted with an oxygen, a —$C_1$-$C_3$-alkyl, or a —$C_5$-$C_7$-aryl;

$R^5$ is one or more hydrogen, hydroxy, halogen, cyano, alkyloxy, nitro, $NH_2$, $NHCOR^4$, $NHSO_2R^4$, $CONHR^4$, $COOR^4$, optionally substituted aliphatic, alicyclic, heteroaliphatic, heterocyclic, aromatic, or heteroaromatic; and $R^7$ is hydrogen, —$C_1$-$C_6$-alkyl, —$C_2$-$C_6$-alkenyl, —$C_2$-$C_6$-alkynyl, —$C_5$-$C_7$-aryl, or —$C_5$-$C_{10}$-arylalkyl, wherein (a) one or more of the carbon atoms in the alkyl, alkenyl, alkynyl, aryl or arylalkyl group is each independently optionally replaced with a nitrogen, sulfur or oxygen atom, and (b) the alkyl, alkenyl, alkynyl, aryl or arylalkyl is optionally substituted with a halogen, a —$C_1$-$C_3$-alkyl, a —$C_5$-$C_7$-aryl, or —$NR^4R^6$ or —$OR^4$;

or an isomer, enantiomer, racemate, prodrug, active metabolite, metal chelate, or a pharmaceutically-acceptable derivative or salt form of any of the foregoing.

In certain embodiments, B is O. In other embodiments B is S. In further embodiments, $R^1$ can be hydroxy, nitro or halogen. In other embodiments $R^2$ can be hydroxy or methoxy. In other embodiments, $R^3$ can be alkyl or aralkyl. In other embodiments $R^5$ is one or more alkyl, alkoxy or halo groups, such as but not limited to methyl, methoxy or chloro. Non-limiting examples of aralkyl include phenyl, benzyl and phenylethyl. The foregoing aralkyl groups may be substituted on the aryl moiety, or on the alkyl moiety, or both. Non-limiting examples of alkyl include methyl, ethyl, n-propyl, 2-propyl, n-butyl, t-butyl, n-pentyl and n-hexyl.

Non-limiting examples of such compounds include N-[(5-chloro-8-hydroxyquinolin-7-yl)-thiophen-2-ylmethyl]-3-phenylpropanamide, N-[(5-chloro-8-hydroxyquinolin-7-yl)-thiophen-2-ylmethyl]pentanamide, N-[(5-chloro-8-hydroxyquinolin-7-yl)-thiophen-2-ylmethyl]propanamide, N-[(5-chloro-8-hydroxyquinolin-7-yl)-thiophen-2-ylmethyl]-2-methylpropanamide, N-[(5-chloro-8-hydroxyquinolin-7-yl)-thiophen-2-ylmethyl]butanamide, N-[(5-chloro-8-hydroxyquinolin-7-yl)-thiophen-2-ylmethyl] acetamide, N-[(8-hydroxy-5-nitroquinolin-7-yl)-thiophen-2-ylmethyl]butanamide, N-[(8-hydroxy-5-nitro-quinolin-7-yl)-thiophen-2-yl-methyl]-acetamide, N-[(8-hydroxy-5-nitro-quinolin-7-yl)-thiophen-2-yl-methyl]-propionamide, N-[2-furyl(8-hydroxy-5-nitro-7-quinolinyl)methyl]butanamide, N-[(8-hydroxyquinolin-7-yl)-thiophen-2-ylmethyl]-3-phenylpropanamide, N-[(5-chloro-8-hydroxyquinolin-7-yl)- furan-2-ylmethyl]-3-phenylpropanamide, N-[(5-chloro-8-hydroxyquinolin-7-yl)-furan-2-ylmethyl]propanamide, and N-[(5-chloro-8-hydroxyquinolin-7-yl)-furan-2-ylmethyl]pentanamide.

In certain other embodiments, compound (I) has the structure of formula (III)

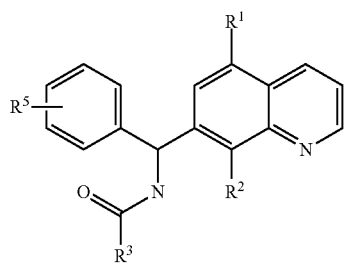

III wherein $R^1$ is hydrogen, hydroxy, halogen, cyano, alkyloxy, nitro, $NH_2$, $NHCOR^4$, $NHSO_2R^4$, $CONHR^4$, $COOR^4$, or an optionally substituted aliphatic, alicyclic, heteroaliphatic, heterocyclic, aromatic, or heteroaromatic;

$R^2$ is —OR, wherein R is —$C_1$-$C_6$-alkyl, —$C_2$-$C_6$-alkenyl, —$C_2$-$C_6$-alkynyl, —$SO_2NR^4R^6$, —$SO_2R^7$, —$COR^7$, —$COOR^7$ or —$CONR^4R^6$, wherein (a) one or more of the carbon atoms in the alkyl, alkenyl or alkynyl group is each independently optionally replaced with a nitrogen, sulfur or oxygen atom, and (b) the alkyl, alkenyl or alkynyl group is optionally substituted with a —$C_1$-$C_3$-alkyl;

$R^3$ is an optionally substituted aliphatic, alicyclic, heteroaliphatic, heterocyclic, aromatic, or hetero aromatic;

$R^4$ and $R^6$ are each independently hydrogen, —$C_1$-$C_6$-alkyl, —$C_2$-$C_6$-alkenyl, —$C_2$-$C_6$-alkynyl, —$COR^7$, —$C_5$-$C_7$-aryl, or —$C_5$-$C_{10}$-arylalkyl, wherein (a) one or more of the carbon atoms in the alkyl, alkenyl, alkynyl, aryl or arylalkyl group is each independently optionally replaced with a nitrogen, sulfur or oxygen atom, and (b) the alkyl, alkenyl, alkynyl, aryl or arylalkyl is optionally substituted with an oxygen, a —$C_1$-$C_3$-alkyl, or a —$C_5$-$C_7$-aryl;

$R^5$ is one or more hydrogen, hydroxy, halogen, cyano, alkyloxy, nitro, $NH_2$, $NHCOR^4$, $NHSO_2R^4$, $CONHR^4$, $COOR^4$, optionally substituted aliphatic, alicyclic, heteroaliphatic, heterocyclic, aromatic, or heteroaromatic; and $R^7$ is hydrogen, —$C_1$-$C_6$-alkyl, —$C_2$-$C_6$-alkenyl, —$C_2$-$C_6$-alkynyl, —$C_5$-$C_7$-aryl, or —$C_5$-$C_{10}$-arylalkyl, wherein (a) one or more of the carbon atoms in the alkyl, alkenyl, alkynyl, aryl or arylalkyl group is each independently optionally replaced with a nitrogen, sulfur or oxygen atom, and (b) the alkyl, alkenyl, alkynyl, aryl or arylalkyl is optionally substituted with a halogen, a —$C_1$-$C_3$-alkyl, a —$C_5$-$C_7$-aryl, or —$NR^4R^6$ or —$OR^4$;

or an isomer, enantiomer, racemate, prodrug, active metabolite, metal chelate, or a pharmaceutically-acceptable derivative or salt form of any of the foregoing.

In certain embodiments, $R^1$ is chloro, nitro or cyano. In other embodiments $R^2$ is hydroxy or methoxy. In other embodiments, $R^3$ can be alkyl or aralkyl. In other embodiments $R^3$ is alkyl or aralkyl. Non-limiting examples of aralkyl include phenyl, benzyl and phenylethyl. The foregoing aralkyl groups may be substituted on the aryl moiety, or on the alkyl moiety, or both. Non-limiting examples of alkyl include methyl, ethyl, n-propyl, 2-propyl, n-butyl, t-butyl, n-pentyl and n-hexyl. In other embodiments, $R^5$ can be one or more alkyl, alkoxy, halo or dimethylamino groups.

In certain embodiments, $R^1$ is chloro and $R^2$ is hydroxy. In other embodiments, $R^5$ is one or more methoxy, hydroxy, halo, or dimethylamino groups.

Non-limiting examples of such compounds include N-[(5-chloro-8-hydroxyquinolin-7-yl)-(3,4-dimethoxyphenyl)methyl]propanamide, N-[(5-chloro-8-hydroxyquinolin-7-yl)-(4-methoxyphenyl)methyl]propanamide, N-[(5-chloro-8-hydroxyquinolin-7-yl)-tolyl]-3-phenylpropanamide, N-[(5-chloro-8-hydroxyquinolin-7-yl)-(3-methoxyphenyl)methyl]-3-phenylpropanamide, N-[(5-chloro-8-hydroxyquinolin-7-yl)-(4-dimethylaminophenyl)methyl]-3-phenylpropanamide, N-[(5-chloro-8-hydroxyquinolin-7-yl)-(4-chlorophenyl)methyl]-3-phenylpropanamide, N-[(5-chloro-8-hydroxyquinolin-7-yl)-(3-chlorophenyl)methyl]-3-phenylpropanamide, N-[(5-chloro-8-hydroxyquinolin-7-yl)-(2-chlorophenyl)methyl]-3-phenylpropanamide, N-[(5-chloro-8-hydroxyquinolin-7-yl)-(3,4-dimethoxyphenyl)methyl]-3-phenylpropanamide, N-[(5-chloro-8-hydroxyquinolin-7-yl)-(2,4-dimethoxyphenyl)methyl]-3-phenylpropanamide, N-[(5-chloro-8-hydroxyquinolin-7-yl)-(3,4,5-trimethoxyphenyl)methyl]-3-phenylpropanamide, N-[(5-chloro-8-hydroxyquinolin-7-yl)-(2-bromophenyl)methyl]-3-phenylpropanamide, N-[(5-chloro-8-hydroxyquinolin-7-yl)-p-tolyl-methyl]-3-phenylpropanamide, N-[(5-chloro-8-hydroxyquinolin-7-yl)-(2-hydroxyphenyl)methyl]-3-phenylpropanamide, N-[(5-chloro-8-hydroxyquinolin-7-yl)-(4-methoxyphenyl)methyl]-3-phenylpropanamide, N-[(8-Hydroxy-5-nitro-quinolin-7-yl)-p-tolyl-methyl]-propionamide, N-[{8-hydroxy-5-nitro-7-quinolinyl}(4-methylphenyl)methyl]acetamide, and N-[(8-hydroxyquinolin-7-yl)-(2-methoxyphenyl)methyl]pentanamide.

Moreover, any compound of formula (I), (II) or (III) can be present as a metal chelate, such that embodied herein are the isolated compounds mentioned above to which one or more metal ions are bound, such as but not limited to iron (II), iron (III), Mn (II), Mn (III), Mn (IV), Mn (VI) or Mn (VII), or a compound of formula (I), (II) or (III) that has entered a biological system such as a tissue, cell, or subcellular compartment such as but not limited to a mitochondrion, and therein binds to one or more free metal ions present therein, and has become activated to carry out the various beneficial functions mentioned herein throughout. As noted above, the compounds, in one embodiment, are active in cells that have elevated levels of intracellular iron, which in itself is pathologic or portends adverse cellular physiology; binding to the compound of the invention reduces the excess intracellular iron level and/or activates the catalytic activity of the compound, reducing levels of oxidants, decreasing oxidant stress and reducing pathology. Mechanisms including binding to intracellular metal ions, which reduces the ability of such ions to participate in the generation of reactive oxygen species, and/or catalytic activity to degrade reactive oxygen species such as superoxides and peroxides, are potential mechanisms benefitting the treatment of diseases of disrupted iron metabolism. As noted above, Applicants are not bound to the mechanism described herein.

A number of important subclasses of the structure of formula (I) deserves separate mention; these include subclasses in which:

i) $R^1$ is hydrogen, hydroxy, halogen, cyano, nitro, $NH_2$ or is alkyloxy,
ii) $R^2$ is hydroxy or alkoxy,
iii) $R^3$ is an optionally substituted aralkyl group,
iv) A is a heterocyclic group, v) A is a heteroaryl group,
vi) A is an aryl group, and/or
vii) A is a substituted aryl group.

In certain embodiments, $R^1$ is a halogen. In certain embodiments, $R^1$ is chloro. In certain embodiments, $R^2$ is hydroxy. In certain embodiments, $R^3$ is phenyl. In certain embodiments, $R^3$ is benzyl. In certain embodiments, $R^3$ is phenylethyl. In certain embodiments, $R^3$ is phenylpropyl. In certain embodiments, $R^3$ is phenylbutyl. In certain embodiments, $R^3$ is phenylpentyl. In certain embodiments, A is furyl. In certain embodiments A is a substituted phenyl group.

Non-limiting examples of such compounds include N-[(5-chloro-8-hydroxyquinolin-7-yl)-furan-2-ylmethyl]-3-phenylpropanamide, N-[(5-chloro-8-hydroxyquinolin-7-yl)-(3-methoxyphenyl)methyl]-3-phenylpropanamide, N-[(5-chloro-8-hydroxyquinolin-7-yl)-(4-dimethylaminophenyl)methyl]-3-phenylpropanamide, N-[(5-chloro-8-hydroxyquinolin-7-yl)-(4-chlorophenyl)methyl]-3-phenylpropanamide, N-[(5-chloro-8-hydroxyquinolin-7-yl)-(3-chlorophenyl)methyl]-3-phenylpropanamide, N-[(5-chloro-8-hydroxyquinolin-7-yl)-(2-chlorophenyl)methyl]-3-phenylpropanamide, N-[(5-chloro-8-hydroxyquinolin-7-yl)-(3,4-dimethoxyphenyl)methyl]-3-phenylpropanamide, N-[(5-chloro-8-hydroxyquinolin-7-yl)-(2,4-dimethoxyphenyl)methyl]-3-phenylpropanamide, N-[(5-chloro-8-hydroxyquinolin-7-yl)-(3,4,5-trimethoxyphenyl)methyl]-3-phenylpropanamide, N-[(5-chloro-8-hydroxyquinolin-7-yl)-(2-bromophenyl)methyl]-3-phenylpropanamide, N-[(5-chloro-8-hydroxyquinolin-7-yl)-p-tolyl-methyl]-3-phenylpropanamide, N-[(5-chloro-8-hydroxyquinolin-7-yl)-(2-hydroxyphenyl)methyl]-3-phenylpropanamide, and N-[(5-chloro-8-hydroxyquinolin-7-yl)-(4-methoxyphenyl)methyl]-3-phenylpropanamide.

A number of important subclasses of the structure of formula (II) deserves separate mention; these include subclasses in which:
 i) $R^1$ is hydrogen, hydroxy, halogen, cyano, nitro, $NH_2$ or is alkyloxy,
 ii) $R^2$ is hydroxy or alkoxy,
 iii) $R^3$ is an optionally substituted aralkyl group,
 iv) B is oxygen,
 v) B is sulfur,
 vi) B is nitrogen and/or
 vii) $R^5$ one or more hydrogen, hydroxy, halogen, cyano, alkyloxy, nitro, $NH_2$, $NHCOR^4$, $NHSO_2R^4$, $CONHR^4$, $COOR^4$, optionally substituted aliphatic, alicyclic, heteroaliphatic, heterocyclic, aromatic, or heteroaromatic, where $R^4$ is as defined in formula (II) above.

In certain embodiments, $R^1$ is a halogen. In certain embodiments, $R^1$ is chloro. In certain embodiments, $R^2$ is hydroxy. In certain embodiments, $R^3$ is phenyl. In certain embodiments, $R^3$ is benzyl. In certain embodiments, $R^3$ is phenylethyl. In certain embodiments, $R^3$ is phenylpropyl. In certain embodiments, $R^3$ is phenylbutyl. In certain embodiments, $R^3$ is phenylpentyl. In certain embodiments, B is oxygen.

Non-limiting examples of such compounds include N-[(5-chloro-8-hydroxyquinolin-7-yl)-furan-2-ylmethyl]-3-phenylpropanamide.

A number of important subclasses of the structure of formula (III) deserves separate mention; these subclasses include subclasses of the foregoing classes in which:
 i) $R^1$ is hydrogen, hydroxy, halogen, cyano, nitro, $NH_2$ or is alkyloxy,
 ii) $R^2$ is hydroxy or alkoxy,
 iii) $R^3$ is an optionally substituted aralkyl group, and/or
 iv) $R^5$ one or more hydrogen, hydroxy, halogen, cyano, alkyloxy, nitro, $NH_2$, $NHCOR^4$, $NHSO_2R^4$, $CONHR^4$, $COOR^4$, optionally substituted aliphatic, alicyclic, heteroaliphatic, heterocyclic, aromatic, or heteroaromatic, where $R^4$ is described in formula (III) above.

In certain embodiments, $R^1$ is a halogen. In certain embodiments, $R^1$ is chloro. In certain embodiments, $R^2$ is hydroxy. In certain embodiments, $R^3$ is phenyl. In certain embodiments, $R^3$ is benzyl. In certain embodiments, $R^3$ is phenylethyl. In certain embodiments, $R^3$ is phenylpropyl. In certain embodiments, $R^3$ is phenylbutyl. In certain embodiments, $R^3$ is phenylpentyl. In certain embodiments, $R^5$ is other than hydrogen. In certain embodiments, $R^5$ is one or more alkoxy, halo, dimethylamino, or alkyl groups.

Non-limiting examples of such compounds include N-[(5-chloro-8-hydroxyquinolin-7-yl)-(3-methoxyphenyl)methyl]-3-phenylpropanamide, N-[(5-chloro-8-hydroxyquinolin-7-yl)-(4-dimethylaminophenyl)methyl]-3-phenylpropanamide, N-[(5-chloro-8-hydroxyquinolin-7-yl)-(4-chlorophenyl)methyl]-3-phenylpropanamide, N-[(5-chloro-8-hydroxyquinolin-7-yl)-(3-chlorophenyl)methyl]-3-phenylpropanamide, N-[(5-chloro-8-hydroxyquinolin-7-yl)-(2-chlorophenyl)methyl]-3-phenylpropanamide, N-[(5-chloro-8-hydroxyquinolin-7-yl)-(3,4-dimethoxyphenyl)methyl]-3-phenylpropanamide, N-[(5-chloro-8-hydroxyquinolin-7-yl)-(2,4-dimethoxyphenyl)methyl]-3-phenylpropanamide, N-[(5-chloro-8-hydroxyquinolin-7-yl)-(3,4,5-trimethoxyphenyl)methyl]-3-phenylpropanamide, N-[(5-chloro-8-hydroxyquinolin-7-yl)-(2-bromophenyl)methyl]-3-phenylpropanamide, N-[(5-chloro-8-hydroxyquinolin-7-yl)-p-tolyl-methyl]-3-phenylpropanamide, N-[(5-chloro-8-hydroxyquinolin-7-yl)-(2-hydroxyphenyl)methyl]-3-phenylpropanamide, and N-[(5-chloro-8-hydroxyquinolin-7-yl)-(4-methoxyphenyl)methyl]-3-phenylpropanamide.

Pharmaceutical compositions comprising any of the aforementioned compounds and classes and subclasses of special interest are embraced herein.

Embodied herein are compounds as described above and pharmaceutical compositions thereof. It will be appreciated that the compounds and compositions, according to the methods of the present invention, may be administered using any amount and any route of administration effective for the treatment of conditions or diseases in which increasing mitochondrial activity, decreasing intracellular and/or intramitochondrial iron, and/or decreasing intracellular and/or intramitochondrial oxidative stress has a therapeutically useful role. Thus, the expression "effective amount" as used herein, refers to a sufficient amount of agent to modulate mitochondrial activity, intracellular and/or intramitochondrial iron, and/or intracellular and/or intramitochondrial oxidative stress, and to exhibit a therapeutic effect. The exact amount required will vary from subject to subject, depending on the species, age, and general condition of the subject, the particular therapeutic agent, its mode and/or route of administration, and the like. The compounds of the invention are preferably formulated in dosage unit form for ease of administration and uniformity of dosage. The expression "dosage unit form" as used herein refers to a physically discrete unit of therapeutic agent appropriate for the patient to be treated. It will be understood, however, that the total daily usage of the compounds and compositions of the present invention will be decided by the attending physician within the scope of sound medical judgment. The specific therapeutically effective dose level for any particular patient or organism will depend upon a variety of factors including the disorder being treated and the severity of the disorder; the activity of the specific compound employed; the specific composition employed; the age, body weight, general health, sex and diet of the patient;

the time of administration, route of administration, and rate of excretion of the specific compound employed; the duration of the treatment; drugs used in combination or coincidental with the specific compound employed; and like factors well known in the medical arts.

Furthermore, after formulation with an appropriate pharmaceutically acceptable carrier in a desired dosage, the pharmaceutical compositions of this invention can be administered to humans and other animals orally, rectally, parenterally, intracisternally, intravaginally, intraperitoneally, subcutaneously, intradermally, intra-ocularly, topically (as by powders, ointments, or drops), buccally, as an oral or nasal spray, or the like, depending on the severity of the disease or disorder being treated. In certain embodiments, the compounds of the invention may be administered at dosage levels of about 0.001 mg/kg to about 50 mg/kg, preferably from about 0.1 mg/kg to about 10 mg/kg for parenteral administration, or preferably from about 1 mg/kg to about 50 mg/kg, more preferably from about 10 mg/kg to about 50 mg/kg for oral administration, of subject body weight per day, one or more times a day, to obtain the desired therapeutic effect. It will also be appreciated that dosages smaller than 0.001 mg/kg or greater than 50 mg/kg (for example 50-100 mg/kg) can be administered to a subject. In certain embodiments, compounds are administered orally or parenterally.

In another embodiment of methods and compositions of the present invention, the pharmaceutical compositions are administered orally, and are thus formulated in a form suitable for oral administration, i.e. as a solid or a liquid preparation. Suitable solid oral formulations include tablets, capsules, pills, granules, pellets and the like. Suitable liquid oral formulations include solutions, suspensions, dispersions, emulsions, oils and the like. In another embodiment of the present invention, the active ingredient is formulated in a capsule. In accordance with this embodiment, the compositions of the present invention comprise, in addition to the active compound and the inert carrier or diluent, a hard gelatin capsule.

In another embodiment, the pharmaceutical compositions are administered by intravenous, intra-arterial, subcutaneous or intra-muscular injection of a liquid preparation. Suitable liquid formulations include solutions, suspensions, dispersions, emulsions, oils and the like. In another embodiment, the pharmaceutical compositions are administered intravenously and are thus formulated in a form suitable for intravenous administration. In another embodiment, the pharmaceutical compositions are administered intra-arterially and are thus formulated in a form suitable for intra-arterial administration. In another embodiment, the pharmaceutical compositions are administered intra-muscularly and are thus formulated in a form suitable for intra-muscular administration.

In another embodiment, the pharmaceutical compositions are administered topically to body surfaces and are thus formulated in a form suitable for topical administration. Topical formulations include, in another embodiment, gels, ointments, creams, lotions, drops and the like.

In another embodiment, the pharmaceutical composition is administered as a suppository, for example a rectal suppository or a urethral suppository. In another embodiment, the pharmaceutical composition is administered by subcutaneous implantation of a pellet. In another embodiment, the pellet provides for controlled release of active agent over a period of time.

In another embodiment, the active compound is delivered in a vesicle, e.g. a liposome.

In other embodiments, carriers or diluents used in methods of the present invention include, but are not limited to, a gum, a starch (e.g. corn starch, pregeletanized starch), a sugar (e.g., lactose, mannitol, sucrose, dextrose), a cellulosic material (e.g. microcrystalline cellulose), an acrylate (e.g. polymethylacrylate), calcium carbonate, magnesium oxide, talc, or mixtures thereof.

In other embodiments, pharmaceutically acceptable carriers for liquid formulations are aqueous or non-aqueous solutions, suspensions, emulsions or oils. Examples of non-aqueous solvents are propylene glycol, polyethylene glycol, and injectable organic esters such as ethyl oleate. Aqueous carriers include water, alcoholic/aqueous solutions, emulsions or suspensions, including saline and buffered media. Examples of oils are those of animal, vegetable, or synthetic origin, for example, peanut oil, soybean oil, olive oil, sunflower oil, fish-liver oil, another marine oil, or a lipid from milk or eggs.

In another embodiment, parenteral vehicles (for subcutaneous, intravenous, intra-arterial, or intramuscular injection) include sodium chloride solution, Ringer's dextrose, dextrose and sodium chloride, lactated Ringer's and fixed oils. Intravenous vehicles include fluid and nutrient replenishers, electrolyte replenishers such as those based on Ringer's dextrose, and the like. Examples are sterile liquids such as water and oils, with or without the addition of a surfactant and other pharmaceutically acceptable adjuvants. In general, water, saline, aqueous dextrose and related sugar solutions, and glycols such as propylene glycols or polyethylene glycol are preferred liquid carriers, particularly for injectable solutions. Examples of oils are those of animal, vegetable, or synthetic origin, for example, peanut oil, soybean oil, olive oil, sunflower oil, fish-liver oil, another marine oil, or a lipid from milk or eggs.

In other embodiments, the compositions further comprise binders (e.g. acacia, cornstarch, gelatin, carbomer, ethyl cellulose, guar gum, hydroxypropyl cellulose, hydroxypropyl methyl cellulose, povidone), disintegrating agents (e.g. cornstarch, potato starch, alginic acid, silicon dioxide, croscarmelose sodium, crospovidone, guar gum, sodium starch glycolate), buffers (e.g., Tris-HCl, acetate, phosphate) of various pH and ionic strength, additives such as albumin or gelatin to prevent absorption to surfaces, detergents (e.g., Tween 20, Tween 80, Pluronic F68, bile acid salts), protease inhibitors, surfactants (e.g. sodium lauryl sulfate), permeation enhancers, solubilizing agents (e.g., glycerol, polyethylene glycerol), anti-oxidants (e.g., ascorbic acid, sodium metabisulfite, butylated hydroxyanisole), stabilizers (e.g. hydroxypropyl cellulose, hyroxypropylmethyl cellulose), viscosity increasing agents (e.g. carbomer, colloidal silicon dioxide, ethyl cellulose, guar gum), sweeteners (e.g. aspartame, citric acid), preservatives (e.g., Thimerosal, benzyl alcohol, parabens), lubricants (e.g. stearic acid, magnesium stearate, polyethylene glycol, sodium lauryl sulfate), flow-aids (e.g. colloidal silicon dioxide), plasticizers (e.g. diethyl phthalate, triethyl citrate), emulsifiers (e.g. carbomer, hydroxypropyl cellulose, sodium lauryl sulfate), polymer coatings (e.g., poloxamers or poloxamines), coating and film forming agents (e.g. ethyl cellulose, acrylates, polymethacrylates) and/or adjuvants. Each of the above excipients represents a separate embodiment of the present invention.

In another embodiment, the pharmaceutical compositions provided herein are controlled-release compositions, i.e. compositions in which the active compound is released over a period of time after administration. Controlled- or sustained-release compositions include formulation in lipophilic depots (e.g. fatty acids, waxes, oils). In another embodiment, the composition is an immediate-release composition, i.e. a composition in which of the active compound is released immediately after administration.

In another embodiment, the pharmaceutical composition is delivered in a controlled release system. For example, the agent may be administered using intravenous infusion, an implantable osmotic pump, a transdermal patch, liposomes, or other modes of administration. In one embodiment, a pump may be used (see Langer, supra; Sefton, CRC Crit. Ref. Biomed. Eng. 14:201 (1987); Buchwald et al., Surgery 88:507 (1980); Saudek et al., N. Engl. J. Med. 321:574 (1989). In another embodiment, polymeric materials are used; e.g. in microspheres in or an implant. In yet another embodiment, a controlled release system is placed in proximity to the target cell, thus requiring only a fraction of the systemic dose (see, e.g., Goodson, in Medical Applications of Controlled Release, supra, vol. 2, pp. 115-138 (1984); and Langer R, Science 249: 1527-1533 (1990).

The compositions also include, in another embodiment, incorporation of the active material into or onto particulate preparations of polymeric compounds such as polylactic acid, polglycolic acid, hydrogels, etc, or onto liposomes, microemulsions, micelles, unilamellar or multilamellar vesicles, erythrocyte ghosts, or spheroplasts.) Such compositions will influence the physical state, solubility, stability, rate of in vivo release, and rate of in vivo clearance.

Also included in the present invention are particulate compositions coated with polymers (e.g. poloxamers or poloxamines) and the compound coupled to antibodies directed against tissue-specific receptors, ligands or antigens or coupled to ligands of tissue-specific receptors.

Also comprehended by the invention are compounds modified by the covalent attachment of water-soluble polymers such as polyethylene glycol, copolymers of polyethylene glycol and polypropylene glycol, carboxymethyl cellulose, dextran, polyvinyl alcohol, polyvinylpyrrolidone or polyproline. The modified compounds are known to exhibit substantially longer half-lives in blood following intravenous injection than do the corresponding unmodified compounds. Such modifications may also increase the compound's solubility in aqueous solution, eliminate aggregation, enhance the physical and chemical stability of the compound, and greatly reduce the immunogenicity and reactivity of the compound. As a result, the desired in vivo biological activity may be achieved by the administration of such polymer-compound abducts less frequently or in lower doses than with the unmodified compound.

Each of the above additives, excipients, formulations and methods of administration represents a separate embodiment of the present invention.

In one embodiment, the methods of the present invention comprise administering an active compound as the sole active ingredient. However, also encompassed within the scope of the present invention are methods for treating diseases and disorders that comprise administering the active compound in combination with one or more therapeutic agents. In another embodiment, these agents are appropriate for the disease or disorder that is being treated, as is well known in the art.

In one embodiment, the methods of the present invention comprise administering an active compound as the sole active ingredient. However, also encompassed within the scope of the present invention are methods for treating diseases and disorders that comprise administering the active compound in combination with one or more therapeutic agents. In another embodiment, these agents are appropriate for the disease or disorder that is being treated, as is well known in the art.

Some of the foregoing compounds can comprise one or more asymmetric centers, and thus can exist in various isomeric forms, e.g., stereoisomers and/or diastereomers. Thus, inventive compounds and pharmaceutical compositions thereof may be in the form of an individual enantiomer, diastereomer or geometric isomer, or may be in the form of a mixture of stereoisomers. In certain embodiments, the compounds of the invention are enantiopure compounds. In certain other embodiments, mixtures of stereoisomers or diastereomers are provided. In other embodiments, racemic mixtures are provided.

Furthermore, certain compounds, as described herein may have one or more double bonds that can exist as either the Z or E isomer, unless otherwise indicated. The invention additionally encompasses the compounds as individual isomers substantially free of other isomers and alternatively, as mixtures of various isomers, e.g., racemic mixtures of stereoisomers. In addition to the above-mentioned compounds per se, this invention also encompasses pharmaceutically acceptable derivatives of these compounds and compositions comprising one or more compounds of the invention and one or more pharmaceutically acceptable excipients or additives.

The foregoing description is illustrated by the following non-limiting examples.

EXAMPLES

Example 1

Preparation of Compounds of the Invention

The practitioner has a well-established literature of small molecule chemistry to draw upon, in combination with the information contained herein, for guidance on synthetic strategies, protecting groups, and other materials and methods useful for the synthesis of the compounds of this invention.

The various references cited herein provide helpful background information on preparing compounds similar to the inventive compounds described herein or relevant intermediates, as well as information on formulation, uses, and administration of such compounds which may be of interest.

Moreover, the practitioner is directed to the specific guidance and examples provided in this document relating to various exemplary compounds and intermediates thereof.

The compounds of this invention and their preparation can be understood further by the examples that illustrate some of the processes by which these compounds are prepared or used. It will be appreciated, however, that these examples do not limit the invention. Variations of the invention, now known or further developed, are considered to fall within the scope of the present invention as described herein and as hereinafter claimed.

According to the present invention, any available techniques can be used to make or prepare the inventive compounds or compositions including them. For example, a variety of solution phase synthetic methods such as those discussed in detail below may be used. Alternatively or additionally, the inventive compounds may be prepared using any of a variety combinatorial techniques, parallel synthesis and/or solid phase synthetic methods known in the art.

It will be appreciated as described below, that a variety of inventive compounds can be synthesized according to the methods described herein. The starting materials and reagents used in preparing these compounds are either available from commercial suppliers such as Aldrich Chemical Company (Milwaukee, Wis.), Bachem (Torrance, Calif.), Sigma (St. Louis, Mo.), or are prepared by methods well known to a person of ordinary skill in the art following procedures described in such references as Fieser and Fieser 1991, "Reagents for Organic Synthesis", vols 1-17, John Wiley and Sons, New York, N.Y., 1991; Rodd 1989 "Chemistry of Carbon Compounds", vols. 1-5 and supps, Elsevier Science Publishers, 1989; "Organic Reactions", vols 1-40, John Wiley and Sons, New York, N.Y., 1991; March 2001, "Advanced Organic Chemistry", 5th ed. John Wiley and Sons, New York, N.Y.; and Larock 1990, "Comprehensive Organic Transformations: A Guide to Functional Group Preparations", 2nd ed. VCH Publishers. These schemes are merely illustrative of some methods by which the compounds of this invention can be synthesized, and various modifications to these schemes can be made and will be suggested to a person of ordinary skill in the art having regard to this disclosure.

The starting materials, intermediates, and compounds of this invention may be isolated and purified using conventional techniques, including filtration, distillation, crystallization, chromatography, and the like. They may be characterized using conventional methods, including physical constants and spectral data.

General Reaction Procedures:

Unless mentioned specifically, reaction mixtures are stirred using a magnetically driven stirrer bar. An inert atmosphere refers to either dry argon or dry nitrogen. Reactions are monitored either by thin layer chromatography, by proton nuclear magnetic resonance (NMR) or by high-pressure liquid chromatography (HPLC), of a suitably worked up sample of the reaction mixture.

General Work Up Procedures:

Unless mentioned specifically, reaction mixtures are cooled to room temperature or below then quenched, when necessary, with either water or a saturated aqueous solution of ammonium chloride. Desired products are extracted by partitioning between water and a suitable water-immiscible solvent (e.g. ethyl acetate, dichloromethane, diethyl ether). The desired product containing extracts are washed appropriately with water followed by a saturated solution of brine. On occasions where the product containing extract is deemed to contain residual oxidants, the extract is washed with a 10% solution of sodium sulphite in saturated aqueous sodium bicarbonate solution, prior to the aforementioned washing procedure. On occasions where the product containing extract is deemed to contain residual acids, the extract is washed with saturated aqueous sodium bicarbonate solution, prior to the aforementioned washing procedure (except in those cases where the desired product itself had acidic character). On occasions where the product containing extract is deemed to contain residual bases, the extract is washed with 10% aqueous citric acid solution, prior to the aforementioned washing procedure (except in those cases where the desired product itself had basic character). Post washing, the desired product containing extracts are dried over anhydrous magnesium sulphate, and then filtered. The crude products are then isolated by removal of solvent(s) by rotary evaporation under reduced pressure, at an appropriate temperature (generally less than 45° C.).

General Purification Procedures:

Unless mentioned specifically, chromatographic purification refers to flash column chromatography on silica, using a single solvent or mixed solvent as eluent. Suitably purified desired product containing elutes are combined and concentrated under reduced pressure at an appropriate temperature (generally less than 45° C.) to constant mass.

Synthesis of Exemplary Compounds:

Unless otherwise indicated, starting materials are either commercially available or readily accessibly through laboratory synthesis by anyone reasonably familiar with the art. Described generally below, are procedures and general guidance for the synthesis of compounds as described generally and in subclasses and species herein.

Compounds embodied herein were synthesized as shown in the scheme below using a route that employs a microwave-assisted, 3-component Mannich-type reaction (Gilbert, A. M. et al. N-((8-hydroxy-5-substituted-quinolin-7-yl)(phenyl)methyl)-2-phenyloxy/amino-acetamide inhibitors of ADAMTS-5 (Aggrecanase-2). Bioorg Med Chem Lett 18, 6454-7 (2008)) with an average yield of 60%. After work-up, each compound was purified by HPLC to >95% purity (LC/MS).

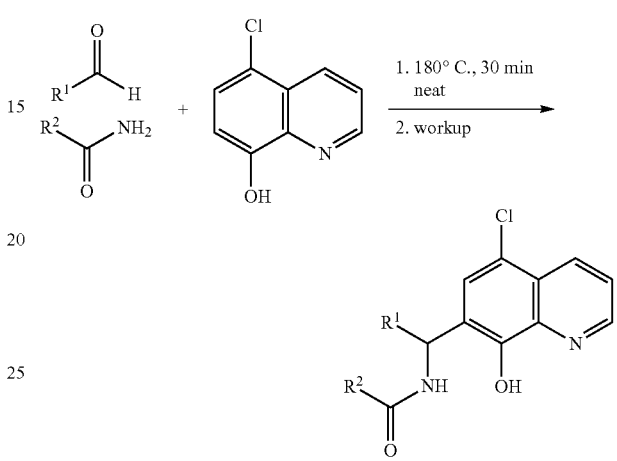

All compounds were prepared according to the above scheme following a similar method. To a microwave vial, 0.5 mmol of hydroxyquinoline, 0.5 mmol aldehyde (where $R^1$ corresponds to A in formula (I)) and 0.5 mmol amide (where $R^2$ corresponds to $R^3$ in formula (I)) were added. The vial was then heated to 120° C. for 30 min. The solids were purified by trituration with 1:1 hexanes:ethyl acetate. The suspension was filtered and the solids washed 3 times with 1:1 hexanes: ethyl acetate. The solids were then further purified by preparative HPLC prior to testing.

Following the guidance above, the following compounds were prepared Other compounds were obtained from commercial sources.

| Compound | Molecular weight $(M + H^+)$ |
|---|---|
| N-[(5-chloro-8-hydroxyquinolin-7-yl)-thiophen-2-ylmethyl]-3-phenylpropanamide | 423.0945 |
| N-[(5-chloro-8-hydroxyquinolin-7-yl)-thiophen-2-ylmethyl]pentanamide | 359.0976 |
| N-[(5-chloro-8-hydroxyquinolin-7-yl)-furan-2-ylmethyl]-3-phenylpropanamide | 407.1169 |
| N-[(5-chloro-8-hydroxyquinolin-7-yl)-furan-2-ylmethyl]propanamide | 331.0854 |
| N-[(5-chloro-8-hydroxyquinolin-7-yl)-furan-2-ylmethyl]pentanamide | 359.1171 |
| N-[(5-chloro-8-hydroxyquinolin-7-yl)-tolyl]-3-phenylpropanamide | 417.1417 |
| N-[(5-chloro-8-hydroxyquinolin-7-yl)-(3-methoxyphenyl)methyl]-3-phenylpropanamide | 447.1494 |
| N-[(5-chloro-8-hydroxyquinolin-7-yl)-(4-dimethylaminophenyl)methyl]-3-phenylpropanamide | 460.1807 |
| N-[(5-chloro-8-hydroxyquinolin-7-yl)-(4-chlorophenyl)methyl]-3-phenylpropanamide | 473.0792 $(M + Na^+)$ |
| N-[(5-chloro-8-hydroxyquinolin-7-yl)-(3-chlorophenyl)methyl]-3-phenylpropanamide | 451.0992 |
| N-[(5-chloro-8-hydroxyquinolin-7-yl)-(2-chlorophenyl)methyl]-3-phenylpropanamide | 451.0959 |
| N-[(5-chloro-8-hydroxyquinolin-7-yl)-(3,4-dimethoxyphenyl)methyl]-3-phenylpropanamide | 477.1604 |

-continued

| Compound | Molecular weight (M + H+) |
|---|---|
| N-[(5-chloro-8-hydroxyquinolin-7-yl)-(2,4-dimethoxyphenyl)methyl]-3-phenylpropanamide | 477.1588 |
| N-[(5-chloro-8-hydroxyquinolin-7-yl)-(3,4,5-trimethoxyphenyl)methyl]-3-phenylpropanamide | 507.1702 |
| N-[(5-chloro-8-hydroxyquinolin-7-yl)-(2-bromophenyl)methyl]-3-phenylpropanamide | 495.0465 |
| N-[(5-chloro-8-hydroxyquinolin-7-yl)-p-tolyl-methyl]-3-phenylpropanamide | 431.1533 |
| N-[(5-chloro-8-hydroxyquinolin-7-yl)-(2-hydroxyphenyl)methyl]-3-phenylpropanamide | 433.1299 |
| N-[(5-chloro-8-hydroxyquinolin-7-yl)-(4-methoxyphenyl)methyl]-3-phenylpropanamide | 447.1483 |

Example 2

Yeast-Based Screening Assay

The aim of this assay is to identify compounds that can improve mitochondrial function in yeast lacking Yfh1p grown in a non-fermentable growth medium. The yeast Yfh1p expression construct used in this study has a galactose-inducible, glucose-repressible promoter driving Yfh1p production. Yfh1p is expressed when yeast are grown in the presence of galactose and inhibited when they are grown in the presence of dextrose. Growing the cells in the presence of dextrose not only turns off the expression of Yfh1p, but also leads to the depletion of Yfh1p in the cells. Transferring the Yfh1p-depleted cells into a non-fermentable, glycerol-based medium dictates that the yeast must use an oxidative pathway. Adding drugs that can bypass the lack of Yfh1p lead to recovered mitochondrial (respiratory) function as demonstrated by the metabolism of the tetrazolium dye, WST-1. WST-1 is a stable reagent, often used to monitor cell proliferation, that has a good linear range and shows accelerated color development. Cleavage of the tetrazolium salt to formazan is accompanied by an increase in absorbance at 450 nm.

Compounds in the single dose assay were evaluated on the basis of Fold Induction compared to yeast only, and those in the dose response assay on percent activation, i.e. percent induction of tetrazolium dye reduction in yeast grown in a non-fermentable growth medium. Percent activation was calculated using the optical density in control wells with cells treated with positive control compound (25 uM methyl 4-(1,2,4,5-tetraazin-3-yl)phenyl ether (MLSMR External ID: MLS000550612; PubChem SID: 14718875)) as full induction of tetrazolium dye reduction (100% activation), and wells with cells grown in medium without methyl 4-(1,2,4,5-tetraazin-3-yl)phenyl ether as an indicator of 0% activation. Library compounds were screened at 50 uM. From the 50 uM single dose assay, 1250 compounds with significant tetrazolium dye reduction were selected for confirmatory dose response assay. These compounds were screened in a 10-point dilution series ranging from 0.01 to 100 uM.

The following screening protocol was followed. Yeast cells containing an inducible/repressible promoter for Yfh1p expression were cultured in induction medium (Yfh1 on) with Galactose as the carbon source, and then shifted to repression medium (Yfh1 off) with Dextrose as the carbon source (for 24 hours) to allow Yfh1 protein to decay. The cells were then incubated for 24 h in respiration-only medium (Yfh1 off) with Glycerol as the carbon source to allow cells to equilibrate, and then plated in 384 well plates in respiration-only medium (Yfh1 off) with glycerol as carbon source, in the presence of Tetrazolium dye (WST-1) for 72 hours.

Preparation of Assay
1. Cells were streaked out on a YPGal agar plate and grown inverted for 3 days at 30 C.
2. A colony was selected and 10 mL of YPGal medium inoculated and grown over night at 30 C with shaking.
3. The cells were counted on a coulter counter, centrifuged at 1400 g for 5 min in dextrose (CSMM-D) medium, washed twice to remove all galactose, and resuspended in CSMM-D medium at a cell density of 2 to the power of 5 cells/mL.
4. Frozen stocks were prepared at this point, in dextrose medium. For these dextrose stock solutions, enough culture was grown in dextrose media over night with shaking at 30 C, to get a cell density of ~2 to the power of 7 cells/mL. The cells were centrifuged at 1400 g for 5 min and the pellet resuspended in glycerol freezing medium at a cell density of 2 to the power of 8 cells/mL.
5. The day before the screen, frozen culture was thawed at room temperature and resuspended in glycerol (CSMM-G) medium.
6. The culture was grown over night at 30 C with shaking and the cells counted and diluted in CSMM-G medium for a final cell density of 4 to the power of 6 cells/mL.
7. Methyl 4-(1,2,4,5-tetraazin-3-yl)phenyl ether (positive control), CSMM-G medium alone (negative control) and compounds were plated with DMSO at 200× concentration (final concentrations: methyl 4-(1,2,4,5-tetraazin-3-yl)phenyl ether 25 uM, compounds 50 uM, DMSO 0.5%) in 384-well plates: 125 mL/well. For the dose response assay, compounds were plated in a 10-point dilution series ranging from 0.01 to 100 uM, at 1% DMSO.
8. 10 uL of a mixture of WST-1 and CSMM-G medium (1 volume WST-1 to 3 volumes CSMM-G medium) was added to each well, followed by 15 uL/well of diluted yeast/CSMM-G medium. Plates were incubated at 30 C in a humidified chamber.
9. After 72 h incubation, plates were shaken for 30 s and OD450 was read in an EnVision (PerkinElmer) multilabel plate reader.

Media Preparation.
1. YPGal (1 L): 10 g yeast extract (BD #212750); 20 g galactose (Sigma #G0750); 20 g agar (BD#214010); 20 g peptone (BD#211677). Make volume up to 990 mL with MQ water. Autoclave at 121 C for 15 min Add 10 mL Pen/Strep (invitrogen/GIBCO cat #15140-155).
2. CSMM-D (Complete Synthetic Minimal Medium-Dextrose) (1 L): 6.7 g yeast nitrogen base w/o amino acids (sigma#Y0626); 20 g dextrose (Fisher#D16500). Make volume up to 950 mL with MQ water. Autoclave at 121 C for 15 min Add 40 mL Amino Acid Mix. Add 10 mL Pen/Strep (invitrogen/GIBCO cat #15140-155).
3. CSMM-G (Complete Synthetic Minimal Medium-Glycerol) (1 L): 6.7 g yeast nitrogen base w/o amino acids (sigma #Y0626); 30 mL glycerol (100%) (Sigma #G7893). Make volume up to 950 mL with MQ water. Autoclave at 121 C for 15 min Add 40 mL Amino Acid Mix. Add 10 mL Pen/Strep (invitrogen/GIBCO cat #15140-155).
4. Glycerol Freezing Medium. Sterile CSMM-glycerol medium with additional 12% glycerol.
5. Amino Acid Mix (1 L): 2 g alanine, 0.5 g adenine, 2 g, arginine, 2 g asparagine, 2 g aspartic acid, 2 g cysteine, 2 g glutamine, 2 g glutamic acid, 2 g glycine, 2 g histidine, 2 g myo-inositol, 2 g isoleucine, 10 g leucine, 2 g lysine, 2 g methionine, 2 g phenylalanine, 2 g proline, 2 g serine, 2 g threonine, 2 g tryptophan, 2 g tyrosine, 2 g uracil and 2 g valine.

Example 2

Results of Screening

Single dose assay: An activity threshold of >1.32 fold increase in absorbance over the cell control was calculated as greater than three standard deviations from the median compound Fold Increase. Therefore, compounds that exhibited >1.32 fold increase in absorbance were selected as candidates for the follow-up dose response assay.

The following compounds were active in the screen: N-[(5-chloro-8-hydroxyquinolin-7-yl)-thiophen-2-ylmethyl]-3-phenylpropanamide, N-[(5-chloro-8-hydroxyquinolin-7-yl)-thiophen-2-ylmethyl]pentanamide, N-[(8-hydroxy-5-nitroquinolin-7-yl)-thiophen-2-ylmethyl]butanamide, N-[(8-hydroxy-5-nitro-quinolin-7-yl)-thiophen-2-yl-methyl]-acetamide, N-[(8-hydroxy-5-nitro-quinolin-7-yl)-thiophen-2-yl-methyl]-propionamide, N-[2-furyl(8-hydroxy-5-nitro-7-quinolinyl)methyl]butanamide, N-[(8-Hydroxy-5-nitro-quinolin-7-yl)-p-tolyl-methyl]-propionamide, N-[{8-hydroxy-5-nitro-7-quinolinyl}(4-methylphenyl)methyl]acetamide, N-[(5-chloro-8-hydroxyquinolin-7-yl)-(3,4-dimethoxyphenyl)methyl]propanamide, N-[(8-hydroxyquinolin-7-yl)-(2-methoxyphenyl)methyl]pentanamide and N-[(5-chloro-8-hydroxyquinolin-7-yl)-(4-methoxyphenyl)methyl]propanamide.

Example 3

Additional Screening Assays

One additional screen employs the murine myoblast (C2C12) cell line treated with ferric ammonium citrate (FAC) and L-buthionine (S,R)-sulfoximine (BSO), using ATP measurements. Approximately 4000 cells per well are plated in standard medium in 96-well plates and FAC is added 4 hours later. The cells are incubated overnight (20 h) in standard tissue-culture incubators, after which BSO is added. After another overnight incubation (24 h) ATP content is determined using the CellTiter-Glo assay. The synergistic effects of FAC and BSO in decreasing viability, as measured by ATP content, presumably derive from the combination of increased oxidative stress (secondary to the FAC) with decreased cellular antioxidant capacity (secondary to the BSO).

Cells treated with the compounds embodied herein show a statistically significant improvement in resistance to treatment with FAC and/or BSO, as indicated by a statistically significant improvement in ATP content relative to carrier controls.

A further screening is performed using yeast lacking functional complex V. The effects of several compounds on ATP content in yeast (using the CellTiter-Glo assay) with and without ATP15p, which is required for the function of complex V. Active compounds generally increase ATP dramatically within minutes; the differences from carrier controls diminish with time and equalize over the course of days. These results suggest a pent-up demand for ATP, a burst of new synthesis, and a gradual return to equilibrium levels, which are normally maintained within a fairly narrow range by feedback mechanisms.

Screening is then conducted using yeast lacking functional mitochondrial complexes I, II, III, and IV. Relative to carrier controls, treatment of cells completely lacking Ndi1 (which encodes the yeast equivalent of complex I) with active compounds can induce an increase of ATP of up to 25-fold or more within minutes. The differences from carrier controls diminish with time and equalize over the course of days, suggesting a pent-up demand for ATP, a burst of new synthesis, and a gradual return to equilibrium levels.

Further screening in mammalian cells treated with inhibitors of specific complexes of the ETC is conducted. Rotenone, antimycin A, and oligomycin have been used in experiments with primary FRDA fibroblasts to show that rotenone inhibits complex I in SH-SY5Y cells in the nM range, and kills SH-SY5Y cells in the M range (with 90% death, as assessed by trypan blue exclusion, after 7 days at 60 M). Antimycin A and oligomycin kill SH-SY5Y cells in the high nM range, as assessed by LDH leakage and DNA fragmentation.

Example 4

Additional Screens

In a further screen, the ability of test compounds to rescue HepG2 cells from lethal concentrations of FAC+BSO was evaluated. Conditions included 100 ug/mL FAC and 100 uM BSO, incubated with cells for 48 hours after which viability was determined using the methods described above.

The results showed activity of compounds of the invention in the picomolar range. These results suggest a mechanism of action other than iron chelation, perhaps a catalytic mechanism, such as mimicking SOD and/or catalase. Inventive compounds might be acting as SOD and/or catalase mimetics, perhaps by chelating intracellular Mn (or even Fe). Supporting this hypothesis are the phenotypic similarities between yeast lacking Yfh1p and yeast lacking Sod2p. Activation of the compounds described herein, though the binding of iron—to become SOD and/or catalase mimetics, or to chelates with some other beneficial activity—might explain the unusual combination of high potency and high specificity, since the compounds would be fully active only in cells with high levels of free iron.

In another screen, testing was conducted in the I154F point-mutation model as described above, to determine whether test compounds could rescue I154F FA cells from lethal or sublethal concentrations of FAC and/or BSO. Effective in this screen were the following compounds: N-[(5-chloro-8-hydroxyquinolin-7-yl)-thiophen-2-ylmethyl]-3-phenylpropanamide, N-[(5-chloro-8-hydroxyquinolin-7-yl)-thiophen-2-ylmethyl]pentanamide, N-[(5-chloro-8-hydroxyquinolin-7-yl)-furan-2-ylmethyl]-3-phenylpropanamide, N-[(5-chloro-8-hydroxyquinolin-7-yl)-furan-2-ylmethyl]propanamide, N-[(5-chloro-8-hydroxyquinolin-7-yl)-furan-2-ylmethyl]pentanamide, N-[(5-chloro-8-hydroxyquinolin-7-yl)-tolyl]-3-phenylpropanamide, N-[(5-chloro-8-hydroxyquinolin-7-yl)-(3-methoxyphenyl)methyl]-3-phenylpropanamide, N-[(5-chloro-8-hydroxyquinolin-7-yl)-(4-dimethylaminophenyl)methyl]-3-phenylpropanamide, N-[(5-chloro-8-hydroxyquinolin-7-yl)-(4-chlorophenyl)methyl]-3-phenylpropanamide, N-[(5-chloro-8-hydroxyquinolin-7-yl)-(3-chlorophenyl)methyl]-3-phenylpropanamide, N-[(5-chloro-8-hydroxyquinolin-7-yl)-(2-chlorophenyl)methyl]-3-phenylpropanamide, N-[(5-chloro-8-hydroxyquinolin-7-yl)-(3,4-dimethoxyphenyl)methyl]-3-phenylpropanamide, N-[(5-chloro-8-hydroxyquinolin-7-yl)-(2,4-dimethoxyphenyl)methyl]-3-phenylpropanamide, N-[(5-chloro-8-hydroxyquinolin-7-yl)-(3,4,5-trimethoxyphenyl)methyl]-3-phenylpropanamide, N-[(5-chloro-8-hydroxyquinolin-7-yl)-(2-bromophenyl)methyl]-3-phenylpropanamide, N-[(5-chloro-8-hydroxyquinolin-7-yl)-p-tolyl-methyl]-3-phenylpropanamide, N-[(5-chloro-8-hydroxyquinolin-7-yl)-(2-hydroxyphenyl)methyl]-3-phenylpropanamide(1a-18), and N-[(5-chloro-8-hydroxyquinolin-7-yl)-(4-methoxyphenyl)methyl]-3-phenylpropanamide.

In a further evaluation, the catalytic activity of the test compound was measured by pre-loading with manganese, or various forms of iron, or other metals, and assaying superoxide dismutase activity in vitro using an assay kit from Fluka. Control levels of inhibition of SOD activity was about 4.5%, and 300 nM compound N-[(5-chloro-8-hydroxyquinolin-7-yl)-thiophen-2-ylmethyl]-3-phenylpropanamide pre-loaded with manganese about 5%. However, preloading with iron acetate increased inhibition to about 40%. This eight-fold increase in inhibition by iron suggests that the potency of compounds of the invention are optimal intracellularly when labile iron concentrations are at excess and thereby contributory to pathology through an increase in oxidative stress.

What is claimed is:

1. A method for increasing cellular frataxin gene activity in a yeast or mammalian cell comprising contacting said yeast or mammalian cell with an effective amount of a compound having the structure of formula (I):

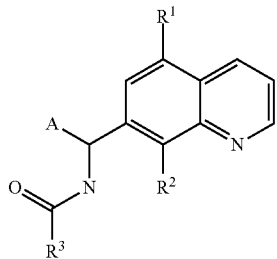

I wherein A is an optionally substituted aliphatic, alicyclic, heteroaliphatic, heterocyclic, aromatic, or heteroaromatic;
$R^1$ is hydrogen, hydroxy, halogen, cyano, alkyloxy, nitro, $NH_2$, $NHCOR^4$, $NHSO_2R^4$, $CONHR^4$, $COOR^4$, or an optionally substituted aliphatic, alicyclic, heteroaliphatic, heterocyclic, aromatic, or heteroaromatic;
$R^2$ is hydroxy or —OR, wherein R is —$C_1$-$C_6$-alkyl, —$C_2$-$C_6$-alkenyl, —$C_2$-$C_6$-alkynyl, —$SO_2NR^4R^6$, —$SO_2R^7$, —$COR^7$, —$COOR^7$ or —$CONR^4R^6$, wherein (a) one or more of the carbon atoms in the alkyl, alkenyl or alkynyl group is each independently optionally replaced with a nitrogen, sulfur or oxygen atom, and (b) the alkyl, alkenyl or alkynyl group is optionally substituted with a —$C_1$-$C_3$-alkyl;
$R^3$ is an optionally substituted aliphatic, alicyclic, heteroaliphatic, heterocyclic, aromatic, or heteroaromatic; and
$R^4$ and $R^6$ are each independently hydrogen, —$C_1$-$C_6$-alkyl, —$C_2$-$C_6$-alkenyl, —$C_2$-$C_6$-alkynyl, —$COR^7$, —$C_5$-$C_7$-aryl, or —$C_5$-$C_{10}$-arylalkyl, wherein (a) one or more of the carbon atoms in the alkyl, alkenyl, alkynyl, aryl or arylalkyl group is each independently optionally replaced with a nitrogen, sulfur or oxygen atom, and (b) the alkyl, alkenyl, alkynyl, aryl or arylalkyl is optionally substituted with an oxygen, a —$C_1$-$C_3$-alkyl, or a —$C_5$-$C_7$-aryl; and
$R^7$ is hydrogen, —$C_1$-$C_6$-alkyl, —$C_2$-$C_6$-alkenyl, —$C_2$-$C_6$-alkynyl, —$C_5$-$C_7$-aryl, or —$C_5$-$C_{10}$-arylalkyl, wherein (a) one or more of the carbon atoms in the alkyl, alkenyl, alkynyl, aryl or arylalkyl group is each independently optionally replaced with a nitrogen, sulfur or oxygen atom, and (b) the alkyl, alkenyl, alkynyl, aryl or arylalkyl is optionally substituted with a halogen, a —$C_1$-$C_3$-alkyl, a —$C_5$-$C_7$-aryl, or —$NR^4R^6$ or —$OR^4$;
or an isomer, stereoisomer, racemate, prodrug, active metabolite, metal chelate, or a pharmaceutically-acceptable derivative or salt form of any of the foregoing.

2. A method for decreasing mitochondrial iron accumulation or for decreasing cellular iron import in a subject, comprising administering to the subject an effective amount of a compound having the structure of formula (I):

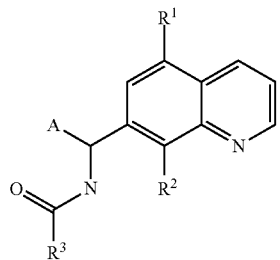

I wherein A is an optionally substituted aliphatic, alicyclic, heteroaliphatic, heterocyclic, aromatic, or heteroaromatic;
$R^1$ is hydrogen, hydroxy, halogen, cyano, alkyloxy, nitro, $NH_2$, $NHCOR^4$, $NHSO_2R^4$, $CONHR^4$, $COOR^4$, or an optionally substituted aliphatic, alicyclic, heteroaliphatic, heterocyclic, aromatic, or heteroaromatic;
$R^2$ is hydroxy or —OR, wherein R is —$C_1$-$C_6$-alkyl, —$C_2$-$C_6$-alkenyl, —$C_2$-$C_6$-alkynyl, —$SO_2NR^4R^6$, —$SO_2R^7$, —$COR^7$, —$COOR^7$ or —$CONR^4R^6$, wherein (a) one or more of the carbon atoms in the alkyl, alkenyl or alkynyl group is each independently optionally replaced with a nitrogen, sulfur or oxygen atom, and (b) the alkyl, alkenyl or alkynyl group is optionally substituted with a —$C_1$-$C_3$-alkyl;
$R^3$ is an optionally substituted aliphatic, alicyclic, heteroaliphatic, heterocyclic, aromatic, or heteroaromatic; and
$R^4$ and $R^6$ are each independently hydrogen, —$C_1$-$C_6$-alkyl, —$C_2$-$C_6$-alkenyl, —$C_2$-$C_6$-alkynyl, —$COR^7$, —$C_5$-$C_7$-aryl, or —$C_5$-$C_{10}$-arylalkyl, wherein (a) one or more of the carbon atoms in the alkyl, alkenyl, alkynyl, aryl or arylalkyl group is each independently optionally replaced with a nitrogen, sulfur or oxygen atom, and (b) the alkyl, alkenyl, alkynyl, aryl or arylalkyl is optionally substituted with an oxygen, a —$C_1$-$C_3$-alkyl, or a —$C_5$-$C_7$-aryl; and
$R^7$ is hydrogen, —$C_1$-$C_6$-alkyl, —$C_2$-$C_6$-alkenyl, —$C_2$-$C_6$-alkynyl, —$C_5$-$C_7$-aryl, or —$C_5$-$C_{10}$-arylalkyl, wherein (a) one or more of the carbon atoms in the alkyl, alkenyl, alkynyl, aryl or arylalkyl group is each independently optionally replaced with a nitrogen, sulfur or oxygen atom, and (b) the alkyl, alkenyl, alkynyl, aryl or arylalkyl is optionally substituted with a halogen, a —$C_1$-$C_3$-alkyl, a —$C_5$-$C_7$-aryl, or —$NR^4R^6$ or —$OR^4$;
or an isomer, stereoisomer, racemate, prodrug, active metabolite, metal chelate, or a pharmaceutically-acceptable derivative or salt form of any of the foregoing, wherein administering said compound increases frataxin gene activity in said subject.

3. The method of claim 2 wherein the subject is a Friedreich's ataxia patient.

4. The method of claim 2 wherein the subject has a neurodegenerative disease, neurodegeneration with brain iron accumulation (NBIA), Friedreich's ataxia, Parkinson's disease, Alzheimer's disease, a mitochondrial encephalopathy, normal aging, hemochromatosis, aceruloplasminemia, thalassemia, attention deficit hyperactivity disorder (ADHD), Tourette's syndrome, diabetes, or age-related macular degeneration.

5. A method for improving mitochondrial or cellular respiratory activity or function in a subject comprising administering to the subject an effective amount of a compound having the structure of formula (I):

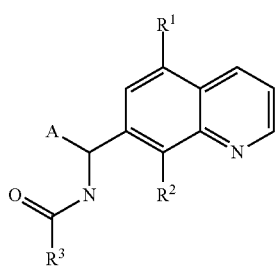

wherein A is an optionally substituted aliphatic, alicyclic, heteroaliphatic, heterocyclic, aromatic, or heteroaromatic;
$R^1$ is hydrogen, hydroxy, halogen, cyano, alkyloxy, nitro, $NH_2$, $NHCOR^4$, $NHSO_2R^4$, $CONHR^4$, $COOR^4$, or an optionally substituted aliphatic, alicyclic, heteroaliphatic, heterocyclic, aromatic, or heteroaromatic;
$R^2$ is hydroxy or —OR, wherein R is —$C_1$-$C_6$-alkyl, —$C_2$-$C_6$-alkenyl, —$C_2$-$C_6$-alkynyl, —$SO_2NR^4R^6$, —$SO_2R^7$, —$COR^7$, —$COOR^7$ or —$CONR^4R^6$, wherein (a) one or more of the carbon atoms in the alkyl, alkenyl or alkynyl group is each independently optionally replaced with a nitrogen, sulfur or oxygen atom, and (b) the alkyl, alkenyl or alkynyl group is optionally substituted with a —$C_1$-$C_3$-alkyl;
$R^3$ is an optionally substituted aliphatic, alicyclic, heteroaliphatic, heterocyclic, aromatic, or heteroaromatic; and
$R^4$ and $R^6$ are each independently hydrogen, —$C_1$-$C_6$-alkyl, —$C_2$-$C_6$-alkenyl, —$C_2$-$C_6$-alkynyl, —$COR^7$, —$C_5$-$C_7$-aryl, or —$C_5$-$C_{10}$-arylalkyl, wherein (a) one or more of the carbon atoms in the alkyl, alkenyl, alkynyl, aryl or arylalkyl group is each independently optionally replaced with a nitrogen, sulfur or oxygen atom, and (b) the alkyl, alkenyl, alkynyl, aryl or arylalkyl is optionally substituted with an oxygen, a —$C_1$-$C_3$-alkyl, or a —$C_5$-$C_7$-aryl; and
$R^7$ is hydrogen, —$C_1$-$C_6$-alkyl, —$C_2$-$C_6$-alkenyl, —$C_2$-$C_6$-alkynyl, —$C_5$-$C_7$-aryl, or —$C_5$-$C_{10}$-arylalkyl, wherein (a) one or more of the carbon atoms in the alkyl, alkenyl, alkynyl, aryl or arylalkyl group is each independently optionally replaced with a nitrogen, sulfur or oxygen atom, and (b) the alkyl, alkenyl, alkynyl, aryl or arylalkyl is optionally substituted with a halogen, a —$C_1$-$C_3$-alkyl, a —$C_5$-$C_7$-aryl, or —$NR^4R^6$ or —$OR^4$;

or an isomer, stereoisomer, racemate, prodrug, active metabolite, metal chelate, or a pharmaceutically-acceptable derivative or salt form of any of the foregoing, wherein administering said compound increases frataxin gene activity in said subject.

6. The method of claim 5 wherein the subject is a Friedreich's ataxia patient.

7. The method of claim 5 wherein the subject has neurodegeneration with brain iron accumulation (NBIA), Parkinson's disease, Alzheimer's disease, a mitochondrial encephalopathy, hemochromatosis, aceruloplasminemia, thalassemia, attention deficit hyperactivity disorder (ADHD), Tourette's syndrome, diabetes, or age-related macular degeneration.

8. A method for treating a subject suffering from Friedreich's ataxia or reducing the symptoms thereof comprising administering to the subject an effective amount of a compound having the structure of formula (I):

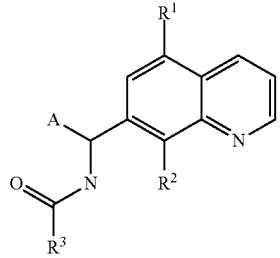

wherein A is an optionally substituted aliphatic, alicyclic, heteroaliphatic, heterocyclic, aromatic, or heteroaromatic;
$R^1$ is hydrogen, hydroxy, halogen, cyano, alkyloxy, nitro, $NH_2$, $NHCOR^4$, $NHSO_2R^4$, $CONHR^4$, $COOR^4$, or an optionally substituted aliphatic, alicyclic, heteroaliphatic, heterocyclic, aromatic, or heteroaromatic;
$R^2$ is hydroxy or —OR, wherein R is —$C_1$-$C_6$-alkyl, —$C_2$-$C_6$-alkynyl, —$SO_2NR^4R^6$, —$SO_2R^7$, —$COR^7$, —$COOR^7$ or —$CONR^4R^6$, wherein (a) one or more of the carbon atoms in the alkyl, alkenyl or alkynyl group is each independently optionally replaced with a nitrogen, sulfur or oxygen atom, and (b) the alkyl, alkenyl or alkynyl group is optionally substituted with a —$C_1$-$C_3$-alkyl;
$R^3$ is an optionally substituted aliphatic, alicyclic, heteroaliphatic, heterocyclic, aromatic, or heteroaromatic; and
$R^4$ and $R^6$ are each independently hydrogen, —$C_1$-$C_6$-alkyl, —$C_2$-$C_6$-alkenyl, —$C_2$-$C_6$-alkynyl, —$COR^7$, —$C_5$-$C_7$-aryl, or —$C_5$-$C_{10}$-arylalkyl, wherein (a) one or more of the carbon atoms in the alkyl, alkenyl, alkynyl, aryl or arylalkyl group is each independently optionally replaced with a nitrogen, sulfur or oxygen atom, and (b) the alkyl, alkenyl, alkynyl, aryl or arylalkyl is optionally substituted with an oxygen, a —$C_1$-$C_3$-alkyl, or a —$C_5$-$C_7$-aryl; and
$R^7$ is hydrogen, —$C_1$-$C_6$-alkyl, —$C_2$-$C_6$-alkenyl, —$C_2$-$C_6$-alkynyl, —$C_5$-$C_7$-aryl, or —$C_5$-$C_{10}$-arylalkyl, wherein (a) one or more of the carbon atoms in the alkyl, alkenyl, alkynyl, aryl or arylalkyl group is each independently optionally replaced with a nitrogen, sulfur or oxygen atom, and (b) the alkyl, alkenyl, alkynyl, aryl or arylalkyl is optionally substituted with a halogen, a —$C_1$-$C_3$-alkyl, a —$C_5$-$C_7$-aryl, or —$NR^4R^6$ or —$OR^4$;

or an isomer, stereoisomer, racemate, prodrug, active metabolite, metal chelate, or a pharmaceutically-acceptable derivative or salt form of any of the foregoing, wherein administering said compound increases frataxin gene activity in said subject.

9. A method for treating a subject having neurodegeneration with brain iron accumulation (NBIA), Friedreich's ataxia, Parkinson's disease, Alzheimer's disease, a mitochondrial encephalopathy, hemochromatosis, aceruloplasminemia, thalassemia, attention deficit hyperactivity disorder (ADHD), Tourette's syndrome, diabetes, or age-related macular degeneration, comprising administering to the subject an effective amount of a compound of having the structure of formula (I):

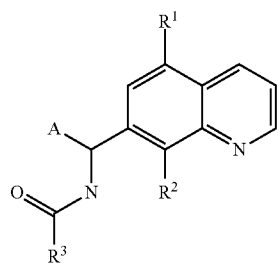

wherein A is an optionally substituted aliphatic, alicyclic, heteroaliphatic, heterocyclic, aromatic, or heteroaromatic;

$R^1$ is hydrogen, hydroxy, halogen, cyano, alkyloxy, nitro, $NH_2$, $NHCOR^4$, $NHSO_2R^4$, $CONHR^4$, $COOR^4$, or an optionally substituted aliphatic, alicyclic, heteroaliphatic, heterocyclic, aromatic, or heteroaromatic;

$R^2$ is hydroxy or —OR, wherein R is —$C_1$-$C_6$-alkyl, —$C_2$-$C_6$-alkenyl, —$C_2$-$C_6$-alkynyl, —$SO_2NR^4R^6$, —$SO_2R^7$, —$COR^7$, —$COOR^7$ or —$CONR^4R^6$, wherein (a) one or more of the carbon atoms in the alkyl, alkenyl or alkynyl group is each independently optionally replaced with a nitrogen, sulfur or oxygen atom, and (b) the alkyl, alkenyl or alkynyl group is optionally substituted with a —$C_1$-$C_3$-alkyl;

$R^3$ is an optionally substituted aliphatic, alicyclic, heteroaliphatic, heterocyclic, aromatic, or heteroaromatic; and $R^4$ and $R^6$ are each independently hydrogen, —$C_1$-$C_6$-alkyl, —$C_2$-$C_6$-alkenyl, —$C_2$-$C_6$-alkynyl, —$COR^7$, —$C_5$-$C_7$-aryl, or —$C_5$-$C_{10}$-arylalkyl, wherein (a) one or more of the carbon atoms in the alkyl, alkenyl, alkynyl, aryl or arylalkyl group is each independently optionally replaced with a nitrogen, sulfur or oxygen atom, and (b) the alkyl, alkenyl, alkynyl, aryl or arylalkyl is optionally substituted with an oxygen, a —$C_1$-$C_3$-alkyl, or a —$C_5$-$C_7$-aryl; and $R^7$ is hydrogen, —$C_1$-$C_6$-alkyl, —$C_2$-$C_6$-alkenyl, —$C_2$-$C_6$-alkynyl, —$C_5$-$C_7$-aryl, or —$C_5$-$C_{10}$-arylalkyl, wherein (a) one or more of the carbon atoms in the alkyl, alkenyl, alkynyl, aryl or arylalkyl group is each independently optionally replaced with a nitrogen, sulfur or oxygen atom, and (b) the alkyl, alkenyl, alkynyl, aryl or arylalkyl is optionally substituted with a halogen, a —$C_1$-$C_3$-alkyl, a —$C_5$-$C_7$-aryl, or —$NR^4R^6$ or —$OR^4$;

or an isomer, stereoisomer, racemate, prodrug, active metabolite, metal chelate, or a pharmaceutically-acceptable derivative or salt form of any of the foregoing, wherein administering said compound increases frataxin gene activity in said subject.

10. The method of claim 1, wherein said mammalian cell is in a subject, and wherein the subject is a Friedreich's ataxia patient.

11. The method of claim 1, wherein the compound is selected from among N-[(5-chloro-8-hydroxyquinolin-7-yl)-thiophen-2-ylmethyl]-3-phenylpropanamide, N-[(5-chloro-8-hydroxyquinolin-7-yl)-thiophen-2-ylmethyl]pentanamide, N-[(5-chloro-8-hydroxyquinolin-7-yl)-thiophen-2-ylmethyl]propanamide, N-[(5-chloro-8-hydroxyquinolin-7-yl)-thiophen-2-ylmethyl]-2-methylpropanamide, N-[(5-chloro-8-hydroxyquinolin-7-yl)-thiophen-2-ylmethyl] butanamide, N-[(5-chloro-8-hydroxyquinolin-7-yl)-thiophen-2-ylmethyl]acetamide, N-[(8-hydroxy-5-nitroquinolin-7-yl)-thiophen-2-ylmethyl]butanamide, N-[(8-hydroxy-5-nitro-quinolin-7-yl)-thiophen-2-yl-methyl]-acetamide, N-[(8-hydroxy-5-nitro-quinolin-7-yl)-thiophen-2-yl-methyl]-propionamide, N-[2-furyl(8-hydroxy-5-mtro-7-quinolinyl)methyl]butanamide, N-[(8-hydroxyquinolin-7-yl)-thiophen-2-ylmethyl]-3-phenylpropanamide, N-[(5-chloro-8-hydroxyquinolin-7-yl)-furan-2-ylmethyl]-3-phenylpropanamide, N-[(5-chloro-8-hydroxyquinolin-7-yl)-furan-2-ylmethyl]propanamide, and N-[(5-chloro-8-hydroxyquinolin-7-yl)-furan-2-ylmethyl]pentanamide.

12. The method of claim 2, wherein the compound is selected from among N-[(5-chloro-8-hydroxyquinolin-7-yl)-thiophen-2-ylmethyl]-3-phenylpropanamide, N-[(5-chloro-8-hydroxyquinolin-7-yl)-thiophen-2-ylmethyl]pentanamide, N-[(5-chloro-8-hydroxyquinolin-7-yl)-thiophen-2-ylmethyl]propanamide, N-[(5-chloro-8-hydroxyquinolin-7-yl)-thiophen-2-ylmethyl]-2-methylpropanamide, N-[(5-chloro-8-hydroxyquinolin-7-yl)-thiophen-2-ylmethyl] butanamide, N-[(5-chloro-8-hydroxyquinolin-7-yl)-thiophen-2-ylmethyl]acetamide, N-[(8-hydroxy-5-nitroquinolin-7-yl)-thiophen-2-ylmethyl]butanamide, N-[(8-hydroxy-5-nitro-quinolin-7-yl)-thiophen-2-yl-methyl]-acetamide, N-[(8-hydroxy-5-nitro-quinolin-7-yl)-thiophen-2-yl-methyl]-propionamide, N-[2-furyl(8-hydroxy-5-mtro-7-quinolinyl)methyl]butanamide, N-[(8-hydroxyquinolin-7-yl)-thiophen-2-ylmethyl]-3-phenylpropanamide, N-[(5-chloro-8-hydroxyquinolin-7-yl)-furan-2-ylmethyl]-3-phenylpropanamide, N-[(5-chloro-8-hydroxyquinolin-7-yl)-furan-2-ylmethyl]propanamide, and N-[(5-chloro-8-hydroxyquinolin-7-yl)-furan-2-ylmethyl]pentanamide.

13. The method of claim 5, wherein the compound is selected from among N-[(5-chloro-8-hydroxyquinolin-7-yl)-thiophen-2-ylmethyl]-3-phenylpropanamide, N-[(5-chloro-8-hydroxyquinolin-7-yl)-thiophen-2-ylmethyl]pentanamide, N-[(5-chloro-8-hydroxyquinolin-7-yl)-thiophen-2-ylmethyl]propanamide, N-[(5-chloro-8-hydroxyquinolin-7-yl)-thiophen-2-ylmethyl]-2-methylpropanamide, N-[(5-chloro-8-hydroxyquinolin-7-yl)-thiophen-2-ylmethyl] butanamide, N-[(5-chloro-8-hydroxyquinolin-7-yl)-thiophen-2-ylmethyl]acetamide, N-[(8-hydroxy-5-nitroquinolin-7-yl)-thiophen-2-ylmethyl]butanamide, N-[(8-hydroxy-5-nitro-quinolin-7-yl)-thiophen-2-yl-methyl]-acetamide, N-[(8-hydroxy-5-nitro-quinolin-7-yl)-thiophen-2-yl-methyl]-propionamide, N-[2-furyl(8-hydroxy-5-mtro-7-quinolinyl)methyl]butanamide, N-[(8-hydroxyquinolin-7-yl)-thiophen-2-ylmethyl]-3-phenylpropanamide, N-[(5-chloro-8-hydroxyquinolin-7-yl)-furan-2-ylmethyl]-3-phenylpropanamide, N-[(5-chloro-8-hydroxyquinolin-7-yl)-furan-2-ylmethyl]propanamide, and N-[(5-chloro-8-hydroxyquinolin-7-yl)-furan-2-ylmethyl]pentanamide.

14. The method of claim 8, wherein the compound is selected from among N-[(5-chloro-8-hydroxyquinolin-7-yl)- thiophen-2-ylmethyl]-3-phenylpropanamide, N-[(5-chloro-8-hydroxyquinolin-7-yl)-thiophen-2-ylmethyl]pentanamide, N-[(5-chloro-8-hydroxyquinolin-7-yl)-thiophen-2-ylmethyl]propanamide, N-[(5-chloro-8-hydroxyquinolin-7-yl)-thiophen-2-ylmethyl]-2-methylpropanamide, N-[(5-chloro-8-hydroxyquinolin-7-yl)-thiophen-2-ylmethyl]butanamide, N-[(5-chloro-8-hydroxyquinolin-7-yl)-thiophen-2-ylmethyl]acetamide, N-[(8-hydroxy-5-nitroquinolin-7-yl)-thiophen-2-ylmethyl]butanamide, N-[(8-hydroxy-5-nitro-quinolin-7-yl)-thiophen-2-yl-methyl]-acetamide, N-[(8-hydroxy-5-nitro-quinolin-7-yl)-thiophen-2-yl-methyl]-propionamide, N-[2-furyl(8-hydroxy-5-mtro-7-quinolinyl)methyl]butanamide, N-[(8-hydroxyquinolin-7-yl)-thiophen-2-ylmethyl]-3-phenylpropanamide, N-[(5-chloro-8-hydroxyquinolin-7-yl)-furan-2-ylmethyl]-3-phenylpropanamide, N-[(5-chloro-8-hydroxyquinolin-7-yl)-furan-2-ylmethyl]propanamide, and N-[(5-chloro-8-hydroxyquinolin-7-yl)-furan-2-ylmethyl]pentanamide.

15. The method of claim 9, wherein the compound is selected from among N-[(5-chloro-8-hydroxyquinolin-7-yl)-thiophen-2-ylmethyl]-3-phenylpropanamide, N-[(5-chloro-8-hydroxyquinolin-7-yl)-thiophen-2-ylmethyl]pentanamide, N-[(5-chloro-8-hydroxyquinolin-7-yl)-thiophen-2-ylmethyl]propanamide, N-[(5-chloro-8-hydroxyquinolin-7-yl)-thiophen-2-ylmethyl]-2-methylpropanamide, N-[(5-chloro-8-hydroxyquinolin-7-yl)-thiophen-2-ylmethyl]butanamide, N-[(5-chloro-8-hydroxyquinolin-7-yl)-thiophen-2-ylmethyl]acetamide, N-[(8-hydroxy-5-nitroquinolin-7-yl)-thiophen-2-ylmethyl]butanamide, N-[(8-hydroxy-5-nitro-quinolin-7-yl)-thiophen-2-yl-methyl]-acetamide, N-[(8-hydroxy-5-nitro-quinolin-7-yl)-thiophen-2-yl-methyl]-propionamide, N-[2-furyl(8-hydroxy-5-mtro-7-quinolinyl)methyl]butanamide, N-[(8-hydroxyquinolin-7-yl)-thiophen-2-ylmethyl]-3-phenylpropanamide, N-[(5-chloro-8-hydroxyquinolin-7-yl)-furan-2-ylmethyl]-3-phenylpropanamide, N-[(5-chloro-8-hydroxyquinolin-7-yl)-furan-2-ylmethyl]propanamide, and N-[(5-chloro-8-hydroxyquinolin-7-yl)-furan-2-ylmethyl]pentanamide.

\* \* \* \* \*